United States Patent
DeAngelis

(10) Patent No.: US 9,925,209 B2
(45) Date of Patent: *Mar. 27, 2018

(54) HEPAROSAN-POLYPEPTIDE AND HEPAROSAN-POLYNUCLEOTIDE DRUG CONJUGATES AND METHODS OF MAKING AND USING SAME

(71) Applicant: The Board of Regents of the University of Oklahoma, Norman, OK (US)

(72) Inventor: Paul L. DeAngelis, Edmond, OK (US)

(73) Assignee: THE BOARD OF REGENTS OF THE UNIVERSITY OF OKLAHOMA, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,003

(22) Filed: Nov. 7, 2014

(65) Prior Publication Data

US 2015/0118185 A1    Apr. 30, 2015

Related U.S. Application Data

(60) Continuation-in-part of application No. 13/715,117, filed on Dec. 14, 2012, now Pat. No. 9,603,945, which is a division of application No. 12/556,324, filed on Sep. 9, 2009, now Pat. No. 9,687,559, and a continuation-in-part of application No. 12/383,046, filed on Mar. 19, 2009, now abandoned.

(60) Provisional application No. 61/901,309, filed on Nov. 7, 2013, provisional application No. 61/179,275, filed on May 18, 2009, provisional application No. 61/095,572, filed on Sep. 9, 2008, provisional application No. 61/038,027, filed on Mar. 19, 2008.

(51) Int. Cl.

| | | |
|---|---|---|
| A61K 31/70 | (2006.01) |
| A61K 31/727 | (2006.01) |
| A61K 31/7088 | (2006.01) |
| A61K 38/19 | (2006.01) |
| A61K 38/28 | (2006.01) |
| A61K 38/27 | (2006.01) |
| A61K 38/22 | (2006.01) |
| A61K 39/395 | (2006.01) |
| A61K 38/50 | (2006.01) |
| A61K 38/21 | (2006.01) |
| A61K 47/61 | (2017.01) |
| A61K 39/00 | (2006.01) |

(52) U.S. Cl.
CPC ........ *A61K 31/7088* (2013.01); *A61K 38/193* (2013.01); *A61K 38/21* (2013.01); *A61K 38/22* (2013.01); *A61K 38/27* (2013.01); *A61K 38/28* (2013.01); *A61K 38/50* (2013.01); *A61K 39/395* (2013.01); *A61K 47/61* (2017.08); *A61K 2039/505* (2013.01); *C12Y 305/01001* (2013.01)

(58) Field of Classification Search
None
See application file for complete search history.

(56) References Cited

U.S. PATENT DOCUMENTS

| | | |
|---|---|---|
| 5,314,876 A | 5/1994 | Lormeau et al. |
| 5,384,398 A | 1/1995 | Lormeau et al. |
| 5,407,911 A | 11/1995 | Rhee et al. |
| 5,550,187 A | 8/1996 | Rhee et al. |
| 5,756,553 A | 5/1998 | Iguchi et al. |
| 5,827,937 A | 10/1998 | Ågerup |
| 5,876,433 A | 3/1999 | Lunn |
| 5,958,899 A | 9/1999 | Zoppetti et al. |
| 6,120,536 A | 9/2000 | Ding et al. |
| 6,156,373 A | 12/2000 | Zhong et al. |
| 6,162,797 A | 12/2000 | Zoppetti et al. |
| 6,444,447 B1 | 9/2002 | DeAngelis |
| 6,562,781 B1 | 5/2003 | Berry et al. |
| 7,244,270 B2 | 7/2007 | Lesh |
| 7,291,673 B2 | 11/2007 | Hubbell et al. |
| 7,579,173 B2 | 8/2009 | DeAngelis et al. |
| 7,842,500 B2 | 11/2010 | Suzuki et al. |
| 8,580,290 B2 | 11/2013 | DeAngelis |
| 8,980,608 B2 | 3/2015 | DeAnelis et al. |
| 2002/0192205 A1 | 12/2002 | Michon et al. |
| 2002/0193156 A1 | 12/2002 | Bucevschi et al. |
| 2003/0017131 A1 | 1/2003 | Park et al. |
| 2004/0087488 A1 | 5/2004 | Parent et al. |
| 2004/0132143 A1 | 7/2004 | DeAngelis et al. |
| 2004/0197868 A1 | 10/2004 | DeAngelis |
| 2005/0255562 A1 | 11/2005 | Rosenberg et al. |
| 2005/0272696 A1 | 12/2005 | DeAngelis |
| 2006/0105431 A1 | 5/2006 | DeAngelis |
| 2006/0116346 A1 | 6/2006 | De Luca et al. |

(Continued)

FOREIGN PATENT DOCUMENTS

| | | |
|---|---|---|
| EP | 1870421 A1 | 12/2007 |
| EP | 1923402 A1 | 5/2008 |

(Continued)

OTHER PUBLICATIONS

Remington (The Science and Practice of Pharmacy, Nineteenth Edition—1995, pp. 710-712, pp. 1463, 1546-1547).*

(Continued)

*Primary Examiner* — Shobha Kantamneni

(74) *Attorney, Agent, or Firm* — Knobbe, Martens, Olson & Bear LLP

(57) ABSTRACT

Compositions containing conjugates of heparosan polymer with at least one drug are disclosed, along with methods of production and use thereof.

27 Claims, 26 Drawing Sheets

(56) References Cited

U.S. PATENT DOCUMENTS

| | | |
|---|---|---|
| 2006/0172967 A1 | 8/2006 | Toida |
| 2006/0188966 A1 | 8/2006 | DeAngelis |
| 2007/0128703 A1 | 6/2007 | DeAngelis et al. |
| 2008/0109236 A1 | 5/2008 | DeAngelis et al. |
| 2008/0112951 A1 | 5/2008 | Phalipon et al. |
| 2008/0220669 A1 | 9/2008 | DeAngelis |
| 2009/0104627 A1 | 4/2009 | Yamamoto et al. |
| 2010/0036001 A1 | 2/2010 | DeAngelis |
| 2012/0108802 A1 | 5/2012 | DeAngelis et al. |
| 2013/0261079 A1 | 10/2013 | DeAngelis et al. |
| 2015/0118185 A1 | 4/2015 | DeAngelis |

FOREIGN PATENT DOCUMENTS

| | | |
|---|---|---|
| JP | 2004018840 | 1/2004 |
| WO | 9222331 A1 | 12/1992 |
| WO | 9741897 A1 | 11/1997 |
| WO | 200027437 | 5/2000 |
| WO | 2002089742 | 5/2002 |
| WO | 2003029261 | 10/2003 |
| WO | WO2006/106950 | * 12/2006 |
| WO | 2007001021 | 1/2007 |
| WO | 2009014559 | 1/2009 |
| WO | 2010030342 | 3/2010 |

OTHER PUBLICATIONS

Riggs et al., Journal of Surgical Research, vol. 108, No. 2, 2002, pp. 279-284.*
PCT Application No. PCT/US02/14581, Paul DeAngelis, International Search Report, dated Jun. 11, 2003.
PCT Application No. PCT/US02/14581, Paul DeAngelis, Written Opinion, dated Aug. 5, 2004.
U.S. Appl. No. 10/142,143, Paul DeAngelis, Requirement for Restriction/Election, dated Mar. 29, 2005.
U.S. Appl. No. 10/142,143, Paul DeAngelis, Response to Election, dated Apr. 29, 2005.
U.S. Appl. No. 10/142,143, Paul DeAngelis, Office Action, dated Oct. 28, 2005.
U.S. Appl. No. 10/142,143, Paul DeAngelis, Response to Office Action, dated Apr. 14, 2006.
U.S. Appl. No. 10/142,143, Paul DeAngelis, Office Action, dated Jun. 22, 2006.
U.S. Appl. No. 10/142,143, Paul DeAngelis, Response to Office Action, dated Dec. 22, 2006.
U.S. Appl. No. 10/142,143, Paul DeAngelis, Final Office Action, dated Apr. 5, 2007.
U.S. Appl. No. 10/142,143, Paul DeAngelis, Amendment Under 37 CRF 1.116, dated Jul. 3, 2007.
Australian Serial No. 2002256501, Paul DeAngelis, Examiner's First Report, dated Nov. 7, 2006.
Australian Serial No. 2002256501, Paul DeAngelis, Response to Examiner's First Report, dated Apr. 24, 2008.
EPO Application No. 02725971.2, Paul DeAngelis, Official Letter, dated Apr. 24, 2006.
EPO Application No. 02725971.2, Paul DeAngelis, Response to Official Letter, dated Nov. 3, 2006.
EPO Application No. 02725971.2, Paul DeAngelis, Official Letter, dated Mar. 2, 2009.
EPO Application No. 02725971.2, Paul DeAngelis, Response to Official Letter, dated Sep. 1, 2009.
EPO Application No. 02725971.2, Paul DeAngelis, Official Letter, dated Apr. 24, 2012.
PCT Application No. PCT/US08/04190, Paul DeAngelis, International Search Report & Written Opinion, dated Mar. 24, 2009.
PCT Application No. PCT/US09/05050, Paul DeAngelis, International Search Report & Written Opinion, dated Sep. 9, 2009.
U.S. Appl. No. 10/814,752, Paul DeAngelis, Requirement for Restriction/Election, dated Jul. 25, 2006.
U.S. Appl. No. 10/814,752, Paul DeAngelis, Amendment & Response to Election, dated Jan. 25, 2007.
U.S. Appl. No. 10/814,752, Paul DeAngelis, Office Action, dated Apr. 16, 2007.
U.S. Appl. No. 10/814,752, Paul DeAngelis, Amendment & Response to Office Action, dated Oct. 16, 2007.
U.S. Appl. No. 10/814,752, Paul DeAngelis, Office Action, dated Dec. 27, 2007.
U.S. Appl. No. 10/814,752, Paul DeAngelis, Amendment & Response to Office Action, dated Jun. 24, 2008.
U.S. Appl. No. 10/814,752, Paul DeAngelis, Final Office Action, dated Dec. 4, 2008.
U.S. Appl. No. 11/975,811, Paul DeAngelis, Requirement for Restriction/Election, dated Aug. 26, 2009.
U.S. Appl. No. 11/975,811, Paul DeAngelis, Amendment & Response to Election, dated Sep. 29, 2009.
U.S. Appl. No. 11/975,811, Paul DeAngelis, Office Action, dated Oct. 29, 2009.
U.S. Appl. No. 11/975,811, Paul DeAngelis, Amendment & Response to Office Action, dated Jan. 26, 2010.
U.S. Appl. No. 11/975,811, Paul DeAngelis, Notice of Allowance with Examiner's Amendment, dated Apr. 12, 2010.
U.S. Appl. No. 11/975,811, Paul DeAngelis, Amendment Under 37 CFR 1.312, dated Jun. 8, 2010.
U.S. Appl. No. 11/906,704, Paul DeAngelis, Requirement for Restriction/Election, dated Nov. 18, 2009.
U.S. Appl. No. 11/906,704, Paul DeAngelis, Amendment & Response to Election, dated Dec. 18, 2009.
U.S. Appl. No. 11/906,704, Paul DeAngelis, Requirement for Restriction/Election, dated Feb. 2, 2010.
U.S. Appl. No. 11/906,704, Paul DeAngelis, Amendment & Response to Election, dated Feb. 24, 2010.
U.S. Appl. No. 11/906,704, Paul DeAngelis, Office Action, dated May 17, 2010.
U.S. Appl. No. 11/906,704, Paul DeAngelis, Amendment & Response to Office Action, dated Nov. 17, 2010.
U.S. Appl. No. 11/906,704, Paul DeAngelis, Final Office Action, dated Jan. 18, 2011.
U.S. Appl. No. 11/906,704, Paul DeAngelis, Pre-Appeal Brief Request for Review, dated Jul. 18, 2011.
U.S. Appl. No. 11/906,704, Paul DeAngelis, Notice of Allowance with Examiner's Amendment, dated Aug. 31, 2011.
U.S. Appl. No. 12/080,060, Paul DeAngelis, Requirement for Restriction/Election, dated Nov. 3, 2010.
U.S. Appl. No. 12/080,060, Paul DeAngelis, Amendment & Response to Election, dated Jan. 19, 2011.
U.S. Appl. No. 12/080,060, Paul DeAngelis, Office Action, dated Feb. 2, 2011.
U.S. Appl. No. 12/080,060, Paul DeAngelis, Amendment & Response to Office Action, dated Aug. 1, 2011.
U.S. Appl. No. 12/080,060, Paul DeAngelis, Final Office Action, dated Dec. 29, 2011.
U.S. Appl. No. 12/080,060, Paul DeAngelis, Amendment & Response to Final Office Action, dated Jun. 28, 2012.
Australian Application No. 2008207616, Paul DeAngelis, Examiner's Report, dated Oct. 18, 2010.
Australian Application No. 2008207616, Paul DeAngelis, Response to Examiner's Report, dated Oct. 18, 2010.
Jing et al.; "Dissection of the two transferase activities of the Pasteurella multocida hyaluronan synthase; two active sites exist in one polypeptide"; Glycobiology, 10(9): 883-889 (2000).
Peppas et al.; "New Challenges in Biomaterials"; Science, 263:1715-1720 (1994).
Manzoni et al.; "Production of K5 Polysaccharides of Different Molecular Weight by *Escherichia coli*"; Journal of Bioactive & Compatible Polymers vol. 11 301-311 (1996).
May, B.J. et al.; Complete genomic sequence of Pasteurella multocida, Pm70. Proc. Natl. Acad. Sci. (USA) Mar. 2001 vol. 98. No. 6 pp. 3460-3465.
Townsend, K.M. et al.; "Genetic Organization of Pasteurella multocida cap Loci and Development of a Multiplex Capsular PCR Typing System"; Journal of Clinical Microbiology; Mar. 2001; vol. 39, No. 3; pp. 924-929.

(56) References Cited

OTHER PUBLICATIONS

Hill, A.L., et al.; "Identification of the Xenopus laevis cDNA for EXT1: A Phylogenetic Perspective"; DNA Sequence, 2002; vol. 13 (2), pp. 85-92; ISSN: 10472-5179; Taylor & Francis Ltd. (USA).

Rimler, R.B.; "Presumptive Identification of Pasteurella multocida serogroups A, D and F by capsule depolymerisation with mucopolysaccharidases"; The Veterinary Record; (1994); vol. 134; pp. 191-192 (USA).

Poggi., et al.; "Inhibition of B16-BL6 Melanoma Lung Colonies by Semisynthetic Sulfaminoheparosan Sulfates from E. coli K5 Polysaccharide"; Seminars in Thrombosis and Hemostasis; (2002); vol. 28(4): 383-392.

Kim, et al.; "Human tumor suppressor EXT gene family members EXTL1 and EXTL3 encode α1 ,4-N-acetylglucosaminyltransferases that likely are involved in heparan sulfate/heparin biosynthesis"; Proc. Natl. Acad. Sci. U.S.A.; Jun. 19, 1998 (13):7176-81.

Vicenzi, et al.; "Broad spectrum inhibition of HIV-1 infection by sulfated K5 Escherichia coli polysaccharide derivatives"; AIDS; Jan. 24, 2003; vol. 17, No. 2; 177-181; ISSN: 0269-9370 Lippincott Williams & Wilkins• Italy.

Lin, X., et al.; "Expression and Functional Analysis of Mouse EXT1, a Homolog of the Human Multiple Exostoses Type 1 Gene"; Biochemical and Biophysical Research Communucations; (1998); vol. 248; pp. 738-743.

Legeai-Mallet L., et al.; "EXT 1 Gene Mutation Induces Chondrocyte Cytoskeletal Abnormalities and Defective Collagen Expression in the Exostoses"; Journal of Bone and Mineral Research; (2000); vol. 15(8): 1489-1500.

McCormick, C., et al.; "The putative tumor suppressor EXT1 alters the expression of cell-surface heparan sulfate"; Nature Genetics; (1998); vol. 19(2):158-161; (Canada).

Ahn, J., et al.; :Cloning of the putative tumor suppressor gene for hereditary multiple exostoses (EXT1); . Nature Genetics (1995); vol. 11(2); pp. 137-143.

Stickens, D., et al.; "The EXT2 multiple exostoses gene defines a family of putative tumour suppressor genes"; Nature Genetics ; (1996); vol. 14(1); pp. 25-32.

Simmons, A.D., et al.; "A direct interaction between EXT proteins and glycosyltransferases is defective in hereditary multple exostoses"; Human Molecular Genetics; (1999); vol. 8(12); pp. 2155-2164. (USA).

Hagner-McWhirter A., et al.; "Biosynthesis of heparin/heparan sulfate: kinetic studies of the glucuronyl C5-epimerase with N-sulfated derivatives of the Escherichia coli K5 capsular polysaccharide as substrates"; Glycobiology; (2000); Vo. 10(2); pp. 159-171; Oxford University Press. (USA).

Lidholt, K., et al.; "Biosynthesis of heparin—The D-glucuronosyl- and N-acetyl-D-glucosaminyltransferase reactions and their relation to polymer modification"; Biochem J. (1992) vol. 287 pp. 21-29; (Sweden).

Lin, X, et al.; "Disruption of Gastrulation and Heparan Sulfate Biosynthesis in EXT1-Deficient Mice"; Developmental Biology; (2000); vol. 224; pp. 299-311; Academic Press. (USA).

Van Hul, W., et al.; "Identification of a Third EXT-like Gene (EXTL3) Belonging to the EXT Gene Family"; Genomics; (1998); vol. 47; pp. 230-237; Academic Press. (Belgium).

Nader, H.B., et al.; "New insights on the specificity of heparin and haparan sulfate lyases from Flavobacterium heparinum revealed by the use of synthetic derivatives of K5 polysaccharide from E. coli and 2-O-desulfated heparin"; Glycoconjugate Journal; (1999); vol. 16; pp. 265-270. Kluwer Academic Publishers Manufactured in The Netherlands.

DeAngelis, P.L., et al.; "Identification and Molecular Cloning of a Heparosan Synthase from Pasteurella multocida Type D*"; The Journal of Biological Chemistry; (2002) vol. 277, No. 9; Issue of Mar. 1; pp. 7209-7213.

Naggi, A., et al.; "Toward a Biotechnological Heparin through Combined Chemical and Enzymatic Modification of the Escherichia coli K5 Polysaccharide"; Seminars in Thrombosis and Hemostasis; vol. 27, No. 5; (2001) pp. 437-443. (Italy).

Leali, D., et al.; "Fibroblast Growth Factor-2 Antagonist Activity and Angiostatic Capacity of Sulfated Escherichia coli K5 Polysaccharide Derivatives*"; The Journal of Biological Chemistry, vol. 276, No. 41. Issue of Oct. 12; pp. 37900-37908; (2001). (Italy).

Duncan, G., et al.; "The link between heparan sulfate and hereditary bone disease: finding a function for the EXT family of putative tumor suppressor proteins"; The Journal of Clinical Investigation; Aug. 2001; vol. 108, No. 4; pp. 511-516. (USA).

Kim, B-T, et al.; "Demonstration of a Novel Gene DEXT3 of Drosophila melanogaster as the Essential N-Acetylglucosamine Transferase in the Heparan Sulfate Biosynthesis"; The Journal of Biological Chemistry; (2002) vol. 277, No. 16; Issue of Apr. 19; pp. 13659-13665. (Sweden).

Sugahara, K., et al.; "Heparin and Heparan Sulfate Biosynthesis"; Life, (2002) vol. 54; pp. 163-175. (Japan).

Lind, T., et al.; "Biosynthesis of Heparin/Heparan Sulfate"; The Journal of Biological Chemistry; (1993); vol. 268, No. 28; Issue of Oct. 5; pp. 20705-20708. (Sweden).

Wei, G., et al.; "Location of the Glucuronosyltransferase Domain in the Heparan Sulfate Copolymerase EXT1 by Analysis of Chinese Hamster Ovary Cell Mutants*"; The Journal of Biological Chemistry; (2000); vol. 275, No. 36 Issu of Sep. 8; pp. 27733-27740. (USA).

Razi, N., et al.; "Structural and functional properties of heparin analogues obtained by chemical sulphation of Escherichia coli K5 capsular polysaccharide"; Biochem J. (1995) vol. 309; pp. 465-472. (Sweden).

Kusche, M., et al.; "Biosynthesis of heparin—Use of Escherichia coli K5 capsular polysaccharide as a model substrate in enzymic polymer-modification reactions"; Biochem J. (1991) vol. 275; pp. 151-158. (Sweden).

Casu, B., et al.; "Heparin-like compounds prepared by chemical modification of capsular polysaccharide from E. coli"; Elsevier Science; Carbohydrate Research (1994) vol. 263; pp. 271-284. (Italy).

Vann, W.F., et al.; "The Structure of the Capsular Polysaccharide (K5 Antigen) of Urinary-Tract-Infective Escherichia coli 010:K5:H4; A Polymer Similar to Desulfo-Heparin"; Eur J. Biochem (1981); vol. 116; pp. 359-364. (Germany).

Toyoda, H., et al.; "Structural Analysis of Glycosaminoglycans in Drosophila and Caenorhabditi elegans and Demonstrations That tout-velu, a Drosophila Gene Related to EXT Tumor Suppressors, Affects Heparan Sulfate in Vivo"; The Journal of Biological Chemistry, (2000); vol. 275, No. 4, Issue of Jan. 28, pp. 2269-2275. (Japan).

Zak, B.M., et al.; "Hereditary multiple exostoses and heparan sulfate polymerization"; Biochimica et Biophysica Acta 1573 (2002); pp. 346-355. (USA).

Katada, T., et al.; "cDNA cloning and distribution of XEXT1, the Xenopus homologue of EXT1"; Dev Genese Evol. (2002); vol. 212; pp. 248-250. (Japan).

Kitagawa, H., et al.; "The Tumor Suppressor EXT-like Gene EXTL2 Encodes an α1, 4-N-Acetylhexosaminylatransferase That Transfers N-Acetylgalactosamine and N-Acetylglucosamine to the Common Glycosaminoglycan-Protein Linkage Region"; The Journal of Biological Chemistry; (1999); vol. 274, No. 20; Issue of May 14; pp. 13933-139337. (USA).

Kitagawa, H., et al.; "rib-2, a Caenorhabditis elegans Homolog of the Human Tumor Suppressor EXT Genes Encodes a Novel α1,4-N-Acetylglucosaminyltransferase Involved in the Biosynthetic Initiation and Elongation of Heparan Sulfate"; The Journal of Biological Chemistry; (2001); vol. 276, No. 7, Issue of Feb. 16; pp. 4834-4838. (Japan).

Song, G., et al.; "Identification of mutations in the human EXT1 and EXT2 genes"; Chin J. Med. Genet; Aug. 1999; vol. 16, No. 4; pp. 208-210. (China).

Clines, G.A., et al.; "The Structure of the Human Multiple Exostoses 2 Gene and Characterization of Homologs in Mouse and Caenorhabditis elegans"; Cold Spring Harbor Laboratory Press 1997; ISSN: 1057-9803 pp. 359-367. (USA).

(56) References Cited

OTHER PUBLICATIONS

Wise, C.A., et al.; "Identification and Localization of the Gene for EXTL, a Third Member of the Multiple Exostoses Gene Family"; Cold Spring Harbor Laboratory Press (1997); ISSN 1054; pp. 9803/97. (USA).

Linhardt, R.J., et al.; "Production and Chemical Processing of Low Molecular Weight Heparins"; Thieme Medical Publishers Inc. (1999); vol. 25, Suppl. 3; pp. 5-16. (USA).

Lind, T., et al.; The Putative Tumor Suppressors EXT1 and EXT2 Are Glycosyltransferases Required for the Biosynthesis of Heparan Sulfate*; The Journal of Biological Chemistry, (1998) vol. 273, No. 41; Issue of Oct. 9, pp. 26265-26268. (Sweden).

Fareed, J.; "Heparin, Its Fractions, Fragments and Derivatives Some Newer Perspectives"; Seminars in Thrombosis and Hemostasis; vol. 11, No. 1; (1985); pp. 1-9.

Senay, C., et al.; "The EXT1/EXT2 tumor suppressors: catalytic activities and role in heparan sulfate biosynthesis"; EMBO Reports; (2000); vol. 1, No. 3; pp. 282-286. (Sweden).

Bio Tie Therapies; BioHeparin—Prospectus; Jun. 2001. (Finland).

Sasisekharan, R., et al.; "Heparin and heparan sulfate: biosynthesis, structure and function"; Elsevier Science, Ltd. Current Opinion in Chemical Biology (2000); vol. 4; pp. 626-631. (USA).

Pedersen, L.C., et al.; "Heparan/Chondroitin Sulfate Biosynthesis—Structure and Mechanism of Human Glucuronyltransferase I*" The Journal of Biological Chemistry; (2000); vol. 275, No. 44; Issue of Nov. 3; pp. 34580-34585. (USA).

Finke, A., et al.; "Biosynthesis of the *Escherichia coli* K5 Polysaccharide, a Representative of Group II Capsular Polysaccharides: Polymerization In Vitro and Characterization of the Product"; Journal of Bacteriology, Jul. 1999; pp. 4088-4094. (Germany).

Griffiths, G., et al.; "Characterization of the Glycosyltransferase Enzyme from the *Escherichia coli* K5 Capsule Gene Cluster and Identification and Charaterization of the Glucuronyl Active Site*"; The Journal of Biological Chemistry; (1998); vol. 273, No. 19; Issue of May 8; pp. 11752-11757. (United Kingdom).

Hodson, N., et al.; "Identification That KfiA, a Protein Essential for the Biosynthesis of the *Escherichia coli* K5 Capsular Polysaccharide, Is an α-UDP-GlcNAc Glycosyltransferase"; The Journal of Biological Chemistry; (2000); vol. 275, No. 35, Issue of Sep. 1; pp. 27311-27315. (United Kingdom).

Townsend, K.M., et al.; "Genetic Organization of Pasteurella multocida cap Loci and Development of a Multiplex Capsular PCR Typing System" Journal of Clinical Microbiology; Mar. 2001; vol. 39, No. 3; pp. 924-929. (Australia).

Boyce, J.D., et al.; "Pasteurella multocida capsule: composition, function and genetics"; Journal of Biotechnology (2000); vol. 83; pp. 153-160. (Australia).

Rimler, R.B., et al.; "Influence of chondroitinase on direct hemagglutination titers and phagocytosis of Pasteurella multocida serogroups A, D and F"; Veterinary Microbiology; vol. 47; (1995); pp. 287-294. (USA).

Rigg, G.P., et al.; "The localization of KpsC, S and T, and KfiA, C and D Proteins Involved in the biosynthesis of the *Escherichia coli* K5 capsular polysaccharide: evidence for a membrane-bound complex"; Microbiology (1998), vol. 144; pp. 2905-2914. (United Kingdom).

DeAngelis, P. L., et al.; "Identification of the capsular polysaccharides of Type D and F Pasteurella multocida as unmodified heparin and chondroitin, respectively"; Carbohydrate Research; (2002); vol. 337; pp. 1547-1552. (USA).

Jing, W., et al.; "Structure function analysis of Pasteurella glycosaminoglycan synthesis"; Glycobiology (2002) 12: abstract 188. (USA).

McCormick, C., et al.: The putative tumor suppressors EXT1And EXT2 form a stable complex that accumulates in the Golgi apparatus and catalyzes the synthesis of heparan sulfate; PNAS, Jan. 18, 2000; vol. 97, No. 2; pp. 668-673. (Canada).

Cheung, P.K., et al.; "Etiological Point Mutations in the Hereditary Multiple Exostoses Gene EXT1: A Functional Analysis of Heparan Sulfate Polymerase Activity"; (2001) Am. J. Hum. Genet. 69:55-66. (Canada).

Wyatt Technology Corporation; "Heparin Characterization" Apr. 5, 1997• www.tigc.org.

Soldani, G., et al.; "Experimental and Clinical Pharmacology of Glycosaminoglycans (GAGs)"; (1991) Drugs Exptl. Clin. Res. XVII(I); pp. 81-85. (Italy).

Van Aken, H., et al. "Anticoagulation: The Present and Future"; Clin. Appl. Thrombosis/Hemostasis; (2001) vol. 7, No. 3; pp. 195-204. (Germany).

Lidholt, K., et al.; "Substrate specificities of glycosyltransferases involved in formation of heparin precursor and *E. coli* K5 capsular polysaccharides"; Carbohydrate Research; (1994); vol. 255; pp. 87-101. (Sweden).

Roberts, I., et al.; "Molecular Cloning and Analysis of Genes for Production of K5, K7, K12, and K92 Capsular Polysaccharides in *Escherichia coli*"; Journal of Bacteriology; Dec. 1986; vol. 168, No. 3; pp. 1228-1233. (Germany).

Kroncke, K.D., et al.; "Expression of the *Escherichia coli* K5 Capsular Antigen: Immunoelectron Microscopic and Biochemical Studies with Recombinant *E. coli*"; Journal of Bacteriology; Feb. 1990; vol. 172, No. 2; pp. 1085-1091. (Germany).

Roberts, I.S., et al.; "Common Organization of Gene Clusters for Production of Different Capsular Polysaccharides (K Antigens) in *Escherichia coli*"; Journal of Bacteriology; Mar. 1988; vol. 170, No. 3; pp. 1305-1310. (United Kingdom).

Petit, C., et al.; "Region 2 of the *Escherichia coli* K5 capsule gene cluster encoding proteins for the biosynthesis of the K5 polysaccharide"; Molecular Microbiology (1995); vol. 17, No. 4; pp. 611-620. (United Kingdom).

Smith, A.N., et al.; "Molecular analysis of the *Escherichia coli* K5 kps locus: identification and characterization of an inner-membrane capsular polysaccharide transport system"; Molecular Microbiology (1990); vol. 4, No. 11; pp. 1863-1869. (United Kingdom).

Bronner, D., et al.; "Synthesis of the K5 (group II) capsular polysaccharide in transport-deficient recombinant *Escherichia coli*"; FEMS Microbiology Letters 113; (1993); pp. 273-284. (Germany).

Pandit, K.K., et al.; "Capsular hyaluronic acid in Pasteurella multocida type A and its counterpart in type D"; Research in Veterinary Science; (1993); vol. 54; pp. 20-24.

Linhardt, R.J. et al.; "Isolation and characterization of human heparin"; Biochemistry, vol. 31, No. 49; pp. 12441-12445 (1992).

DeAngelis, P.; "Microbial glycosaminoglycan glycosyltransferases"; Glysobiology, (2002); vol. 12, No. 1; pp. 9R-16R.

Sismey-Ragatz, et al.; "Chemoenzymatic Synthesis with Distinct Pasteurella Heparosan Synthases: Monodisperse Polymers and Unnatural Structures"; Journal of Biological Chemistry, vol. 282, No. 39; pp. 28321-28327, XP0551 16675, ISSN: 0021-9258, DOI: 10.1 074/jbc.M701 599200.

Kiyoshi Suzuki et al.; "Generation and characterization of a series of monoclonal antibodies that specifically recognize [HexA(±2S)-GlcNAc]n epitopes in heparan sulfate", Glycoconjugate Journal (2008); vol. 25; pp. 703-712; DOI: 10.1007/s10719-008-9130-Z.

Kuberan et al., "Analysis of Heparan Sulfate Oligosaccharides with Ion Pair-Reverse Phase Capillary High Performance Liquid Chromatography-Microelectrospray Ionization Time-of-Flight Mass Spectrometry"; (2002); vol. 124 pp. 8708-8718.

U.S. Appl. No. 14/536,003; Paul DeAngelis; filed Nov. 7, 2014; Not Yet Published.

Extended European Search Report, dated Oct. 11, 2014; in EP Application No. 09813350.7; filed Apr. 8, 2011.

U.S. Appl. No. 13/325,181, Paul DeAngelis, Office Action, dated Dec. 26, 2014.

U.S. Appl. No. 12/556,324, Paul DeAngelis, Office Action, dated Nov. 25, 2014.

U.S. Appl. No. 14/607,893; Paul DeAngelis, filed Jan. 28, 2015. Not Yet Published.

International Search Report, dated Jan. 28, 2016, in PCT/US2015/57198, filed Oct. 23, 2015.

(56) References Cited

OTHER PUBLICATIONS

Written Opinion of the International Searching Authority, dated Jan. 28, 2016, in PCT/US2015/57198, filed Oct. 23, 2015.
U.S. Appl. No. 12/556,324; Paul L. DeAngelis, Office Action dated May 4, 2016.
Remington: The Science and Practice of Pharmacy, Nineteenth Edition (1995), pp. 1463, 1546-1547.
English machine translation of JP2004-018840 above, downloaded from European Patent Office on May 19, 2015.
U.S. Appl. No. 13/325,181; Paul L. DeAngelis; Final Office Action dated May 28, 2015.
U.S. Appl. No. 12/556,324; Paul L. DeAngelis; Office Action dated Jun. 10, 2015.
U.S. Appl. No. 14/060,077; Paul L. DeAngelis, Office Action dated Aug. 26, 2015.

* cited by examiner

US 9,925,209 B2

HEPAROSAN-POLYPEPTIDE AND HEPAROSAN-POLYNUCLEOTIDE DRUG CONJUGATES AND METHODS OF MAKING AND USING SAME

CROSS REFERENCE TO RELATED APPLICATIONS/INCORPORATION BY REFERENCE STATEMENT

The present application claims benefit under 35 USC § 119(e) of U.S. Ser. No. 61/901,309, filed Nov. 7, 2013. This application is also a continuation-in-part of U.S. Ser. No. 13/715,117, filed Dec. 14, 2014; which is a divisional of U.S. Ser. No. 12/556,324, filed Sep. 9, 2009. The '324 application claims benefit under 35 USC § 119(e) of U.S. Ser. No. 61/179,275, filed May 18, 2009. In addition, the '324 application is also a continuation-in-part of U.S. Ser. No. 12/383,046, filed Mar. 19, 2009, now abandoned; which claims benefit under 35 USC § 119(e) of U.S. Ser. No. 61/095,572, filed Sep. 9, 2008; and U.S. Ser. No. 61/038,027, filed Mar. 19, 2008. The entire contents of the above-referenced patent applications are hereby expressly incorporated herein by reference.

STATEMENT REGARDING FEDERALLY SPONSORED RESEARCH OR DEVELOPMENT

This invention was made with government support under Contract Number MCB9876193 awarded by the National Science Foundation and under Grant No. 1 R43CA159494-01 awarded by a National Institute of Health (NIH) Small Business Innovation Research (SBIR) grant. The government has certain rights in the invention.

BACKGROUND

A wide range of existing and near-term therapeutics has great potential, but many of these agents possess drawbacks that slow or prevent implementation for aiding human health. For example, many therapeutics, drugs, or drug candidates have issues with delivery due to non-optimal pharmacokinetics and/or detrimental side effects due to their non-human nature. Injectable biologic drugs are one class that often needs assistance and includes molecules such as polypeptides (e.g., peptides, proteins) and polynucleotides (e.g., DNA, RNA, nucleic acid-polypeptide hybrids).

In particular, polypeptides (e.g., peptides, proteins, glycoproteins, etc.) or polynucleotides (e.g., polymers comprised of deoxyribonucleic acid or ribonucleic acids or nucleic acid-polypeptide hybrids, etc.) with therapeutic activity, often termed biologics, are becoming an ever increasingly useful type of modern medicine. However, these therapeutic agents may have problems due to short plasma half-life and/or negative effects with the body's systems.

Fortunately, the physical, chemical, and/or biological nature of a promising drug candidate may sometimes be assisted by modifying the parental drug. A widely used agent, poly[ethylene glycol] (PEG) has been approved by the Food and Drug Administration (FDA) for use with therapeutic "cargo" including small molecule drugs, polypeptides, and liposomes, for example. Covalent modification with a poly(ethylene glycol) [PEG] vehicle, called PEGylation, was one of the early attempts to rectify these issues with success, resulting in multiple FDA-approved drugs. The hydrophilic chains of PEG polymers increase the solubility of the cargo in water, protect the cargo when in the human body, and prolong the therapeutic action of the cargo. For example, PEGylation can shield the drug cargo molecule's surface from antibodies, regulatory enzymes, and/or clearance receptors. In addition, PEGylation can also increase the hydrodynamic size of the cargo, thereby preventing rapid elimination through renal filtration, which is especially important for therapeutics less than approximately about 60 to about 70 kDa.

However, PEG has some liabilities as a conjugating vehicle, including but not limited to, a lack of a safe degradation pathway, accumulation in some tissues, emerging immunogenicity, and potential triggering of the complement system. Due to its artificial nature, its chemical synthesis, and its potential harmful effects when ingested in large quantities over long periods of time, the use of PEG has significant drawbacks, and alternatives have been sought.

Therefore, other polymers have been experimentally employed as substitutes for PEG. Some of the promising candidates have been carbohydrates due to their perceived improved safety including modified starch (e.g. hydroxyethyl starch [HES]) and poly(sialic acid) [PSA] (see Table 1 below)). In a similar vein, genetic fusion of stretches of hydrophilic amino acid residues to protein cargo has also been employed, but this approach is applicable to a more limited subset of drugs (i.e., only human proteins).

Therefore, alternative modifying and/or coupling agents that can be used with drug cargo, and in particular polypeptides and polynucleotides, and which overcome the defects and disadvantages of the prior art, are continually being sought.

DETAILED DESCRIPTION

Figure 1:
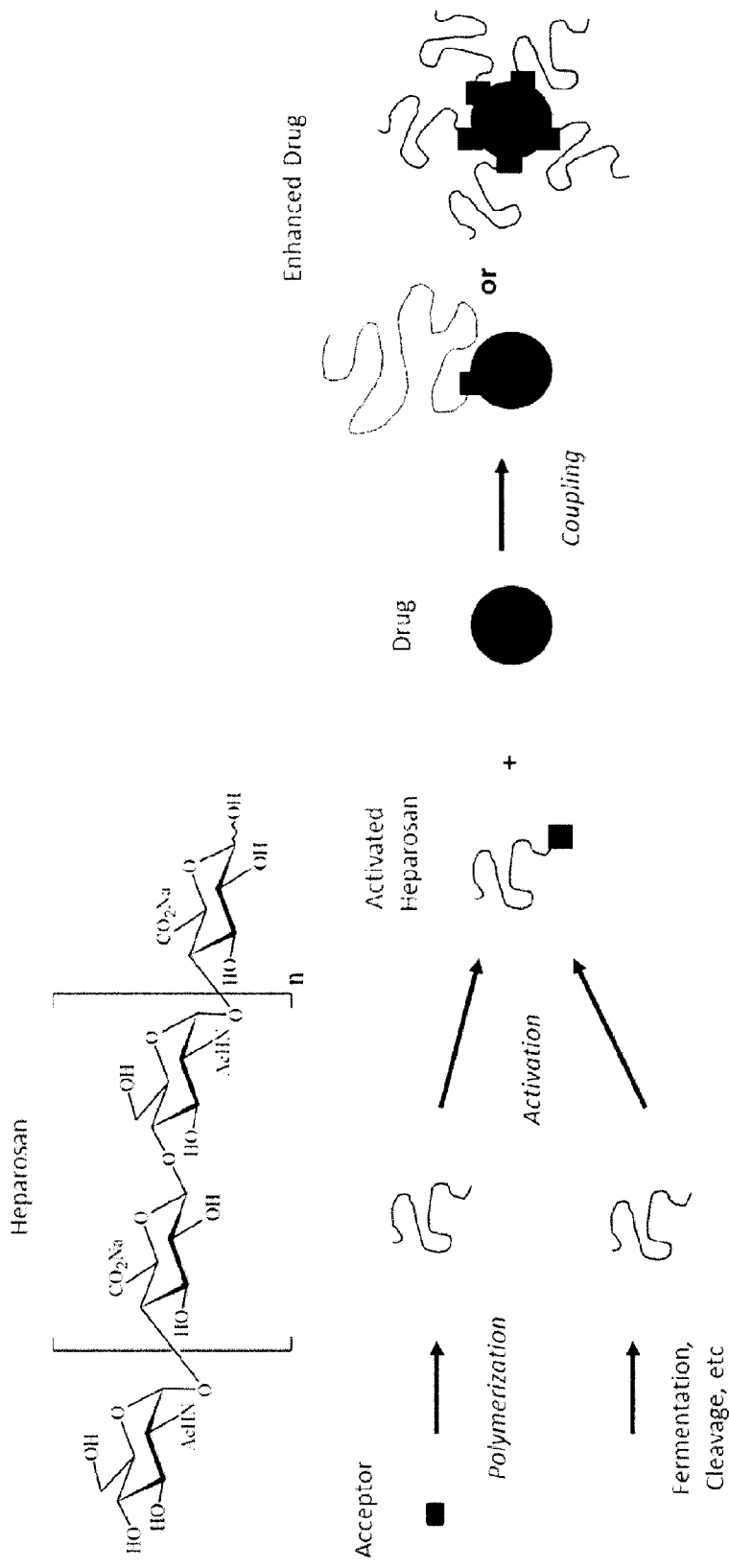
FIG. 1 depicts the general strategy for adding the heparosan vehicle to a therapeutic. Heparosan (HEP) polymer may be derived from methods including: (i) chemoenzymatic polymerization in vitro (upper path) or (ii) microbial fermentation in vivo (lower path). Chemical transformation or activation of the heparosan into different reactive species suitable for conjugation to drugs or drug candidates, depending on the chemical group(s) employed, can be done at various steps (e.g., modification of the acceptor pre-polymerization, or post-polymerization, or a combination of both, as well as during the polymer fragmentation steps, etc.), and this diagram simply depicts a few, non-limiting examples. One or multiple heparosan chains can be added to the drug or drug candidate as desired, depending on the chemistry employed, the activated heparosan, and the drug target.

Before explaining at least one embodiment of the presently disclosed and/or claimed concept(s) in detail, it is to be understood that the presently disclosed and/or claimed concept(s) is not limited in its application to the details of construction and the arrangement of the components or steps or methodologies set forth in the following description or illustrated in the drawings. The presently disclosed and/or claimed concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those of ordinary skill in the art to which this presently disclosed and/or claimed concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions/complexes, kits, and/or methods disclosed or otherwise contemplated herein can be made and executed without undue experimentation in light of the present disclosure. While the compositions/complexes, kits, and methods of the presently disclosed and/or claimed inventive concept(s) have been described in terms of particular embodiments, it will be apparent to those of ordinary skill in the art that variations may be applied to the compositions/complexes, kits, and/or methods as well as in the steps and/or in the sequence of steps of the methods described herein without departing from the concept, spirit, and scope of the presently disclosed and/or claimed inventive concept(s). All such similar substitutes and modifications apparent to those of ordinary skill in the art are deemed to be within the spirit, scope, and concept of the presently disclosed and/or claimed inventive concept(s).

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, and/or CAB. Continuing with this example, expressly included are combinations that contain repeats of one or more item or term, such as BB, AAA, AAB, BBC, AAABCCCC, CBBAAA, CABABB, and so forth. One of ordinary skill in the art will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "heparosan" as used herein will be understood to refer to a carbohydrate chain with a repeat structure of ([-4-N-acetylglucosamine-$\alpha$1,4-glucuronic acid-$\beta$1-]$_n$), wherein n is 1 or greater. In certain non-limiting examples, n may be from about 2 to about 5,000. The term "oligosaccharide" generally denotes n being from about 1 to about 11, while the term "polysaccharide" denotes n being equal to or greater than 12. The term "heparosan" may be utilized interchangeably with the terms "N-acetylheparosan" and "unsulfated, unepimerized heparin."

The term "UDP-sugar" as used herein refers to a carbohydrate modified with uridine diphosphate (e.g., UDP-N-acetylglucosamine).

The term "polypeptide" as used herein will be understood to refer to a polymer of amino acids. The polymer may include d-, l-, or artificial variants of amino acids. In addition, the term "polypeptide" will be understood to include peptides, proteins, and glycoproteins.

The term "polynucleotide" as used herein will be understood to refer to a polymer of nucleotides. Nucleotides, as used herein, will be understood to include deoxyribose nucleotides and/or ribose nucleotides, as well as artificial variants thereof.

The term "analog" as used herein will be understood to refer to a variation of the normal or standard form or the wild-type form of molecules. For polypeptides or polynucleotides, an analog may be a variant (polymorphism), a mutant, and/or a naturally or artificially chemically modified version of the wild-type polynucleotide (including combinations of the above). Such analogs may have higher, full, intermediate, or lower activity than the normal form of the molecule, or no activity at all; in the latter case, these drugs can often act as bait or blockers of activity. Alternatively and/or in addition thereto, for a chemical, an analog may be any structure that has the functionalities (including alterations or substitutions in the core moiety) desired, even if comprised of different atoms or isomeric arrangements.

The term "conjugate" as used herein refers to a complex created between two or more compounds by covalent or weak bonds. The term "covalent" as used herein refers to the sharing of electrons between atoms to create a chemical interaction.

The term "cargo" as used herein refers to the drug, therapeutic, or other biologically active component in the conjugate, while the term "vehicle" as used herein refers to the carrier of the cargo (e.g., the heparosan polymer) in the conjugate.

As used herein, the term "active agent(s)," "active ingredient(s)," "pharmaceutical ingredient(s)," "therapeutic," "medicant," "medicine," "biologically active compound" and "bioactive agent(s)" are defined as drugs and/or pharmaceutically active ingredients.

The term "Dalton" (Da) as used herein will be understood to refer to a unit of molecular mass for polypeptides and polysaccharides. The term "kiloDalton" (kDa) as used herein refers to one thousand Daltons. The term "megaDalton" (MDa) as used herein will be understood to refer to one million Daltons (i.e., one thousand kDa).

The term "polydispersity" as used herein refers to a measure of the width of molecular weight distributions of a product. In one, non-limiting example, polydispersity is calculated by dividing the Weight average molar mass (Mw) by the Number average molar mass (Mn); thus, polydispersity=Mw/Mn.

The terms "quasi-monodisperse" and "substantially monodisperse" are used herein interchangeably and will be understood to refer to very narrow size distributions approaching the ideal polydispersity value of 1.

The term "PEGylation" as used herein refers to the modification of a drug or drug candidate molecule by addition of polyethylene glycol thereto.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule/composition can be biologically active through its own functionalities, or may be biologically active based on its ability to activate, modulate, or inhibit molecules/compositions having their own biological activity. In addition, biological activity observed in in vitro proxy models is indicative of in vivo action of a molecule/composition.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" as used herein includes human and veterinary subjects. "Mammal" for purposes of treatment refers to any animal classified as a mammal, including human, domestic and farm animals, nonhuman primates, and any other animal that has mammary tissue.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, prevention, or management of a disease and/or condition. The specific amount that is therapeutically effective can be readily determined by the ordinary medical practitioner, and can vary depending on factors known in the art, such as the type of disease/cancer, the patient's history and age, the stage of disease/cancer, and the co-administration of other agents.

A "disorder" is any condition that would benefit from treatment with the compositions disclosed herein. This includes chronic and acute disorders or diseases including those pathological conditions which predispose the mammal to the disorder in question.

The term "effective amount" refers to an amount of a biologically active molecule or complex or derivative thereof sufficient to exhibit a detectable therapeutic effect without undue adverse side effects (such as toxicity, irritation and allergic response) commensurate with a reasonable benefit/risk ratio when used in the manner of the inventive concept(s). The therapeutic effect may include, for example but not by way of limitation, inhibiting the growth of microbes and/or opportunistic infections. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The terms "administration" and "administering," as used herein will be understood to include all routes of administration known in the art, including but not limited to, oral, topical, transdermal, parenteral, subcutaneous, intranasal, mucosal, intramuscular, intraperitoneal, intravitreal, and intravenous routes, including both local and systemic applications. In addition, the compositions of the presently disclosed and/or claimed inventive concept(s) (and/or the methods of administration of same) may be designed to provide delayed, controlled or sustained release using formulation techniques which are well known in the art.

The following abbreviations, which may be utilized herein, will be understood to refer the following terms or phrases: Human Growth Hormone [hGH]; Phenylalanine Ammonia-Lyase [PAL]; L-Asparaginase [Asp]; Strong anion exchange chromatography [SAX]; PolyAcrylamide Gel Electrophoresis [PAGE]; Sodium Dodecyl Sulfate-PolyAcrylamide Gel Electrophoresis [SDS-PAGE]; trifluoroacetic acid [TFA]; Deoxyribonucleic acid [DNA]; Ribonucleic acid [RNA]; Poly(ethylene Glycol) [PEG]; Hydroxyethylstarch [HES]; Poly(sialic acid) [PSA]; Uridine diphosphate [UDP]; Heparan Sulfate [HS]; Granulocyte colony stimulating factor [G-CSF]; Glucagon-like peptide-1 [GLP-1]; Interferon [INF]; Dalton [Da]; Kilodalton [kDa]; Molecular Weight [MW]; Molar [M]; Gram [g]; Kilogram [kg]; Milligram [mg]; Microgram [μg or ug]; Nanogram [ng]; Volt [V]; Bovine Serum Albumin [BSA]; Recombinant human granulocyte colony stimulating factor [rH-G-CSF]; High Performance Liquid Chromatography-Size Exclusion Chromatography [HPLC-SEC].

Turning now to the presently disclosed and/or claimed inventive concept(s), embodiments thereof relate in general to the field of the therapeutic drugs or drug candidates, which include polypeptides, proteins, peptides, and polynucleotides chemically conjugated to heparosan (HEP) ([-4-N-acetylglucosamine-α1,4-glucuronic acid-β1-]$_n$) polysaccharide vehicles. Conjugation of proteins, peptides, and polynucleotides (for example but not by way of limitation) to heparosans are demonstrated herein using various coupling chemistries linking target group(s) on the drug cargo to group(s) on the heparosan vehicle(s). Various sizes of quasi-monodisperse heparosans were coupled to the polypeptides and polynucleotides. The resulting HEP-drug conjugates (i.e., heparosan covalently bound to polypeptides or polynucleotides) were detected via electrophoresis and/or chromatographic methods. The HEP-drug conjugates retained biological activity in various in vivo and in vitro biological assays.

The addition of one or more heparosan carbohydrate chains to drugs or drug candidates to produce drug-conjugates possesses several benefits over the prior art, including but not limited to, increasing the hydrodynamic size of the drug. In addition, coating one or multiple areas of the drug surface with heparosan provides protection from proteases, regulatory factors, and from clearing mechanisms (e.g., renal filtration, specific receptor clearance, etc.). Further, even if the addition of heparosan vehicle were to reduce the in vitro activity of the drug (e.g., due to steric hindrance or blocking), when in the mammalian body in vivo, the HEP-drug conjugate can have altered, improved pharmacokinetics compared to the unmodified drug (e.g., longer half-life, increased area under the curve pharmacokinetics, protection from removal by the immune system, etc.) that would counteract any reduction in activity observed in vitro.

As discussed herein above, the pharma industry has employed a variety of drug delivery strategies, and the presently disclosed and/or claimed inventive concept(s) focuses on drug-polymer conjugates, in particular those utilizing a newly introduced system using a natural carbohydrate called heparosan ([-4-N-acetylglucosamine-α1,4-glucuronic acid-β1-]$_n$). This molecule, the biosynthetic precursor to the well-known drug heparin and to the widespread glyco-moiety heparin sulfate (HS) in the body, appears tolerated due to its 'self' nature as well as its intrinsically favorable behavior in the bloodstream and tissues. The polysaccharide is stable in the extracellular spaces of mammals, but degraded by lysosomal enzymes following entry into the cell. Heparosan is predicted to serve as a conjugating vehicle to extend the plasma half-life of biologics without liabilities of polydispersity, immunogenicity, and/or unwanted accumulation in the body that are observed for other types of polymers, such as but not limited to, poly (ethylene glycol), hydroxyethyl starch, or poly(sialic acid).

Heparosan ([-4-N-acetylglucosamine-α1,4-glucuronic acid-β1-1-]$_n$) is a natural polysaccharide related to heparin, one of the most widely used drugs in the pharmacopeia. From a chemophysical standpoint, the heparosan chain is very hydrophilic due its two hydroxyl groups on every monosaccharide unit and a negative carboxylate group on every other monosaccharide unit (FIG. 1). Heparosan should be biocompatible in the human body because it is the endogenous natural precursor in the heparin/heparan sulfate (HS) biosynthetic pathway (Sugahara et al. (2002) *IUBMB Life*, 54(4):163-175). Stretches of heparosan exist in the HS chains found on virtually every human cell; thus, it is not perceived as a foreign molecule. Certain pathogenic bacteria even exploit the "self" nature of heparosan by using a heparosan coating or capsule to evade the immune system during infection. In the pre-genomic era, the difficulty in raising antibodies to heparosan for use as 'typing sera' is exemplified by the need to use either a capsule-specific bacteriophage (a virus) or bacterial heparin-degrading enzymes to make these microbial identifications.

In contrast to HS and heparin, the heparosan molecule is neither decorated with sulfate groups nor epimerized at glucuronic acid residues; thus, heparosan is biologically inactive to a significant extent with respect to coagulation (i.e., clotting factors not activated to a significant extent), modulation of proliferation (i.e., growth factors do not bind to a significant extent), inflammation (i.e., cytokines do not interact to a significant extent), and a plethora of other activities (Capila et al. (2002) *Angew Chem Int Ed Engl*, 41(3):391-412). Furthermore, enzymes that degrade (heparanase) or receptors that clear HS from the bloodstream (Hyaluronan Receptor for Endocytosis (HARE) or stabilin) do not recognize heparosan to a significant extent, because the sulfate groups essential for activity are absent from this polymer (Pikas et al. (1998) *J. Biol. Chem.*, 273(30):18770-18777; and Harris et al. (2008) *Glycobiology*, 18(8):638-648). In other words, heparosan reads as 'a hole in the sugar code' that is ignored or not significantly affected by the HS recognition systems. Therefore, heparosan is stable in the extracellular spaces where many therapeutic drugs act. Over time, bulk cellular fluid uptake or pinocytosis will internalize heparosan, but once the polymer arrives at the lysosome, the normal degradation pathway for HS/heparin removes sugars from the non-reducing end in a sequential fashion. In contrast, PEG is not degraded in such a fashion; larger PEG is particularly long lasting in the body; thus, most PEGylation reagents are in the 5- to 40-kDa range (much smaller than the largest HEP reagents possible) to avoid accumulation in the tissues. Similarly, HES reagents are usually below 70 kDa.

TABLE 1

Characteristics of Drug Delivery Systems
The various vehicles have different production methods, purity, and biological behavior in the body. The ideal delivery agent should have a "Yes" response in all critical categories below.

| Vehicle | Quasi-Monodisperse? | Biodegradable? | Not Immunogenic? |
| --- | --- | --- | --- |
| PEG | Yes | No | Sometimes |
| Heparosan | Yes | Yes | Yes |
| HES | No | Yes | Yes |
| PSA | No | Yes | Sometimes |
| Fusion | Yes | Yes | No* |

(PEG = poly(ethylene glycol); HES = hydroxyethylstarch; PSA = poly(sialic acid); Fusion = fusion peptide composed of hydrophilic amino acids added by molecular genetic means to the cargo protein; quasi-monodisperse [i.e., very narrow size distributions approaching the ideal polydispersity value of 1])
*In theory, antibody production against any non-human polypeptide sequence is a possibility.

The theoretical predictions for the behavior of heparosan in the body have been borne out by various experimental tests in rodents and primates (U.S. Published Patent Application No. 2010/0036001, published to DeAngelis on Feb. 11, 2010; the entire contents of which are hereby expressly incorporated herein by reference). The molecule has about a 0.5-day to 8-day half-life in the bloodstream, depending on its molecular weight and the route of injection. The polymer chain length is stable in plasma. No significant accumulation in tissues was observed. Over time the metabolites of the probe linker with short sugar chain are excreted in urine and feces. The polymer does not cross the blood-brain barrier to a significant extent, which may be important for ensuring the safety of some therapeutics. No detrimental toxicological effects were observed with acute doses of 100 milligram per kilogram (mg/kg) in a rodent model.

A variety of biologics have been modified with heparosan herein (schematically depicted in FIG. 1) with retention of sufficient activity and improvement of pharmacokinetics. As observed in the case of PEG-drug conjugates, the nature of the cargo molecule can potentially affect the behavior of heparosan-drug conjugates. In some conjugates, the drug is cleared or inactivated by efficient mechanisms (e.g., receptor-based or protease-mediated) that may shorten the observed half-life more than the prediction based solely on the heparosan vehicle alone, while in other conjugates, the cargo assumes the longer half-life of the vehicle.

Most of the typical chemistries used to modify molecules with PEG are amenable to use with heparosan. For example, reactive heparosan polymers with a single amine-reactive (e.g., aldehyde), sulfhydryl-reactive (e.g., maleimide, iodoacetyl), or carbonyl-reactive (e.g., amine) functionality at the reducing terminus have been conjugated to polypeptides and to polynucleotides. This listing of chemical coupling methods to produce conjugates is not exhaustive; the spirit of the presently disclosed and/or claimed inventive concept(s) includes any conjugate made by covalently bonding heparosan polymer(s) to a therapeutic or a drug candidate. Based on testing in parallel, the coupling efficiencies of heparosan-based reagents are comparable to PEG-based reagents; typically the limiting factor in the formation of the conjugate is the intrinsic stability and properties of the drug cargo itself. In addition to adding a single heparosan polymer to a polypeptide or an aptamer, certain embodiments of the presently disclosed and/or claimed inventive concept(s) also cover the addition of two or more heparosan chains (FIG. 1). In this latter embodiment, more of the surface of cargo is covered, masked, or cloaked with heparosan chains; for non-human molecules and especially non-mammalian molecules (foreign), this topology helps protect the drug or drug candidate from being recognized by the immune system or preventing antibody attachment if an immune response was already initiated. In addition to the conjugation of a single, linear chain heparosan moiety to a site on the drug or drug candidate, the presently disclosed and/or claimed inventive concept(s) also covers other geometries (e.g., branched with more than 1 chain at an attachment site, or star or dendritic geometries) of heparosan arrangements. The basic inventive concept is the covalent addition of HEP to the drug or drug candidate to enhance therapeutic performance in the body and improve patient well-being.

In addition to the 'biological' issues surrounding the drug's behavior in the body, the polymer should also be amenable to facilitate manufacture and quality control. Therefore, the polymer size distribution (polydispersity) should be narrow such that the final drug will have uniform effectiveness. In addition, the efficiency of coupling to the drug should be as high as possible; in one particular case, at least about 25% to about 100% of the drug or drug candidate should be modified in a coupling reaction, and in another particular case, about 80% to about 100%. PEG, with a longer history of use and simpler chemical synthesis, has addressed the issues of polydispersity and activation to a large degree, but the HES and PSA carbohydrate systems are still somewhat lacking in these regards.

From a manufacturing perspective, mammalian HS or heparin is not the ideal starting material for heparosan because chemical transformation by desulfation is problematic and will always result in damaged backbone chains and/or residual sulfate groups. In addition, animal-derived materials are not perceived favorably by drug regulatory agencies due to the potential risk of contamination by adventitious agents (e.g., prions, virus, etc.). The human enzymes that form heparosan by polymerizing the uridine diphospho-sugar (UDP-sugar) precursors in the HS biosynthetic pathway are also non-ideal; they are weakly expressed in recombinant systems and are poor catalysts in vitro. Fortunately, certain pathogenic bacteria possess very useful enzymes that produce heparosan (DeAngelis (2002) *Glycobiology*, 12(1):9R-16R). One such enzyme, PmHS1, the heparosan synthase from *Pasteurella multocida*, is very active and stable in recombinant forms (including fusion proteins, truncations, mutants, or analogs and combinations thereof). In addition, PmHS2 or chimeric recombinant enzyme versions combining the activities of PmHS1 and PmHS2 can be used with varying levels of efficiency.

In one embodiment, heparosan manufacture utilizes a novel synchronized, stoichiometrically-controlled reaction employing a sugar-polymerizing enzyme (e.g., PmHS1 or PmHS2 and combinations thereof or similar analogs with roughly equivalent biological activity) in an aqueous buffer system that results in a quasi-monodisperse (very narrow size distribution) product. The heparosan synthase can be utilized in vitro to synthesize quasi-monodisperse (i.e., very narrow size distributions approaching the ideal polydispersity value of '1') polymer preparations (Sismey-Ragatz et al. (2007) J. Biol. Chem., 282(39):28321-28327) with homogenous reactive end-groups for coupling to biologic targets. The narrow size distribution is achieved by synchronizing the polymerization reaction using a primer, a short heparosan fragment, which allows the normal slow chain initiation step of biosynthesis to be bypassed. Therefore, all polymers are rapidly extended by PmHS1 in a virtually parallel fashion; thus, all final chains have a very similar length. No post-polymerization purification for size control is required. The primer also contributes the unique reactive group(s) that helps assure that every polymer chain can be activated for drug coupling. In addition, the primer position in the heparosan chain at the reducing terminus does not interfere with lysosomal degradation allowing the heparosan chain to be digested to a tiny stub containing the linker site used for drug attachment; this stub is usually excreted in the urine or feces.

The chain size or molecular weight of any particular heparosan preparation is controlled by manipulating the stoichiometric ratio of the primer to the UDP-sugar precursor. Basically, for a given amount of UDP-sugars, a low concentration of primer yields longer chains while, on the other hand, a high primer concentration yields shorter chains (of course, the former case has fewer moles of product formed than the latter). Heparosan molecules in the range of from about 10 kDa to about 4,500 kDa (or from about 50 to about 22,500 monosaccharide units) have been synthesized by the synchronized chemoenzymatic method, thus potentially accessing a wider useful size range than possible for PSA, HES, or PEG. By using other methods such as step-wise synthesis (elongation with a pair of PmHS1 mutants) or chemical fragmentation, heparosan polymers from about 600 Da to about 100 kDa can be made.

The heparosan chemoenzymatic process has been run at the 150-gram level while retaining the same polydispersity values (about 1.003 to about 1.2, depending on chain size) as observed in the milligram level syntheses (Sismey-Ragatz et al. (2007) *J. Biol. Chem.,* 282(39):28321-28327); thus, scaling to the kilogram production level by this method is predicted. The polymer uniformity facilitates production and quality control aspects essential for drug approval. Typical polydispersity values in a range of from about 1.0 to about 1.1.

In addition to in vitro chemoenzymatically produced heparosan, the same [-4-N-acetylglucosamine-α1,4-glucuronic acid-β1-]$_n$ polymeric structure may also be produced in vivo by the culture or fermentation of certain microbes, but the polymer may not be as monodisperse or as easily activated for coupling in comparison to the in vitro produced polymer. Some examples of the fermentation systems include natural heparosan producers including *Pasteurella multocida* or allies (e.g., *Avibacterium* species), *Escherichia coli* K5, or the recombinant versions (e.g., Gram − or Gram + bacteria, Achaea, or eukaryotic hosts) expressing the heparosan biosynthetic machinery (e.g., synthases or polymerases or glycosyltransferases, UDP-glucose dehydrogenases, etc.) of the natural heparosan-producing species. The microbial heparosan production route may be used to make polymer for preparation of HEP-drug conjugates, and is covered by the spirit and scope of the presently disclosed and/or claimed inventive concept(s); the source of heparosan polymer is not important for the enhancement of therapeutic efficacy.

Heparosan meets the criteria for a desirable drug delivery vehicle on multiple fronts. From an intrinsic point of view, heparosan has a ~500 million year safety profile; all animals from hydras to human synthesize and display HS (with its endogenous stretches of heparosan) on their cell surface. In the simplest embodiment of modification of proteins, the geometry of attachment to cargo is also identical to the natural proteoglycans (heparin sulfate post-translationally modified glycoproteins) where the reducing end of the heparosan chain(s) is attached to the polypeptide chain.

Furthermore, metazoan cells intracellularly metabolize heparosan along with heparan sulfate and heparin; the chain is degraded from the non-reducing end. Therefore, in the simplest embodiment of the heparosan-based technology, after lysosomal processing only a short stub composed of the synthetic linker (the attachment site to cargo) and 1-3 monosaccharides that is excreted from the body in a similar fashion to the pathways for many small molecular weight drugs, hormones, and hydrophobic molecules. This scenario is a major improvement over PEG where the lack of a natural degradation and excretion pathway contributes to accumulation of the unnatural polymer in tissues.

As stated herein above, the addition of heparosan (HEP) to a therapeutic cargo molecule is superior to PEGylation because: a) a larger size range of heparosan polymers is more readily synthesized than PEG; b) the size distribution at longer chain lengths of heparosan can be controlled more carefully than PEG; c) heparosan has a higher water solubility than PEG; d) as a naturally occurring polysaccharide, heparosan's degradation products are biocompatible; and e) heparosan is not immunogenic.

In humans, polymers of heparosan only exist transiently, serving as a precursor to the more highly modified final products of heparan sulfate and heparin. The bacterial-derived enzymes used to produce heparosan for use in one embodiment of the presently disclosed and/or claimed inventive concept(s) synthesize heparosan as their final product. A single polypeptide, the heparosan synthase PmHS1 of *Pasteurella multocida* Type D, polymerizes the heparosan sugar chain by transferring both GlcUA and GlcNAc. PmHS1 is a robust enzyme that efficiently makes polymers up to approximately about 4.5 MDa (i.e., about 4,500 kDa or about 22,000 monosaccharide units) in vitro. In *Escherichia coli* K5, at least two enzymes, KfiA, the alpha-GlcNAc transferase, and KfiC, the beta-GlcUA-transferase, (and perhaps KfiB, a protein of unknown function) work in concert to form the disaccharide repeat of heparosan. The *E. coli* enzyme complex is not as efficient as the PmHS1 enzyme, as it is more difficult to produce the long polymer chains with the *E. coli* enzyme complex. However, for the purpose of the presently disclosed and/or claimed inventive concept(s), it is intended and will be understood that any method which produces heparosan falls within the scope of the presently disclosed and/or claimed inventive concept(s). It is not the method of producing heparosan that is determinative—rather, it is the conjugation of heparosan from any source or method of production (e.g., fermented heparosan produced by native or recombinant microbes, as well as chemoenzymatic syntheses or organic chemical syntheses) to a target molecule (i.e., the cargo) for increased solubility in water, bioavailability and dwell time within the patient that is presently disclosed and/or claimed.

A key advantage to using heparosan is that it has increased biostability in the extracellular matrix when compared to other GAGs such as hyaluronic acid and chondroitin. As with most compounds synthesized in the body, new molecules are typically made, and after serving their purpose, are broken down into smaller constituents for recycling.

Heparin and heparan sulfate, for example, are degraded by a single enzyme known as heparanase. Experimental challenge of heparosan and N-sulfo-heparosan with heparanase, however, shows that since these polymers lack the 0-sulfation of heparin and heparan sulfate, heparosan and N-sulfo-heparosan are not sensitive to enzymatic action in vitro by heparanase. These findings indicate that heparosan is not fragmented enzymatically in the body, thereby indicating that heparosan is a stable biomaterial for use as a drug conjugate.

However, if heparosan or any of its fragments (generated by reactive oxygen species, etc.) is internalized into the lysosome, then the molecules will be degraded by resident beta-glucosidase and alpha-hexosaminidase enzymes (which remove one sugar at a time from the non-reducing termini of the GAG chain), similar to the degradation of heparin or hyaluronic acid. Therefore, the heparosan polymer is biodegradable and will not permanently reside in the body and thereby cause a lysosomal storage problem. A key advantage for therapeutic modification with a heparosan polymer is that normal monosaccharides, GlcNAc and GlcUA are the products of the eventual degradation. In contrast, PEG degrades into reactive artificial aldehydes and ketones which are toxic above certain levels. PEG also accumulates in the body, especially when present as one or more high molecular weight polymers.

The normal roles of heparin/heparan sulfate in vertebrates include binding coagulation factors (inhibiting blood clotting) and growth factors (signaling cells to proliferate or differentiate). The key structures of heparin/heparan sulfate that are recognized by these factors include a variety of 0-sulfation patterns and the presence of iduronic acid [IdoUA]; in general, polymers without these modifications do not stimulate clotting or cell growth. Heparosan-based materials which do not have such O-sulfation patterns, therefore, do not provoke unwanted clotting or cellular growth/modulation. As such, heparosan-drug conjugates do not initiate clotting and/or cell growth processes and remain solely bio-reactive as per the drug or cargo constituent—the heparosan is thus termed or deemed to be biologically inert.

Foreign or unnatural molecules stimulate the immune system. Heparosan polymer exists transiently during heparan sulfate and heparin biosynthesis as well as being found in very short polymer structures within mature heparan sulfate or heparin chains. In the latter case, the N- and O-sulfation reactions are not complete in mammals, so traces of the original heparosan remain; for example, approximately 1-5 unsulfated disaccharide repeats can be interspersed within the sulfated regions. Therefore, the body treats heparosan as 'self,' and does not mount an immune response. *P. multocida* Type D and *E. coli* K5 utilize heparosan coatings to ward off host defenses by acting as molecular camouflage. Indeed, scientists had to resort to using capsule-specific phages or selective GAG-degrading enzymes to type these heparosan-coated microbes since a conventional antibody or serum could not be generated—the heparosan is thus termed or deemed non-immunogenic or non-antigenic.

Certain embodiments of the presently disclosed and/or claimed inventive concept(s) are directed to a method for preparing a pharmaceutically active heparosan polymer-drug conjugate. In the method, the drug may be any drug or therapeutic compound described or otherwise contemplated herein, including but not limited to, at least one polypeptide and/or at least one polynucleotide. In the method, at least one drug is reacted with at least one activated heparosan polymer under conditions sufficient to effect covalent or non-covalent conjugation of the at least one drug and the at least one heparosan polymer to form a reaction mixture containing one or more drug-heparosan polymer conjugates.

The conjugates produced by the method may be designed for administration to a mammalian patient by any method known in the art, or any method disclosed herein after or otherwise contemplated herein. In one non-limiting embodiment, the method may involve the preparation of an injectable, pharmaceutically active heparosan polymer-drug conjugate that is capable of circulating in a mammalian bloodstream.

The heparosan polymer used in the method of making the drug-heparosan polymer conjugate may be characterized as being substantially non-antigenic, substantially non-immunogenic, and substantially biologically inert within extracellular compartments of a mammalian patient, being stable in the mammalian bloodstream, and/or being degraded intracellularly in the mammalian patient. The heparosan polymer may be produced by any method known in the art or otherwise contemplated herein, as will be discussed in greater detail herein below. In addition, one of the advantages of the presently disclosed and/or claimed inventive concept(s) is that the heparosan can be synthesized in a step-wise, reproducible, and defined manner so as to provide all of the advantages of PEG without its potential side effects.

Any size and/or size distribution of heparosan can be utilized herein, so long as the heparosan can be conjugated to a drug and function in accordance with the presently disclosed and/or claimed inventive concept(s). In certain particular, non-limiting embodiments, the heparosan polymer may have a mass in a range of from about 600 Da to about 4.5 MDa. In addition, in certain particular, non-limiting embodiments, the heparosan polymers may be polydisperse in size. Alternatively, in other non-limiting embodiments, the substantially monodisperse in size. For example, but not by way of limitation, the substantially monodisperse heparosan polymers may have: (a) a molecular weight in a range of from about 3.5 kDa to about 0.5 MDa and a polydispersity value in a range of from about 1.0 to about 1.1; (b) a molecular weight in a range of from about 0.5 MDa to about 4.5 MDa and a polydispersity value in a range of from about 1.0 to about 1.5; and (c) a molecular weight in a range of from about 0.5 MDa to about 4.5 MDa and a polydispersity value in a range of from about 1.0 to about 1.2.

In certain embodiments of the presently disclosed and/or claimed inventive concept(s), the heparosan polymer utilized in the methods may be a linear chain. Alternatively, the heparosan polymer may have a branched geometry. In addition, the heparosan polymer may have a dendritic geometry. The heparosan polymer will be unsulfated and unepimerized.

The heparosan polymer may be further characterized as having a multi-hour half-life within extracellular compartments of the mammalian patient. For example, but not by way of limitation, the heparosan polymer may have a half-life of at least 15 hours within extracellular compartments of the mammalian patient.

As described herein, the presently disclosed and/or claimed inventive concept(s) may be used to encapsulate, attach, bind, or otherwise be used to affect the storage, stability, longevity, and/or release of drugs as the pharmaceutically active agent in a composition. In certain embodiments, the drug-heparosan conjugate may exhibit increased retention in blood and/or lymphatic circulation of a mammalian patient when compared to drug alone. In other embodiments and/or in addition thereto, the drug-heparosan conjugate may exhibit reduced occurrence of accumulation in organs and/or tissues of a mammalian patient when compared to drug alone.

The linkage between the at least one drug and the at least one heparosan polymer may be substantially stable or substantially labile. The use of a substantially labile bond allows for release of the drug from the heparosan polymer over time. In addition, the linkage between the at least one drug and the at least one heparosan polymer may be cleavable, thereby allowing for release of the free drug after administration.

In certain embodiments, the drug may be covalently conjugated to the heparosan polymer using at least one coupling chemistry that links at least one target group on the drug to at least one group on the heparosan polymer. The linkage between the at least one target group on the drug and the at least one group on the heparosan polymer may be substantially stable or substantially labile. In certain embodiments, the method may further include the activation of the heparosan polymer prior to reacting with the drug; this activation provides an activated group on the heparosan polymer with which a group on the drug reacts to effect the covalent or non-covalent conjugation of the drug to the heparosan polymer. Activation of the heparosan polymer may involve attachment of a reactive group to the heparosan polymer. Any reactive group known in the art or disclosed or otherwise contemplated herein may be utilized in accordance with the presently disclosed and/or claimed inventive concept(s). Examples of reactive groups that may be utilized include, but are not limited to, an aldehyde, alkyne, ketone, maleimide, thiol, azide, amino, carbonyl, sulfhydryl, hydrazide, phosphate, sulfate, nitrate, carbonate, ester, squarate, and combinations thereof. In particular, non-limiting examples, the activation step may involve the creation of an amino-, carbonyl-, and/or sulfhydryl-reactive group on the heparosan polymer.

In certain non-limiting embodiments, the drug of the conjugate may be at least one polypeptide drug, such as but not limited to, a peptide, a protein, and/or a glycoprotein. In other non-limiting embodiments, the drug of the conjugate may be at least one polynucleotide drug, such as but not limited to, at least one polymer comprised of deoxyribonucleic acid and/or ribonucleic acid. In yet other non-limiting embodiments, the drug of the conjugate may be at least one polynucleotide drug that is a nucleic acid-peptide hybrid. In yet further non-limiting embodiments, the drug of the conjugate may be a combination of any of the above.

Particular, non-limiting examples of drugs that may be utilized in the drug-heparosan conjugates of the presently disclosed and/or claimed inventive concept(s) include one or more of the following bioactive agents listed in (A)-(D) below:

(A) Anti-diabetics or metabolic regulators such as insulin, leptin, GLP-1, and/or analogs thereof;

(B) Protein therapeutics such as enzymes, cytokines, growth factors, hormones, receptors, antibodies and antibody fragments, immune complexes, combinations thereof, and the like. Also included are protein derivatives that enhance, modulate, or block the activity of any of the naturally-occurring or isolated molecules listed herein or interacting components in the biochemical or cellular pathways;

(C) For use with vaccines, one or more antigens, such as natural, heat-killer, inactivated, synthetic, peptides and even T cell epitopes (e.g., GADE, DAGE, MAGE, etc.), combinations thereof, and the like; and (D) Nucleic acid (NA; e.g., DNA or RNA or analogs) therapeutics such as aptamers, molecular binders, antisense, microRNAs, genes, combinations thereof, and the like. Also included are NA derivatives that enhance, modulate, or block the activity of any of the naturally-occurring or isolated molecules listed herein or interacting components in the biochemical or cellular or genetic pathways.

The drugs mentioned above may be used in combination as required. Moreover, the above drugs may be used either in the free form or, if capable of forming salts, in the form of a salt with a suitable acid or base. If the drugs have a carboxyl group, their esters may be employed.

The term "suitable acid" may refer to an organic acid, such as but not limited to, methanesulfonic acid, lactic acid, tartaric acid, fumaric acid, maleic acid, or acetic acid; or an inorganic acid, such as but not limited to, hydrochloric acid, hydrobromic acid, phosphoric acid, or sulfuric acid. The base may be an organic base, such as but not limited to, ammonia or triethylamine, or an inorganic base, such as but not limited to, sodium hydroxide or potassium hydroxide. The esters may be, for example but not by way of limitation, alkyl esters, aryl esters, aralkyl esters, and the like.

In certain particular, non-limiting embodiments, the at least one drug of the conjugate may be selected from the group consisting of a cytokine, a hormone, an enzyme, an antibody, an antibody fragment, an aptamer, functional equivalents or analogs thereof, and combinations thereof. For example, but not by way of limitation, the at least one drug may be selected from the group consisting of Granulocyte Colony Stimulating Factor (G-CSF), Interferon, Insulin, Growth Hormone (hGH), Glucagon-like peptide-1 (GLP-1), Phenylalanine Ammonia-Lyase (PAL), L-Asparaginase (Asp), Anti-TNF alpha Fab', functional equivalents or analogs thereof, and combinations thereof.

Another embodiment of the presently disclosed and/or claimed inventive concept(s) is directed to a composition comprising one or more of any of the heparosan-drug conjugates described or otherwise contemplated herein above. In certain particular, non-limiting embodiments, the composition may include at least a first conjugate of a heparosan polymer and a first drug and a second conjugate of a heparosan polymer and a second drug.

Another embodiment of the presently disclosed and/or claimed inventive concept(s) is directed to a pharmaceutical composition comprising one or more of any of the heparosan-drug conjugates described or otherwise contemplated herein above in combination with a pharmaceutically acceptable carrier and/or aqueous medium, as described in further detail herein below.

Other embodiments of the presently disclosed and/or claimed inventive concept(s) is directed to a method of use of any of the heparosan-drug conjugate containing compositions disclosed or otherwise contemplated herein above. In the method, a therapeutically effective amount of any of the compositions described or otherwise contemplated herein is administered to a mammalian patient so as to induce a therapeutic effect in the mammalian patient.

The drug-heparosan conjugate may be administered, for example but not by way of limitation, parenterally, intraperitoneally, intraspinally, intravenously, intramuscularly, intravaginally, subcutaneously, intranasally, rectally, and/or intracerebrally. Dispersions of the drug-heparosan conjugate may be prepared in glycerol, liquid poly[ethylene glycols], and mixtures thereof, as well as in oils. Under ordinary conditions of storage and use, such preparations of the drug-heparosan conjugate may also contain a preservative to prevent the growth of microorganisms.

Pharmaceutical compositions suitable for injection use include sterile aqueous solutions (where water soluble) or dispersions and sterile powders for the extemporaneous preparation of sterile injectable solutions or dispersions. When used for injection, the composition should be sterile and should be fluid to the extent that easy syringability exists. The compositions should also be stable under the conditions of manufacture and storage and should be preserved against the contaminating action of microorganisms such as bacteria and fungi. The drug-heparosan conjugate may be used in conjunction with a solvent or dispersion medium containing, for example but not by way of limitation, water, ethanol, poly-ol (i.e., glycerol, propylene glycol, and liquid poly[ethylene glycol], and the like), suitable mixtures thereof, vegetable oils, and combinations thereof.

The proper fluidity of the drug-heparosan conjugate may be maintained, for example but not by way of limitation, by the use of a coating such as lecithin, by the maintenance of the required particle size in the case of dispersion, and/or by the use of surfactants. Prevention of the action of microorganisms may be achieved by various antibacterial and antifungal agents, such as but not limited to, parabens, chlorobutanol, phenol, ascorbic acid, thimerosal, and the like. In many cases, it will be desirable to include isotonic agents, for example, sugars, sodium chloride, or polyalcohols such as mannitol and sorbitol, in the composition. Prolonged absorption of the injectable compositions may be brought about by including in the composition an agent that delays absorption, such as but not limited to, aluminum monostearate and/or gelatin.

Sterile injectable solutions may be prepared by incorporating the drug-heparosan conjugate in the required amount in an appropriate solvent with one or a combination of ingredients enumerated above, as required, followed by filtered sterilization. Generally, dispersions are prepared by incorporating the drug-heparosan conjugate into a sterile carrier that contains a basic dispersion medium and the required other ingredients from those enumerated above. In the case of sterile powders for the preparation of sterile injectable solutions, the methods of preparation may include vacuum drying, spray drying, spray freezing, and/or freeze-drying that yields a powder of the active ingredient (i.e., the drug-heparosan conjugate) plus any additional desired ingredient from a previously sterile-filtered solution thereof.

The drug-heparosan conjugate may be orally administered, such as but not limited to, with an inert diluent or an assimilable edible carrier. The drug-heparosan conjugate and other ingredients may also be enclosed in a hard or soft shell gelatin capsule, compressed into tablets, and/or incorporated directly into the subject's diet. For oral therapeutic administration, the drug-heparosan conjugate may be incorporated with excipients and used in the form of ingestible tablets, buccal tablets, troches, capsules, elixirs, suspensions, syrups, wafers, and the like. The percentage of the drug-heparosan conjugate in the compositions and preparations may, of course, be varied as will be known to the one of ordinary skill in the art. The amount of the drug-heparosan conjugate in such therapeutically useful compositions is such that a suitable dosage will be obtained.

In certain embodiments it may be desired to formulate parenteral compositions in dosage unit form for ease of administration and uniformity of dosage. The term "dosage unit form" as used herein refers to physically discrete units suited as unitary dosages for the subjects to be treated, with each unit containing a predetermined quantity of drug-heparosan conjugate calculated to produce the desired therapeutic effect. The specification for the dosage unit forms of the presently disclosed and/or claimed inventive concept(s) are dictated by and directly dependent on (a) the unique characteristics of the drug-heparosan conjugate and the particular therapeutic effect to be achieved, and (b) the limitations inherent in the art of compounding such a therapeutic compound for the treatment of a selected condition in a subject.

Aqueous compositions of the presently disclosed and/or claimed inventive concept(s) comprise an effective amount of the nanoparticle, nanofibril, or nanoshell or chemical composition of the presently disclosed and/or claimed inventive concept(s) dissolved and/or dispersed in a pharmaceutically acceptable carrier and/or aqueous medium. The biological material may be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or intraperitoneal routes. The preparation of an aqueous composition that contains an effective amount of the nanoshell composition as an active component and/or ingredient will be known to those of ordinary skill in the art in light of the present disclosure. Typically, such compositions may be prepared as injectables, either as liquid solutions and/or suspensions; solid forms suitable for using to prepare solutions and/or suspensions upon the addition of a liquid prior to injection may also be prepared; and/or the preparations may also be emulsified. Also, the heparosan vehicle can be used to enhance a secondary vehicle (e.g., liposomes, nanoparticles, etc.) that acts as a carrier or adjuvant for a drug.

EXAMPLES

Examples are provided hereinbelow. However, the presently disclosed and/or claimed inventive concept(s) is to be understood to not be limited in its application to the specific experimentation, results and laboratory procedures. Rather, the Examples are simply provided as one of various embodiments and is meant to be exemplary, not exhaustive.

Example 1

Heparosan (HEP) Conjugation Reagents

Figure 2:
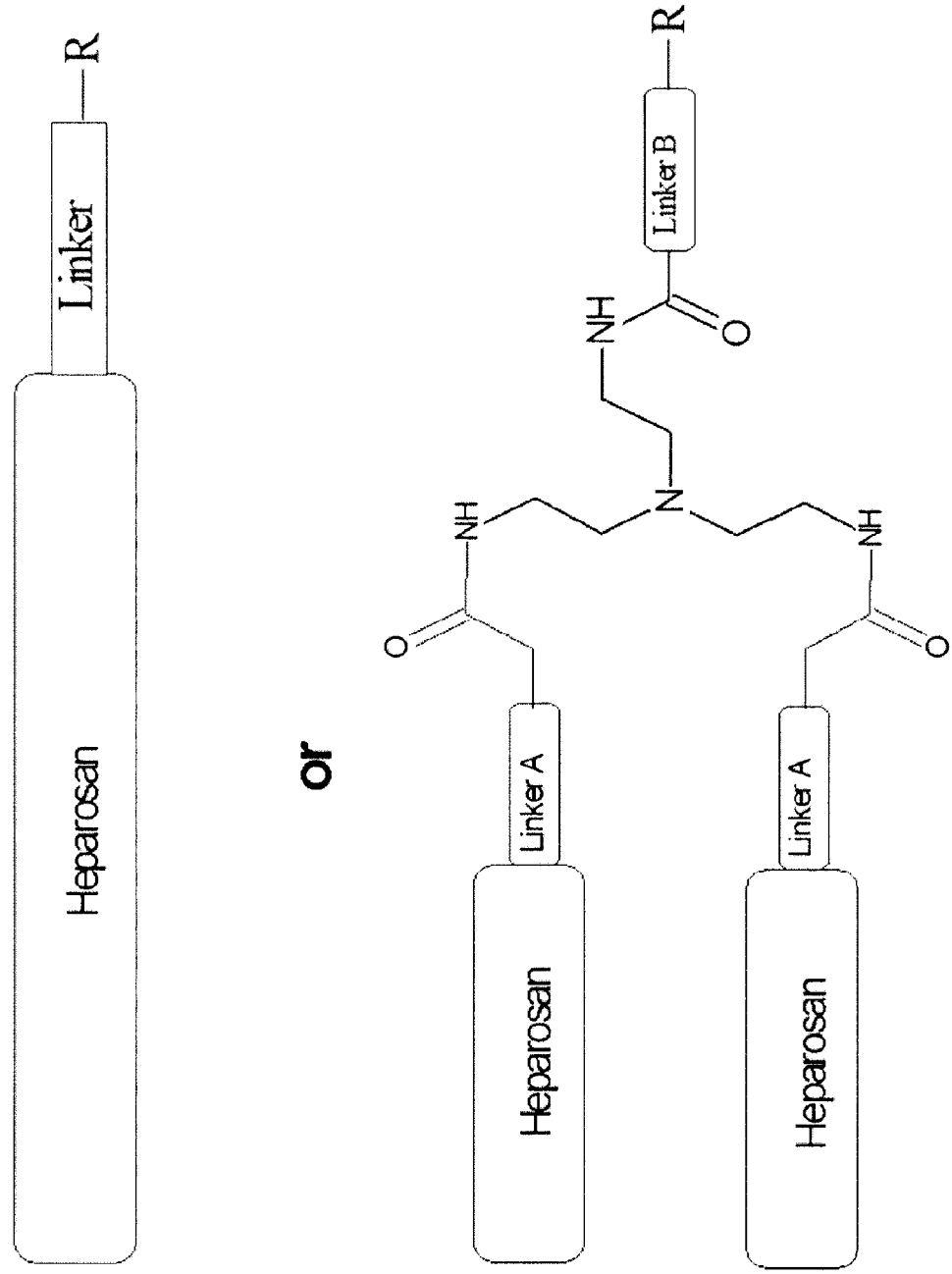
FIG. 2 depicts the schematic structure of chemically activated heparosan polymer employed in conjugating to drug or drug candidate. Activated heparosan with reactive groups, R, can be composed of either a single linear chain (top panel) or a branched configuration (lower panel). The linker can be of various lengths as well as contain either stable bonds or labile scissile bonds as needed to deliver the drug cargo.
Figure 4:
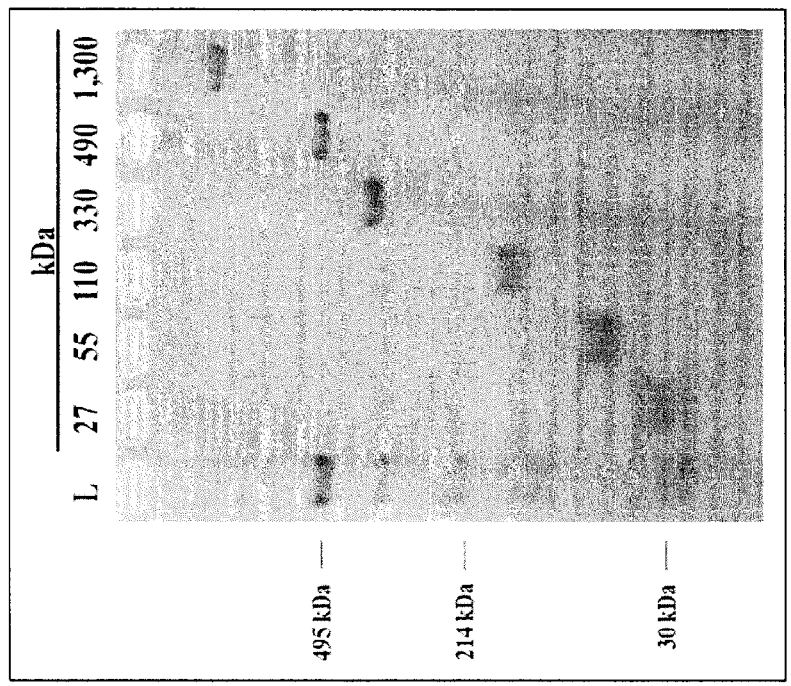
FIG. 4 shows an agarose gel stained with Stains-All demonstrating an analysis of various HEP amines (ranging from 27 to 1,300 kDa) compared to HA standards (L; Hyalose LLC, Oklahoma City, Okla.) (molecular masses are indicated). Various size quasi-monodisperse polymers were generated.
Figure 3:
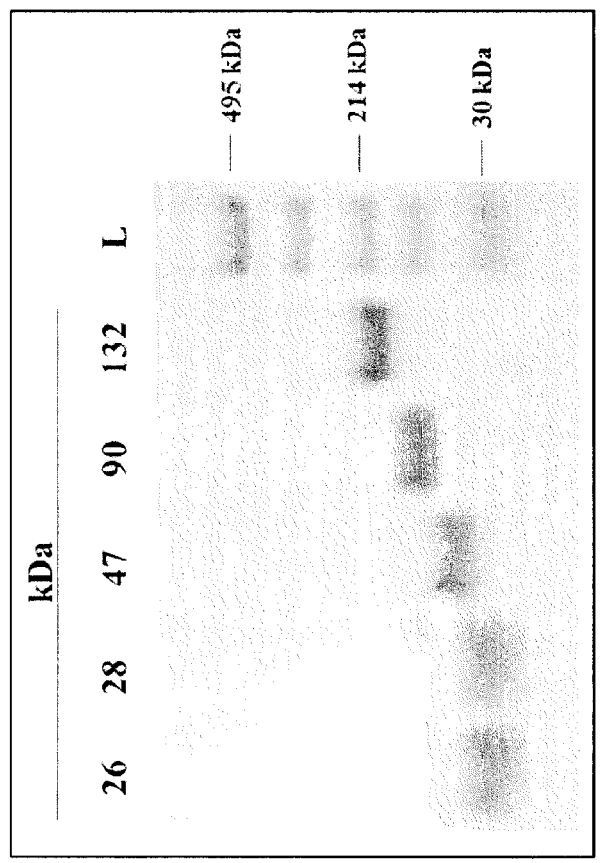
FIG. 3 depicts an agarose gel electrophoresis analysis of heparosan reagents. Purified heparosan aldehyde (0.4 μg/lane) of several sizes (26, 28, 47, 90, or 132 kDa) as well as hyaluronan (HA) standards (lane L; Select-HA LoLadder, Hyalose LLC, Oklahoma City, Okla.; molecular masses are indicated) were separated on a 1×TAE 0.7% agarose gel (Bio-rad Laboratories, Inc., Hercules, Calif.) and stained with Stains-All (Sigma-Aldrich, St. Louis, Mo.; 0.005-0.01% of Stain-all in 50% ethanol). Various size quasi-monodisperse polymers were generated.
Figure 6:
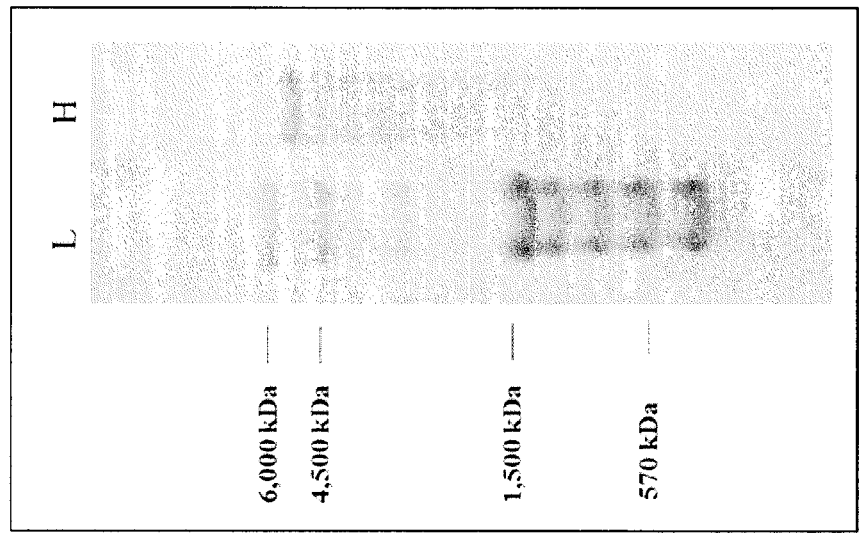
FIG. 6 shows an agarose gel stained with Stains-All demonstrating an analysis of 4,500 kDa HEP amine (H) versus the MegaLadder (L; Hyalose LLC, Oklahoma City, Okla.) (molecular masses are indicated). Extremely large size quasi-monodisperse polymer was generated.
Figure 5:
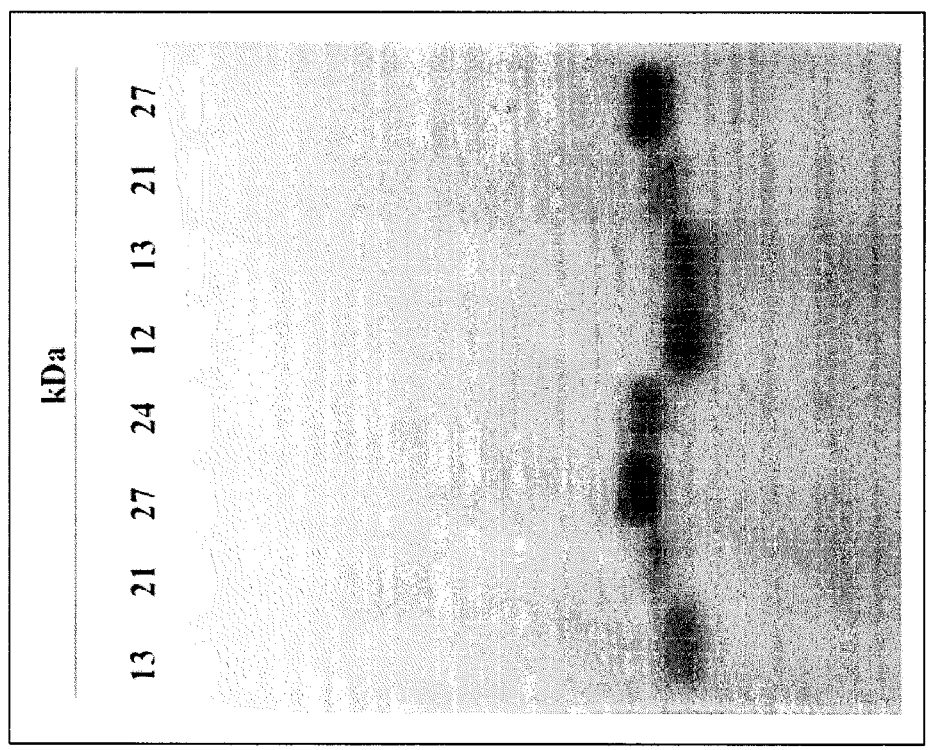
FIG. 5 shows an agarose gel stained with Stains-All demonstrating an analysis of various HEP amines (from left to right in kDa: 13, 21, 27, 24, 12.4, 13, 21, and 27 as determined by Multi Angle Laser Light Scattering). Various size quasi-monodisperse polymers were generated.

HEP has utility as a biocompatible, biodegradable vehicle for enhancing therapeutics as described in U.S. Published Patent Application No. 2010/0036001, incorporated supra. The synthesis of various sized (ranging from about 600 Da to about 4,500 kDa) heparosan polymers are possible using biosynthetic enzymes called heparosan synthases. These HEP polymers are modified to carry a functional group (e.g., aldehyde, maleimide, amine, iodoacetyl, etc.) which facilitates the coupling to drugs at various locations. FIG. 1 illustrates the strategy used to generate the described drug conjugates. FIG. 2 shows the general structure of the employed heparosan polymers and representative examples of functional groups used to link the heparosan polymers to their targets (Table 2). While the linker is shown schematically here, the actual structure can be either stable or cleavable depending on the needs of the therapeutic. For example, some drugs may remain attached to the HEP chain while acting in the body, while for other conjugates, the drug must be released from the HEP vehicle to act; thus, a cleavable linker (e.g., structure containing hydrolysable ester, protease clip site, etc.) is employed to release the free drug after administration.

TABLE 2

Heparosan Functional Groups

| Reactive Group "—R" | Reactive Group | Reactive Towards |
|---|---|---|
| —SH | Sulfhydryl | Thiol, malemide, iodoactyl, vinyl sulfone |
| (maleimide structure) | Maleimide | Sulfhydryl; amino (at high pH) |
| (aldehyde structure) | Aldehyde | Amine, hydrazide |
| (iodoacetyl structure) | Iodoacetyl | Sulfhydryl |
| (squarate structure) | Mono-squaramide "squarate" | Amine |

FIGS. 3 through 6 depict representative preparations of heparosan polymers synthesized by the chemoenzymatic route. The size distribution is very narrow (quasi-monodisperse) due to reaction synchronization (i.e., all chains are elongated in parallel). For example, the polydispersity values for some heparosan preparations in the presently disclosed and/or claimed inventive concept(s) were: 12-kDa, 1.003; 55-kDa, 1.007; 99-kDa; 1.005; 305-kDa, 1.005

(where 1 is the ideal perfect polymer, and naturally occurring polymers typically range in the approximately 1.5 to 3 range, depending on the source and preparation method). The polymer size is controlled by reaction stoichiometry (i.e., UDP-sugar precursor to primer/acceptor ratio). It should be noted that the site of activation (the location of a reactive functionality) in any reaction between heparosan and polypeptide or polynucleotide can be reversed, if desired. For example, the protein could have a maleimide or iodoacetyl group and the HEP chain can have a thiol group or vice versa (as in Table 3). Likewise, the target on the drug can have an aldehyde (e.g., generated by oxidation of a sugar chain or certain amino acids) and a heparosan-amine derivative employed or vice versa. Some examples of various HEP-drug conjugates are listed in Table 3.

In addition, multiple intermediary coupling or activating steps can be employed with the goal of adding heparosan to the drug or drug candidate; for example the lysine(s) of a protein could be first modified with Traut's reagent (iminothiolane), thus adding a new sulfhydryl group(s) to the protein that is subsequently reacted with sulfhydryl-reactive heparosan(s) (e.g., maleimide, iodoacetyl). Furthermore, depending on the desired therapeutic profile and the nature of the drug or drug candidate, various size heparosan polymers (e.g., about 600 Da to about 4,500 kDa) in any geometry (e.g., linear, branched, dendritic) are employed.

In summary, the end product, the covalently bound heparosan-drug conjugate with some biological activity or functional utility, can be made in various fashions (e.g., using known coupling chemistries in the art including those not listed here as well as future permutations, in addition to alternative coupling sites of the drug or drug candidate) without affecting the spirit and scope of the presently disclosed and/or claimed inventive concept(s).

position by the hand of man. Heparosan with a free amino group at its reducing terminus can be prepared by multiple routes including, but not limited to: (i) chemoenzymatic extension of heparosan oligosaccharides containing an amine (or an amine intermediary or precursor e.g., azido, etc.) using UDP-sugars and a heparosan synthase; (ii) nitrous acid fragmentation of heparosan polymer and reductive amination with a diamine or ammonia; or (iii) reductive amination of heparosan with a diamine or ammonia. Modification at the reducing termini of HEP chain does not interfere with the normal lysosomal processing of heparosan mediated by exoglycosidases that act at the non-reducing terminus, thus is particularly well suited for making HEP-drug conjugates that are biodegradable.

The primary amine group at the reducing termini of heparosan-$NH_2$ polymer is converted into a thioacetyl, iodoacetyl, maleimide, or aldehyde group or any other desired functionality that is compatible with the reaction conditions by treating the polymer with the appropriate heterobifunctional reagent (i.e., a reagent with two distinct chemically reactive moieties). Typically, such heterobifunctional reagents possess, but not limited to: (i) a N-hydroxysuccinimide or sulfo-N-hydroxysuccinimide ester (e.g., NHS-esters); and (ii) the desired thioacetyl, iodoacetyl, maleimide, or aldehyde group, etc. In such an activation reaction, heparosan amine reacts with the NHS-ester of the heterobifunctional reagent, forming a stable amide bond, and the other desired group is now added to the reducing terminus of heparosan chain; this desired group is later coupled to the drug or drug candidate.

For example, but not limited to, heparosan-$NH_2$ at a concentration of ~5-40 mg/mL in a solution of 100 mM sodium phosphate, pH 6.5-8.5, (or similar neutral to basic pH buffer that lacks free amino groups) containing 0-35%

TABLE 3

Drug Conjugate Examples

| Drug [Class] | Heparosan Activated Group* | Reactive Site on Drug* | Potential Heparosan Chain Molecular Weight |
|---|---|---|---|
| Granulocyte Colony Stimulating Factor (G-CSF) [hormone, cytokine] | Aldehyde | Amine | Ranging from 600 Da to 4,500 kDa |
| Interferon [cytokine] | Aldehyde | Amine | Ranging from 600 Da to 4,500 kDa |
| Insulin [hormone] | Aldehyde or Squarate | Amine | Ranging from 600 Da to 4,500 kDa |
| Growth Hormone (hGH) [hormone] | Aldehyde | Amine | Ranging from 600 Da to 4,500 kDa |
| Glucagon-like peptide-1 (GLP-1) [hormone, peptide] | Maleimide or Iodoacetate | Sulfhydryl | Ranging from 600 Da to 4,500 kDa |
| Phenylalanine Ammonia-Lyase (PAL) [enzyme] | Maleimide or Iodoacetate | Sulfhydryl | Ranging from 600 Da to 4,500 kDa |
| L-Asparaginase (Asp) [enzyme] | Maleimide or Iodoacetate | Sulfhydryl | Ranging from 600 Da to 4,500 kDa |
| Anti-TNF alpha Fab' [antibody fragment, binding protein] | Maleimide or Iodoacetate | Sulfhydryl | Ranging from 600 Da to 4,500 kDa |
| Aptamer [DNA, RNA polynucleotide-peptide, binding molecule] | Maleimide or Iodoacetate | Sulfhydryl | Ranging from 600 Da to 4,500 kDa |

*note:
the reverse order with the reactive group on Drug versus HEP is also possible Chemical Activation of Heparosan: HEP-$NH_2$ Polymer with N-Hydroxysuccinimide or Sulfo N-Hydroxysuccinimde Esters The amine group is a useful functionality for further chemical modification, but the natural heparosan [-4-N-acetylglucosamine-α1,4-glucuronic acid-β1-] structure does not normally contain a free amine; therefore, such a functionality or reactive group must be placed in a desirable dimethylsulfoxide, (if needed for solubility of the activation reagent) was reacted with ~2-50 molar equivalents of suitable N-hydroxysuccinimide or sulfo-N-hydroxysuccinimide esters containing the desired functionalities at 4-37° C. for 1-12 hours (and again, this is just a general protocol that can be modified to some degree by those of ordinary skill in the art). The obtained polymers can be recovered by various methods including, but not limited to, precipitation with a water-mixable organic solvent, such as alcohols or acetone, or anion exchange chromatography, or size exclusion chromatography, or tangential flow filtration, or ultrafiltration. Any combination of these techniques can be also used to obtain purified activated polymer.

Chemical Activation of Heparosan: HEP-NH$_2$ Polymer with 3,4-diethoxy-3-cyclobutene-1,2-dione Alternatively, instead of employing a NHS-ester to activate heparosan-NH$_2$, one can employ squarene-based ("squarate") reagents (e.g., 3,4-diethoxy-3-cyclobutene-1,2-dione) as an intermediate or the end product. In one example, the reducing termini primary amine of heparosan-NH$_2$ (~5-40 mg/mL) in 50-100 mM sodium phosphate, pH 7.4 (or similar neutral to basic pH buffer that lacks free amino groups), and 15-30% ethanol was converted into the mono-squaramide by treatment with ~2-100 molar equivalents of 3,4-diethoxy-3-cyclobutene-1,2-dione for 1-12 hours.

The obtained polymers can be recovered by methods including, but not limited to, precipitation with a water-mixable organic solvent, such as alcohols or acetone, anion exchange chromatography, size exclusion chromatography, tangential flow filtration, ultrafiltration, etc. Any combination of these techniques can be used to obtain purified activated polymer.

Chemical Activation of Heparosan: Branched HEP-Aldehyde Polymers

In another non-limiting example, an aldehyde-containing (e.g., an amino reactive group) branched (i.e., containing multiple chains with a common attachment site) heparosan moiety was synthesized. First, tris(2-aminoethyl)amine hydrochloride was reacted with 1 molar equivalent of succinimidyl-p-formylbenzoate in 50 mM HEPES in 75% dimethylsulfoxide at pH 7.0 for 3.5 hours at ambient temperature. The reaction mixture was diluted with 20 volume equivalents of water and filtered, and the filtrate was evaporated to dryness. Cation exchange chromatography over HiTrap® SP chromatography columns (GE Healthcare Bio-Sciences AB LLC, Uppsala, Sweden) at pH 4.0 with a sodium chloride gradient yielded N-{2-[bis(2-aminoethyl)amino]ethyl}-4-formylbenzamide, which was subsequently desalted by reversed phase solid phase extraction over Strata-X™ SPE tubes (Phenomenex, Inc., Torrance, Calif.). Second, N-{2-[bis(2-aminoethyl)amino]ethyl}-4-formylbenzamide was reacted with 10 molar equivalents of succinimidyl acetylthioacetate in 35 mM HEPES buffer, pH 7.0 in 66.6% dimethylsulfoxide at ambient temperature for 3 hours, after which time an additional 6 molar equivalents of succinimidyl acetylthioacetate in dimethylsulfoxide were added, and the reaction left to continue for another 2.5 hours. The mixture was freeze-dried overnight, and the obtained residue purified by reversed phase chromatography to yield the target crosslinker with two thioacetate and one benzaldehyde functionality. Third, the two thioacetate functionalities were reacted with 2.5 molar equivalents of a 41.5-kDa heparosan-maleimide polymer in 100 mM sodium phosphate, pH 7.0, 50 mM hydroxylamine hydrochloride, and 2.5 mM EDTA overnight at ambient temperature. However, other buffer systems in the pH range from 6.5-8.5 will also work. The obtained dimer was separated from unreacted monomer by size-exclusion chromatography over a Sephacryl S-300 column with 50 mM sodium phosphate, pH 7.0, 150 mM NaCl as eluent. The combined clean dimer containing fractions were precipitated by addition of isopropanol, dried in vacuo, and re-dissolved in water to yield the target heparosan dimer with an reactive aldehyde functionality at the reducing end.

Of course, other architectures (e.g., more branches, etc.) or reducing terminal reactive groups (e.g., maleimide, amine, iodoacetate, squarate) depending on the strategy and route of synthesis; the reagent above is just one non-limiting example of an activated branched heparosan reagent.

Example 2

Heparosan-Polypeptide Conjugates—HEP-Granulocyte Colony Stimulating Factor (G-CSF)

G-CSF is a protein that stimulates white blood cell formation and has applications in treating neutropenia from various causes including cancer treatment. Typically, G-CSF alone (e.g., NEUPOGEN® (filgrastim, Amgen Inc., Thousand Oaks, Calif.)) needs multiple injections to have a biological effect; thus, protractors such as polyethylene glycol (PEG) have been coupled to G-CSF (e.g., NEULASTA® (pegfilgrastim, a commercial 20-kDa PEGylated G-CSF, Amgen Inc., Thousand Oaks, Calif.)) and have been used to increase the half-life, thus needing just one injection per treatment. However, PEG is a synthetic polymer that is not strictly biocompatible/biodegradable. HEP on the other hand is completely biocompatible as it is a 'self' molecule in the mammalian body; a molecule that normally exists in the healthy body is not subject to immune surveillance (i.e., not immunogenic and not seen as 'foreign') and is also amenable to natural and processing systems (e.g., movement through tissue or cellular compartments, molecular degradation pathways, etc.).

In one example, ~1.5 to 12 equivalents of HEP with a reducing terminal aldehyde (e.g., a heparosan synthase-extended aldehyde-containing acceptor or an aldehyde-activated HEP-NH$_2$) (HEP-CHO or HEP-ald) is coupled to the amino-terminus of human G-CSF (recombinant *E. coli*; ProSpec-Tany TechnoGene Ltd., East Brunswick, N.J.) via reductive amination with sodium cyanoborohydride (Sigma-Aldrich, St. Louis, Mo.) at ~pH 5-6 (typically in an acetate buffer system at 0-37° C. for 0.1-24 hours, but other buffers, incubation temperature and times, reducing agents, and different pH ~4.5 to 7, or molar ratios may substitute). Various sizes of heparosan (i.e., different polymer chain lengths, such as the heparosan polymers having a mass ranging from about 600 Da to about 4,500 kDa; measured in Daltons [Da] to kilo Daltons [kDa]) were coupled to the protein. The HEP-G-CSF conjugate was purified by ion exchange chromatography with HiTrap® Q Sepharose High Performance column (GE Healthcare Bio-Sciences AB LLC, Uppsala, Sweden) pre-equilibrated with 20 mM sodium acetate, pH 5.0 (buffer A). HEP-G-CSF conjugate was separated from uncoupled free G-CSF by elution with a linear or step gradient to 50% of buffer B (1M NaCl in buffer A) over 20 column volumes (CVs). Fractions containing the conjugate were pooled, concentrated and exchanged into G-CSF Storage Buffer (10 mM sodium acetate, pH 4.0-4.5, 5% sorbitol) in spin units with molecular weight cut off of 3 kDa to 10 kDa. The conjugate solution was then sterile filtered through 0.2 μm spin filter units (Corning Inc., Tewksbury, Mass.), aliquoted, and stored at −80° C. All conjugate concentrations indicated in this example are the concentration of protein (i.e., based on a G-CSF standard) determined with Bradford Assay.

Figure 7:
FIG. 7 depicts gel analysis of the removal of HEP polymer with heparin lyase III. The drug conjugate (lane C) was digested by heparin lyase III ($L_{ase}$) and then was analyzed by SDS-PAGE gel with PageBlue™ protein staining solution (Thermo Fisher Scientific Inc., Rockford, Ill.). From left to right: drug alone (lane D), lyase alone control ($L_{ase}$), conjugate (C) incubated with (+) or without (−) lyase. The HEP increases the size of the drug, but HEP removal with the bacterial heparin lyase III enzyme causes the drug to revert to its original mobility, and a lower MW product is again observed.

The major HEP-G-CSF conjugate has one HEP polymer chain per protein, but a small amount of "dimer" (one HEP coupled to a lysine side-chain in addition to the HEP coupled to the amino terminus) is also observed in some cases where higher stoichiometric ratios of HEP:protein are employed). Addition of HEP to the N-terminal of G-CSF was confirmed with peptide mapping. Briefly, HEP-G-CSF conjugates were treated with bacterial heparin lyase III to release the protein with a short sugar stub and run on SDS-PAGE (FIG. 7). After staining, protein bands were excised from the gel, digested with trypsin to make peptides, and analyzed by reverse-phase HPLC with ACCLAIM® PepMap100 C18 column (Thermo Fisher Scientific Inc., Rockford, Ill.). A multi-step gradient (trifluoroacetic acid [TFA]/Formic acid/acetonitrile-based solvent) was employed, and MS/MS data was collected using ABI ANALYST® QS 2.0 software (Applied Biosystems, Thermo Fisher Scientific Inc., Rockford, Ill.) by fragmentation of ions between 300 and 2500 m/z and having a charge between +2 and +3. Data was submitted to a MASCOT server (Matrix Science Inc., Boston, Mass.) for identification against the National Center for Biotechnology Information (NCBInr; February 2012) protein database. Based on the results, peptide "MTPLGPASSLPQSFLLK" with extra molecular weight corresponding to the sugar stub plus linker attached at the amino terminal of the peptide is the predominant fragment.

Figure 8:
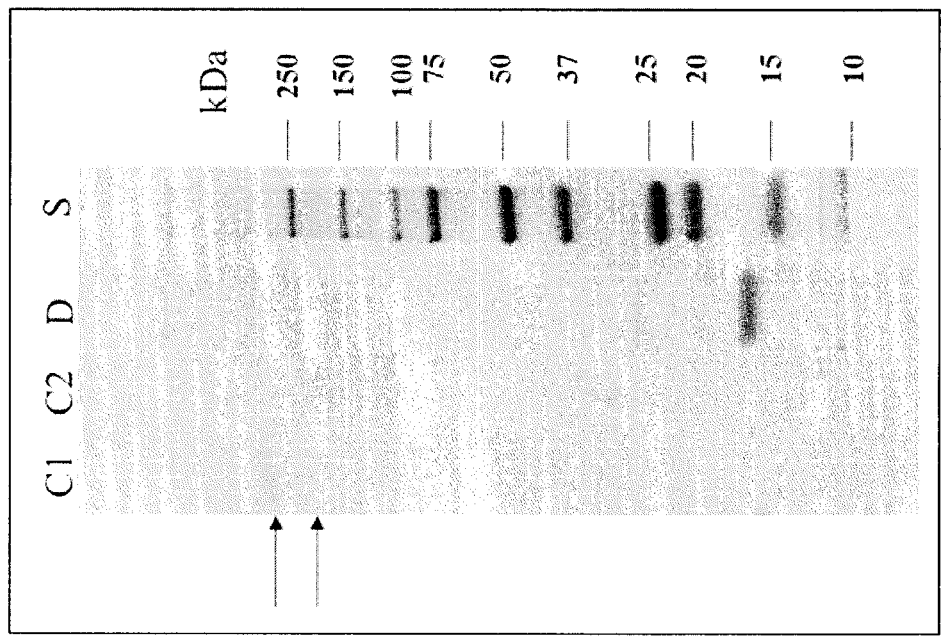
FIG. 8 depicts a gel analysis of HEP-G-CSF. The samples, 99-kDa HEP-G-CSF (lane C1), 55-kDa HEP-G-CSF (lane C2), or 2 μg of free G-CSF drug (lane D), were separated on 4-20% SDS-PAGE gel (Bio-rad Laboratories, Inc., Hercules, Calif.) and stained with the PageBlue™ protein staining solution (Thermo Fisher Scientific Inc., Rockford, Ill.). The standard (S) is the Precision Plus Protein™ standard (Bio-rad Laboratories, Inc., Hercules, Calif.; molecular masses are indicated). Heparosan-G-CSF conjugates were produced (indicated by arrows). Please note that: (i) the HEP-protein drug conjugate does stain, but heparosan alone, a polysaccharide, does not stain with Coomassie Blue or many other protein detection stains; (ii) that the presence of a HEP chain may partially block the protein-derived signal of such protein detection stains; and (iii) that the exact molecular weight of a HEP-conjugate cannot be accurately calculated using protein standards and the PAGE gel system, due to the disparity in electrophoretic migration between polysaccharides and polypeptides.
Figure 9:
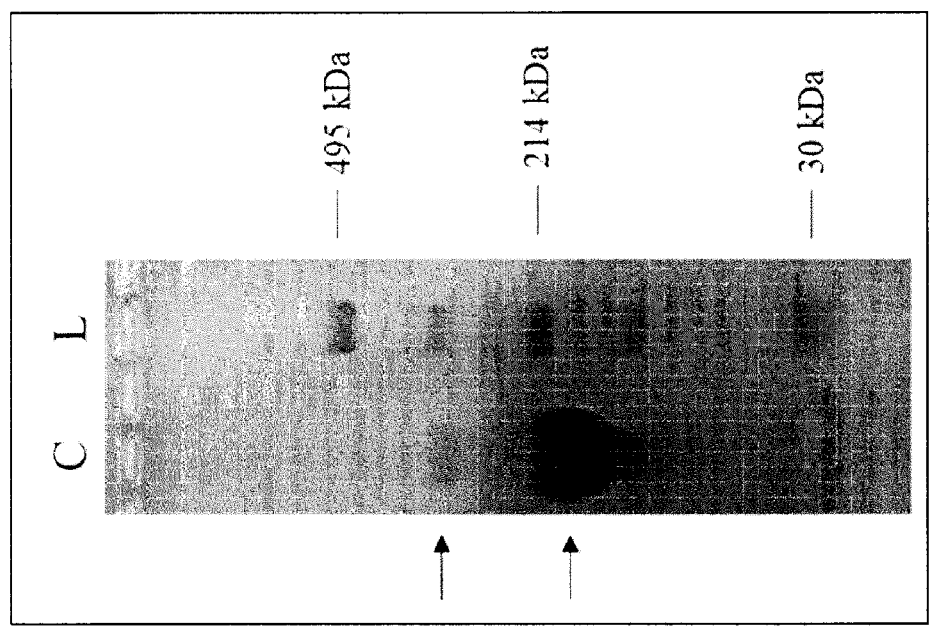
FIG. 9 depicts an agarose gel electrophoresis of HEP-G-CSF. Purified 99-kDa HEP-G-CSF conjugate (lane C), and HA standards (lane L) (Select-HA LoLadder, Hyalose LLC, Oklahoma City, Okla.; molecular masses are indicated) were analyzed with 2% agarose gel and Stains-All. The upper arrow indicates the dimeric conjugate with 2 HEP per G-CSF, and the lower arrow indicates the monomeric conjugate with 1 HEP per G-CSF. Please note that the exact molecular weight of a HEP-protein conjugate cannot be accurately calculated using polysaccharide standards and the agarose gel system due to the disparity in electrophoretic migration between polysaccharides and polypeptides.

Representative SDS-PAGE gel (4-20% gel) and agarose gel profiles depicting the HEP-G-CSF conjugates are shown in FIG. 8 and FIG. 9. Please note that in general for interpreting such data elements that: (i) the HEP-protein drug conjugate does stain, but heparosan alone, a polysaccharide, does not stain with Coomassie Blue or many other protein detection stains (e.g., PageBlue™ protein staining solution (Thermo Fisher Scientific Inc., Rockford, Ill.)); (ii) that the presence of a HEP chain may partially block the protein-derived signal of such protein detection stains (i.e., underestimates the amount of protein); (iii) that the exact molecular weight of a HEP-conjugate cannot be accurately calculated using protein standards and the PAGE gel system due to the disparity in electrophoretic migration between polysaccharides and polypeptides; and (iv) that the exact molecular weight of a HEP-conjugate cannot be accurately calculated using polysaccharide standards and the agarose gel system due to the disparity in electrophoretic migration between polysaccharides and polypeptides.

Figure 10:
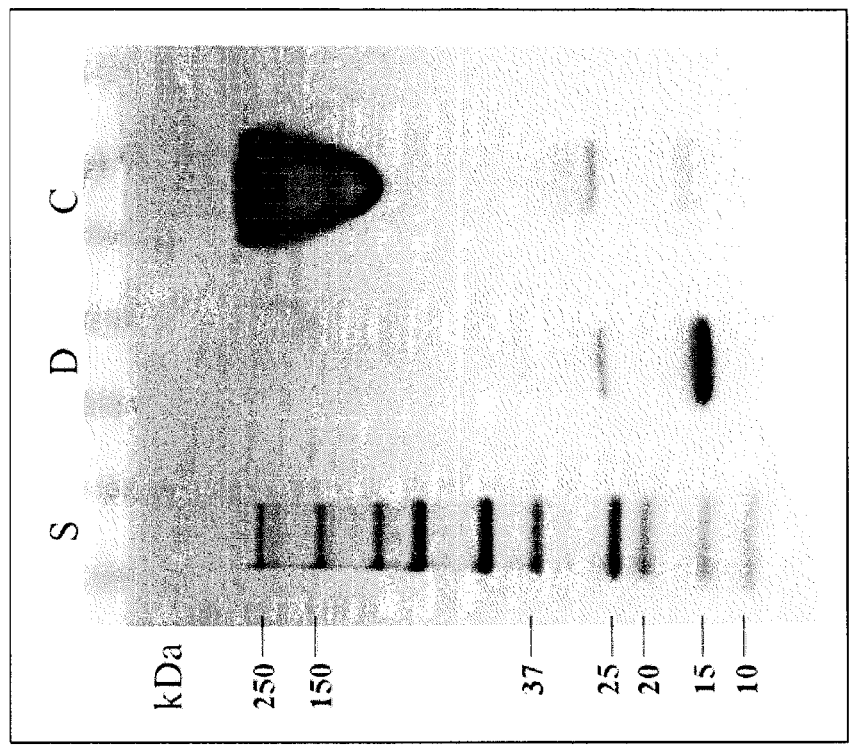
FIG. 10 depicts a gel analysis of HEP-G-CSF modified at Cys17. Respectively from left to right, protein MW standard (lane S) (molecular masses are indicated), 5 μg Free G-CSF (lane D), HEP-G-CSF conjugate (lane C) (equivalent to ~10 μg G-CSF) were separated on 4-20% SDS-PAGE gel and stained with PageBlue™ protein staining solution (Thermo Fisher Scientific Inc., Rockford, Ill.). The target HEP-drug conjugate was formed.

In another example of a HEP-G-CSF conjugate, the reducing terminal maleimide of the heparosan chain is coupled to the thiol of cysteine 17 of recombinant human G-CSF (r h G-CSF; ProSpec-Tany TechnoGene Ltd., East Brunswick, N.J.). In one non-limiting example, a 10:1 molar ratio of HEP reagent (55 kDa HEP-Maleimide) to rhG-CSF protein was employed in the derivatization reaction. A solution of 0.4 mg per mL G-CSF, 3.75 M guanidinium chloride and 50 mM sodium phosphate, pH 7.0 was incubated at room temperature for 4 hours and was then added to a tube containing lyophilized HEP reagent. Argon was blown into the reaction tube (to prevent oxidation of the thiol group), and the reaction was incubated at room temperature with gentle rolling for ~16 hours. Guanidinium chloride was then removed by buffer exchange into 50 mM sodium phosphate, pH 7.0 in spin units with molecular weight cut off of 3 kDa (Pall Corp., Port Washington, N.Y.). The HEP-G-CSF conjugate was detected by separation on SDS-PAGE gel followed by staining the gel with PageBlue™ protein staining solution (Thermo Fisher Scientific Inc., Rockford, Ill.) (FIG. 10).

Figure 11:
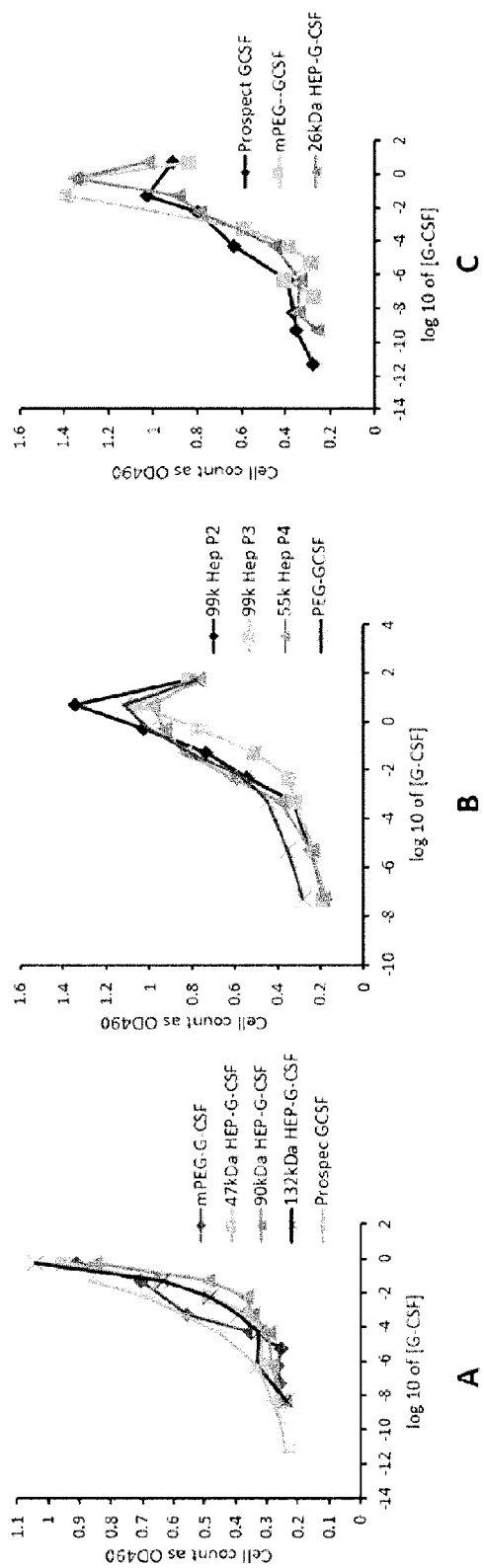
FIG. 11 illustrates the in vitro HEP-G-CSF potency in a NFS-60 cell proliferation assay. NFS-60 cells were plated at 5 k-10 k cells/well in RPMI 1640 with 10% FBS after a thorough wash with PBS. The cells were treated with either media alone, 30 ng/ml G-CSF (ProSpec-Tany TechnoGene Ltd., East Brunswick, N.J.), or 20-kDa PEG-G-CSF or various sizes of HEP-G-CSF (with 26, 47, 90, 99, or 132 kDa heparosan chains) in serial dilutions ranging from 50 μg/ml to 50 ng/ml at 37° C., 5% $CO_2$ for 3-4 days. CellTiter 96® AQueous One Solution Reagent (Promega Corp., Madison, Wis.) was added and incubated for 3 hours according to the manufacturer's instructions. Absorbance was measured at 490 nm and corresponds to cell number (higher absorbance, more cells). The HEP-drug conjugates possess biological activity.

Various purified HEP-G-CSF conjugates were tested with an in vitro cell proliferation assay using a G-CSF-dependent NFS-60 cell line (American Type Culture Collection (ATCC®), Manassas, Va.) in the 96-well format and a plate-reading spectrophotometer. Without exogenously added G-CSF, these cells do not grow; therefore, the live cell staining method (CellTiter 96® AQueous One Solution (Promega Corp., Madison, Wis.)) will give a low background signal. If the G-CSF is present, then the cells proliferate over the ~3-day test period and thus yield a higher signal (y-axis of plots; absorbance at 490 nm). All samples were tested at various concentrations in duplicate (higher concentrations as move from left to right of plot on x-axis; log of concentration of ng/ml). The PEG conjugate (similar to NEULASTA® (pegfilgrastim, Amgen Inc., Thousand Oaks, Calif.), 20-kDa PEG-G-CSF made by Caisson Biotech, Oklahoma City, Okla.), and all of the HEP conjugates in the tested range (26 kDa to 132 kDa) were active to varying degrees, as shown in FIG. 11.

Figure 12:
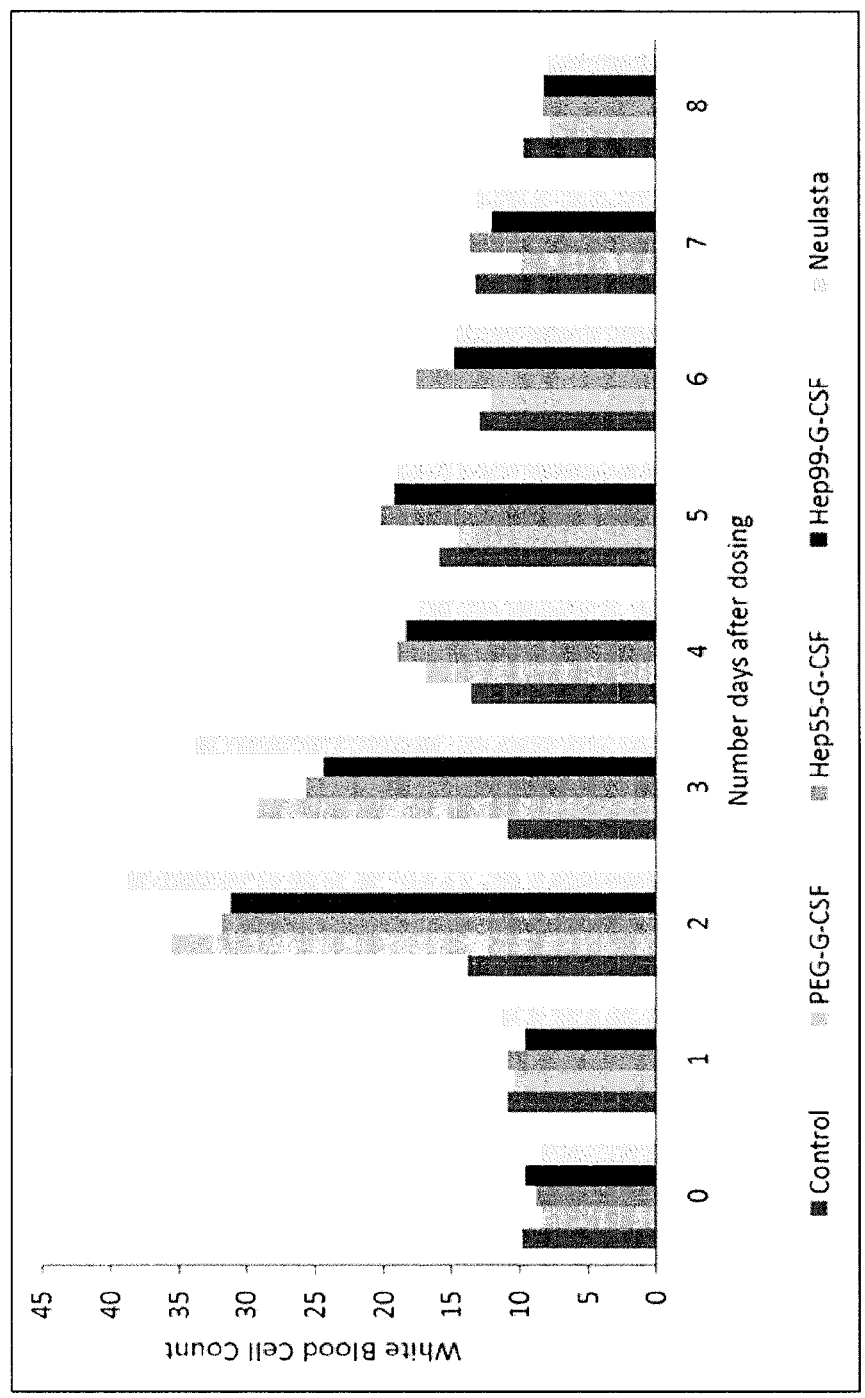
FIG. 12 illustrates the in vivo HEP-G-CSF efficacy test in rats. In this experiment, rats were dosed with a single subcutaneous injection of various forms of HEP-G-CSF or PEG-G-CSF, and the white blood cell counts were monitored over time. Male rats (5 rats/group) were given either control vehicle (10 mM sodium acetate, pH 4.0-4.5, 5% sorbitol), or one of the four test articles of 55-kDa HEP-G-CSF, 99-kDa HEP-G-CSF, homemade 20-kDa PEG-G-CSF, and NEULASTA® (pegfilgrastim, commercial 20-kDa PEGylated G-CSF, Amgen Inc., Thousand Oaks, Calif.) at 0.1 mg/kg at a volume of 1.5 mL/kg. The rats were observed for 7 days followed by termination on Day 8. Blood was collected via retro-orbital sinus for hematology studies before dosing and once daily after injection. In general, both 55-kDa and 99-kDa HEP-G-CSF significantly increase the level of white blood cells in circulation of mammals and are comparable in efficacy to NEULASTA® (pegfilgrastim, Amgen Inc., Thousand Oaks, Calif.), the FDA-approved long-acting version of G-CSF.

The HEP-G-CSF conjugates (reductive amination method) and PEG-G-CSF (20-kDa PEG-G-CSF made by Caisson Biotech, LLC (Oklahoma City, Okla.) or commercially obtained NEULASTA® (pegfilgrastim, Thousand Oaks, Calif.)) were tested in animal models using Sprague Dawley rats (n=3-7), where the hematology and various aspects pertaining to toxicology were monitored over a week period (FIG. 12; performed by Xenometrics, LLC, Stilwell, Kans.). A single dose (0.1-3 mg/kg of bodyweight) of drugs or vehicle control per rat was administered via subcutaneous injection on Day 1, and hematology was monitored until Day 8.

Both the HEP-G-CSF conjugates and the PEG-G-CSF conjugates (either 20-kDa PEG-G-CSF made at Caisson Biotech, LLC or NEULASTA® (pegfilgrastim, Amgen Inc., Thousand Oaks, Calif.)) demonstrated a similar pattern; the white blood cell (WBC) count was increased for a prolonged time after a single dose (Table 4, FIG. 12). The red blood cell counts remained approximately the same (not shown). No significant adverse effects were noted based on clinical observations and necroscopy analysis.

TABLE 4

In vivo G-CSF Efficacy in Normal Rats -
Change in absolute White Blood Cell (WBC) Counts relative to vehicle control

| Treatment Groups | WBCs: % change from the control | | | | | | | |
|---|---|---|---|---|---|---|---|---|
| | Day 1 | Day 2 | Day 3 | Day 4 | Day 5 | Day 6 | Day 7 | Day 8 |
| PEG-G-CSF | −15 | −5 | +157 | +170 | +25 | −8 | −6 | −25 |
| 55-kDa HEP-G-CSF | −10 | NC | +129 | +136 | +39 | +27 | +37 | +3 |
| 99-kDa HEP-G-CSF | −3 | −13 | +125 | +124 | +35 | +20 | +15 | −9 |
| NEULASTA ®* | −12 | +6 | +181 | +213 | +29 | +20 | +16 | NC |

Note:
n = up to 5/group;
NC = No change;
+= increase;
−= decrease
*NEULASTA ® (pegfilgrastim, Amgen Inc., Thousand Oaks, CA)

A long-term immunological study for examining if there was potential induction of anti-HEP immunoglobulins (either IgM or IgG) by treatment with the HEP-G-CSF (reductive amination method) was performed. Three male Sprague Dawley rats were repetitively injected with a HEP-drug conjugate (55-kDa HEP-G-CSF at 0.4-0.7 mg/kg on weeks 1, 4, 7, 10, and 13; performed at SDIX LLC, Newark, Del.). The presence of antibodies against heparosan was examined by ELISA with blood collected on week 9 or 15. Amine-binding maleic anhydride plates (Thermo Fisher Scientific Inc., Rockford, Ill.) were coated with various test antigens in triplicate. The experimental wells were coated with 55 kDa heparosan amine (200 µL at 0.1 mg/mL). As negative controls, other wells were also coated in parallel with 200 µL of 100 mM Tris or 0.1 mg/ml hyaluronan-amine (prepared at Caisson Biotech LLC, Oklahoma City, Okla.) of similar molecular weight. After 4-6 hours incubation at room temperature, the plates were washed with PBST (0.05% TWEEN® 20 in PBS; Amresco LLC, Solon, Ohio) and blocked for overnight with 1% bovine serum albumin (BSA; Promega Corp., Madison, Wis.) in PBST.

Figure 13:
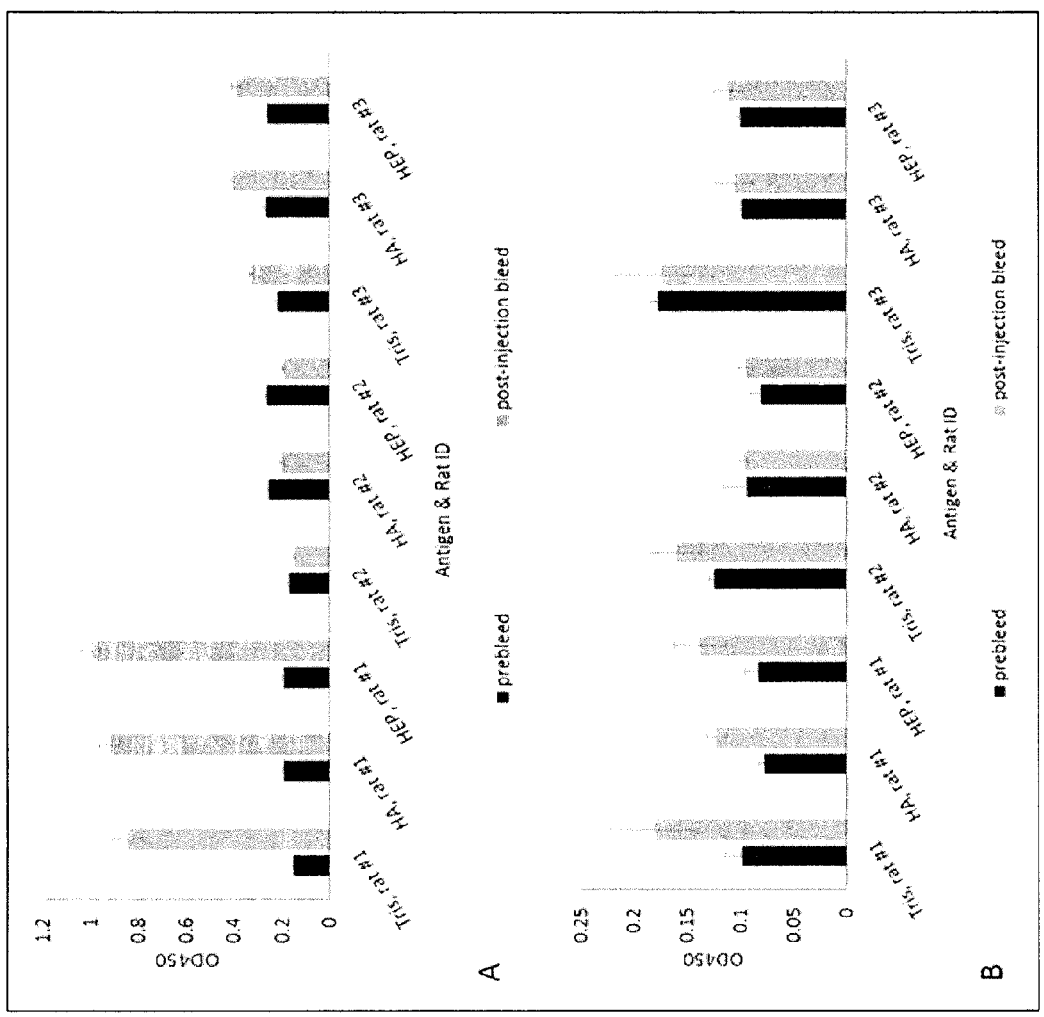
FIG. 13 depicts the serological test results for potential induction of anti-HEP antibodies in HEP-G-CSF boosted rats. ELISA wells were coated with Tris (background control), hyaluronic acid (HA; a close structural analog of heparosan serving as a negative control), or heparosan (HEP). After blocking the wells with BSA and washing thoroughly, 4 μl (for anti-HEP-IgG detection) or 1 μl (for anti-HEP-IgM detection) of the pre- or post-immunization serum, collected on week 15 after 5 boosts with HEP-G-CSF, was incubated in the well. The presence of any rat antibodies against polymer was determined by binding of a goat anti-rat horseradish peroxidase enzyme secondary reagent: either anti-rat IgG (Xa; 1:15,000) (Panel A) or anti-rat IgM secondary antibody (Xb; 1:50,000) (Panel B) and the use of a colorimetric substrate detectable at 405 nm. The individual bars on the histogram are labeled "antigen, rat #," which encodes if the well was coated with Tris, HA, or HEP and which rat #1, #2 or #3 was sampled; each bar corresponds to an averaged triplicate well determination. Even after multiple boosts with the HEP-drug conjugate, no specific antibodies against heparosan were observed (i.e., no significant differences between signals of the HEP and the controls HA or Tris).

The wells were then incubated with 0.5-5 µL of serum (either from the pre-immunization bleeds or from bleeds post-dosing with HEP-drug) for a 2-3 hour incubation at room temperature. After another washing step of repeated PBST buffer rinses to remove unbound molecules, either one of the two detection horseradish peroxidase-conjugated goat-derived polyclonal reagents were added to the wells: (a) anti-rat IgG or (b) anti-rat IgM (Thermo Fisher Scientific Inc., Rockford, Ill.), and the plates were incubated for 2 hours. After final washing with PBST without sodium azide, a colorimetric substrate solution (TMB Substrate Kit, Thermo Fisher Scientific Inc., Rockford, Ill.) was added. After 15-30 minutes, the reaction was stopped with 2M $H_2SO_4$, and the intensity of the color was measured by a spectrophotometric plate reader at a wavelength of 450 nm. The serum and secondary antibody were both diluted by the desired factor with 1% BSA in PBST, and 2004 was added per well. The HEP-G-CSF did not spawn a specific antibody (IgM, IgG) response to the heparosan molecule, even after five boosts of the HEP-drug conjugate (FIG. 13).

Example 3

Heparosan-Polypeptide
Conjugates—HEP-Interferon (INF)

Interferons (INF) are a class of proteins that were initially described as factors that stimulate the body to fight viral infections, but more forms of interferons have been shown to have other actions in the body as well. Some interferons have applications in treating hepatitis or promise in cancer treatment. Typically, interferon alone needs multiple injections to have a biological affect; thus, protractors such as polyethylene glycol (PEG) have been coupled to interferon (e.g., PEGINTRON® (peginterferon alfa-2b, Merck & Co., Inc., White House Station, N.J.) or PEGASYS® (peginterferon alfa-2a, Genentech USA, Inc., South San Francisco, Calif.)) and used to increase the half-life, thus needing just one injection.

In one non-limiting example, the reducing-terminal aldehyde of t h e 70-kDa heparosan chain is coupled to the amino-terminus of human interferon alpha 2b (recombinant *E. coli*; Insight Genomics) via reductive amination with cyanoborohydride at ~pH 5-6 (typically in an acetate buffer system at 0-37° C. for 0.1-24 hours, but other buffers, incubation temperature and times, reducing agents and different pH ~4.5 to 7, will also work). The HEP-interferon conjugate was purified by gel filtration chromatography. Various sizes of heparosan (i.e., different polymer chain lengths, such as the heparosan polymers having a mass ranging from about 600 Da to about 4,500 kDa; measured in Da=Daltons to kDa=thousands of Daltons) are coupled to the protein.

Figure 14:
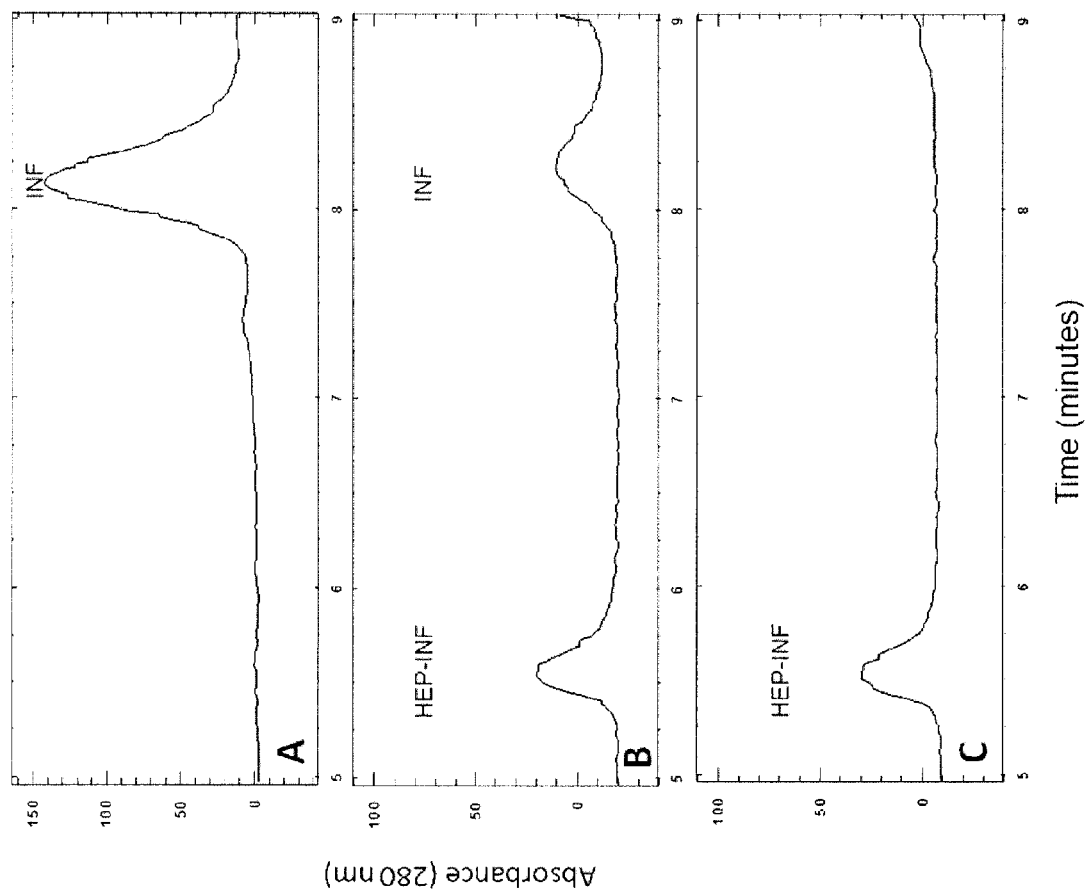
FIG. 14 depicts gel filtration chromatography profiles of interferon (INF) and HEP-INF conjugate. A) pure interferon; B) HEP-INF conjugate reaction mixture; C) purified HEP-INF conjugate. The target HEP-drug conjugate was formed.

The gel filtration chromatography (PolySEP™ column (Phenomenex, Inc., Torrance, Calif.) run in 50 mM HEPES, 0.15 M NaCl, pH 7.2) profiles monitoring the protein component (via absorption at 280 nm where this heparosan reagent does not strongly absorb) of the starting interferon alone (elutes at ~8.2 minutes), the reaction mixture of heparosan-aldehyde with interferon (contains both product molecule as well as some uncoupled interferon), and the purified heparosan-interferon conjugate (elutes at ~5.5 minutes) are shown in FIG. 14 (panel A, B, and C, respectively).

Figure 15:
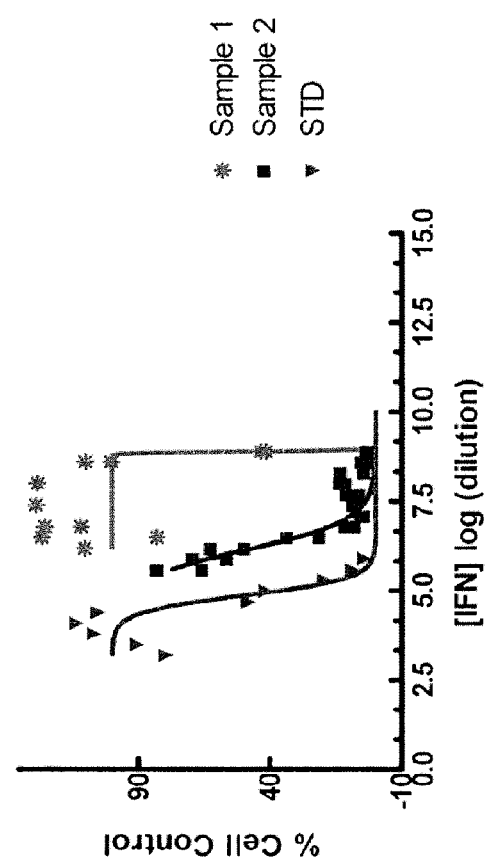
FIG. 15 depicts a plot detailing a viral challenge assay of interferon (INF) and HEP-INF conjugate. Data was analyzed in Graph Pad Prizm software (Graph Pad Software, Inc., La Jolla, Calif.) using a sigmoidal fit (variable slope). The interferon standard (STD), the interferon was subjected to the same purification processing (Sample 2; this mock-treated standard shows some loss of activity during handling), or the HEP-interferon conjugate (Sample 1). The HEP-drug conjugate had antiviral activity.

The purified HEP-interferon conjugate was tested for an in vitro viral challenge/cell proliferation assay (performed by CRO, PBL Interferon Source, Inc., Piscataway, N.J.), as shown in FIG. 15. Human A549 cells were challenged with a dose of encephalomyocarditis virus that kills all the cells in 40 hours in the absence of IFN. Plates were stained with Crystal Violet, a visual cytopathic effect assay was performed, and the dye was then solubilized, and absorbance was read. This data was then analyzed in Graph Pad Prizm (Graph Pad Software, Inc., La Jolla, Calif.) using a sigmoidal fit (variable slope). The interferon standard (STD), the interferon subjected to the same processing as the HEP-interferon (Sample 2), and the HEP-interferon conjugate (Sample 1) possessed activity protecting the cells from death, the desirable therapeutic effect.

Example 4

Heparosan-Peptide Conjugates—HEP-Insulin

Insulin is a peptide hormone that helps maintain glucose homeostasis and is employed in diabetes treatment. Typically, insulin alone needs multiple injections to have a biological effect; thus, long-acting versions are also needed for patient treatment.

In one non-limiting example, the reducing terminal aldehyde of 55-kDa heparosan chain (HEP-CHO or HEP-Al) was coupled to one of the amino-terminus of human insulin (recombinant yeast; Sigma-Aldrich, St. Louis, Mo.) via reductive amination with sodium cyanoborohydride (Sigma-Aldrich, St. Louis, Mo.) at ~pH 5-6 (typically in an acetate buffer system at 0-37° C. for 0.1-24 hours, but other buffers, incubation temperature and times, reducing agents, and different pH ~4.5 to 7, will also work). The molar ratio of HEP reagent (55-kDa HEP-CHO) and insulin in the derivatization reaction ranged from ~2:1-4:1, with the concentration of insulin at 0.4-2 mg/mL. Various sizes of heparosan (i.e., different polymer chain lengths, such as the heparosan polymers having a mass ranging from about 600 Da to about 4,500 kDa are coupled to the protein. Roughly 40-50% of the insulin was modified with HEP when a 2- or 4-fold excess of HEP reagent was used.

Figure 16:
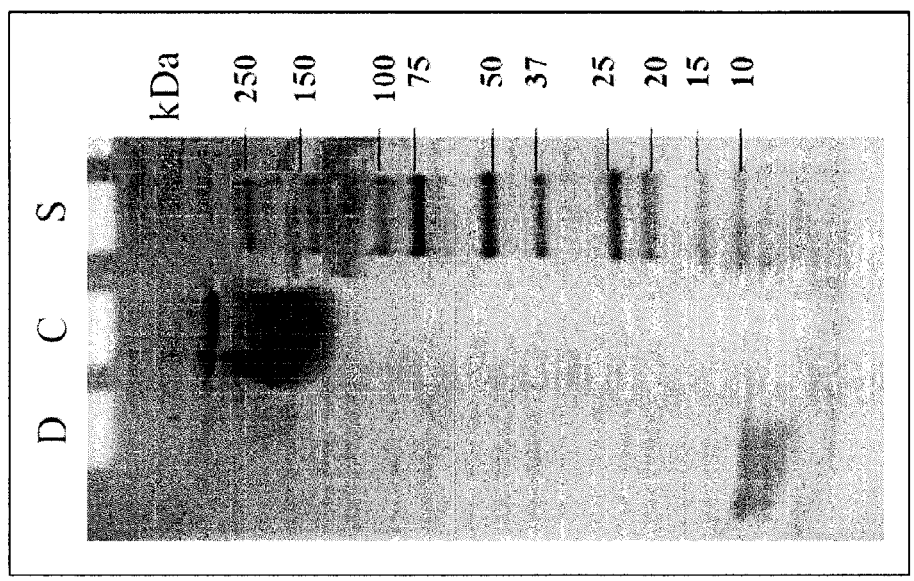
FIG. 16 depicts a SDS-polyacrylamide gel analysis of insulin (lane D), and HEP 55-kDa conjugated to insulin (lane C) using aldehyde activated heparosan, and protein MW standard (lane S) (molecular masses are indicated). The HEP-insulin conjugate was formed.

The HEP-insulin conjugate was purified by ion exchange chromatography with HiTrap® Q Sepharose High Performance column (GE Healthcare Bio-Sciences AB LLC, Uppsala, Sweden) pre-equilibrated with a pH 5~7 buffer (buffer A). HEP-insulin conjugate was separated from uncoupled free insulin by elution with a linear gradient to 50% of buffer B (1M NaCl in buffer A) over 20 CVs (column volumes). Fractions containing the conjugate were pooled, concentrated, and exchanged into an insulin storage buffer (2 mg/mL m-cresol and 5 µg/ml ZnCl₂, pH ~7) or PBS (Amresco LLC, Solon, Ohio) in spin units with molecular weight cut off of 3 kDa (Amicon, Darmstadt, Germany). The conjugate solution was then sterile filtered through 0.2 µm spin filter units (Corning Inc., Tewksbury, Mass.), aliquoted, and stored at ~4° C. All conjugate concentration indicated in this example are the concentration of protein (i.e., based on an insulin standard) determined with Bradford Assay. The 4-20% SDS-PAGE gel profile of free insulin and the HEP-insulin conjugate (C) are demonstrated in FIG. 16; the free insulin runs fast on the gel due to its small size, while the conjugate with a 55 kDa heparosan chain covalently attached migrates more slowly due its higher molecular weight.

Figure 17:
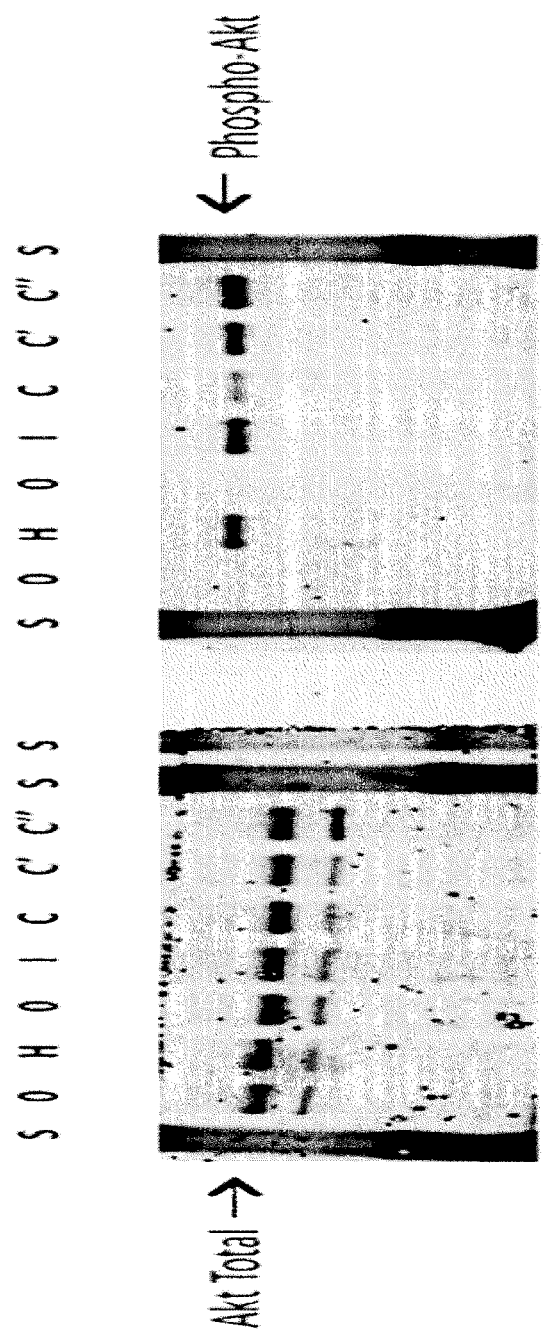
FIG. 17 shows in vitro Signaling Assay results of Insulin (I, H) and 55-kDa HEP-insulin Conjugate (C). Right panel: anti-tyrosine phosphate Western blot detecting the phospho-AKT band (marked with arrow) produced via signaling event. Left panel: anti-AKT kinase Western blot detecting total AKT species (a loading control blot which indicates even sample loading was achieved in all lanes). The lanes are designated as follows: S, Benchmark protein pre-stained molecular weight standards, Invitrogen; 0, buffer negative control; H, 10 nM HUMULIN®-treated (concentrated insulin; Eli Lilly and Company, Indianapolis, Ind.); I, 10 nM insulin-treated; C, C', and C" are 10, 100, 1000 nM HEP-insulin conjugate-treated, respectively. The HEP-drug conjugate was active as a hormone to trigger mammalian cell signaling.

The resulting purified conjugates were tested with an in vitro cell signaling assay as shown in FIG. 17. On Day 1, 3T3L1 adipocytes were treated with the HEP conjugates or insulin (either HUMULIN® (concentrated insulin; Eli Lilly and Company, Indianapolis, Ind.) or the Sigma-Aldrich (St. Louis, Mo.) starting insulin material used in the HEP coupling reaction) or buffer alone. On Day 2, the cells were lysed in a phosphatase-inhibitor and protease inhibitor solution, the protein content of the lysates were measured by the Bradford assay to assure loading normalization between samples, and samples of the lysates (10 micrograms of protein/lane) were run on duplicate SDS-PAGE gels. The separated proteins were analyzed by Western blotting with immunoreagents specific for insulin receptor, for AKT kinase, or for phospho-tyrosine. The HEP-insulin conjugate activated cellular signaling pathways in a similar pattern to free insulin; the appearance of the phosphorylated AKT kinase (phospho-AKT) is a hallmark of insulin signaling.

The HEP-insulin conjugate was tested in an animal model in vivo where the blood glucose concentration was decreased by the effect of insulin (performed by Xenometrics, LLC, Stilwell, Kans.). Male CD-1 mice (20-25 g each; ~7 weeks old) were split into groups of n=5 mice each and given a single subcutaneous dose of 1 unit/kg of a long-acting insulin test solution (either HEP-insulin or LANTUS® (insulin glargine, Sanofi US, Bridgewater, N.J.) or LEVEMIR® (insulin detemir, Novo Nordisk Inc., Plainsboro, N.J.)) or a vehicle control following a three hour fast. At various time points, the mice were bled via tail nick to provide blood for glucose level determination. Readings (mg/dL) were taken in duplicate using a commercially available glucose meter over a 12 hour experimental period, with food being returned following the 7 hour reading. The blood glucose levels were normalized to the vehicle control (set at 100%).

Figure 18:
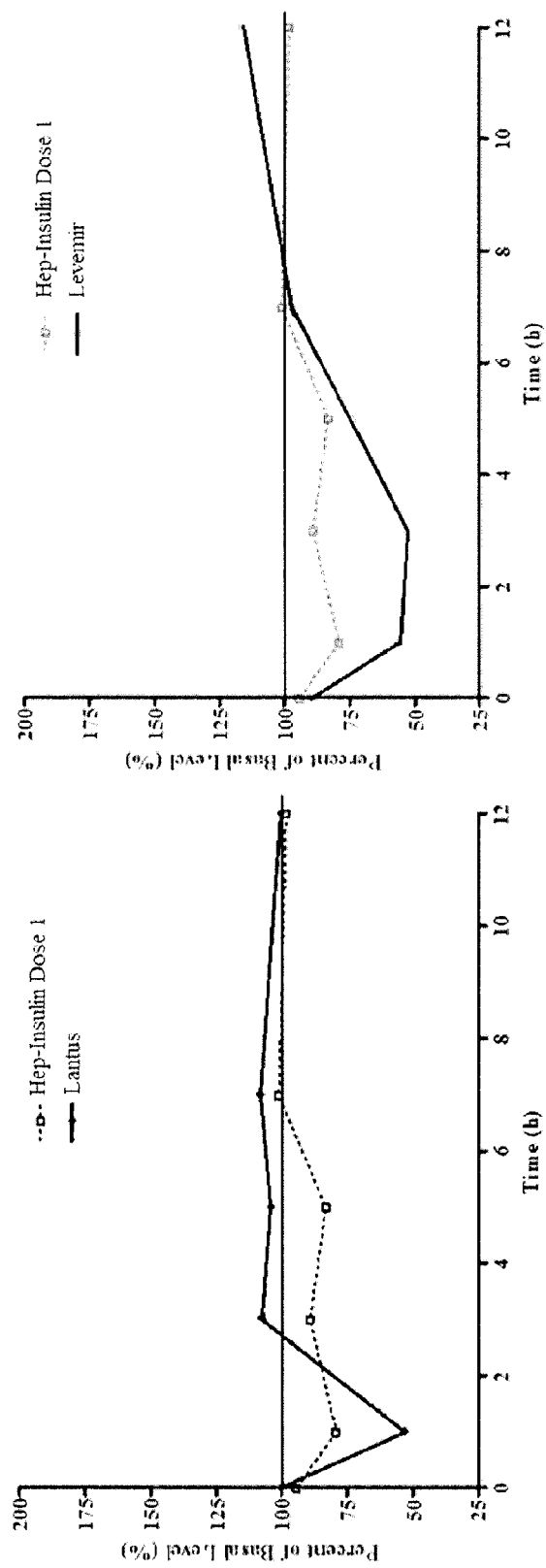
FIG. 18 depicts a line graph detailing an in vivo assay of glucose blood levels in mice post-dosing with insulin and conjugates. Long-acting commercial insulins (LANTUS® (insulin glargine, Sanofi US, Bridgewater, N.J.) or LEVEMIR® (insulin detemir, Novo Nordisk Inc., Plainsboro, N.J.) or a 55-kDa HEP-insulin conjugate was injected into normal mice. At various times post-dosing, blood samples were drawn and assayed for glucose concentration. The line set to 100% is the normalized basal level of glucose in the bloodstream in the vehicle control. The HEP-drug conjugate was active as a hormone to alter blood glucose levels in a sustained fashion (i.e., long-acting) in mammals.

Based on the percent change of glucose readings over time, the long-acting insulin-related test articles outperformed insulin in reducing glucose levels in the blood (FIG. 18). In this test, HEP-insulin performed at an intermediate level between two FDA-approved long-acting insulins on the market.

Figure 19:
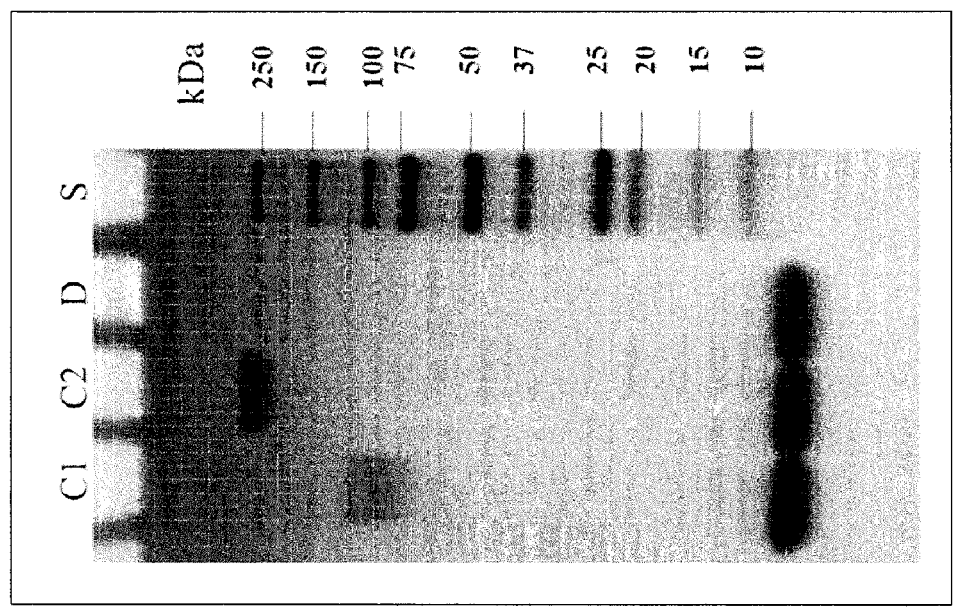
FIG. 19 depicts a SDS-polyacrylamide gel analysis of HEP-insulin conjugate. The conjugation reaction was made using HEP-monosquaramide polymers (26 or 75 kDa). The lanes from left to right: 26-kDa HEP conjugated to insulin (C1), and 75-kDa HEP conjugated to insulin (C2), free insulin (D), and the protein MW standard (S) (molecular masses are indicated).

In other non-limiting examples, the reducing terminal monosquaramide of 26- or 75-kDa heparosan chain was coupled to the amino terminus of recombinant human insulin (recombinant yeast; Sigma-Aldrich, St. Louis, Mo.). Conjugation reactions were performed at pH 9.0 in 75 mM sodium borate buffer at 0-37° C. for 0.1-72 hours (but other buffers with pH ranges from 8.5-9.5, other incubation times, and different molar ratios). For example, one molar equivalent of HEP-monosquaramide was reacted with 10 molar equivalents of insulin. The 4-20% SDS-PAGE gel shows free insulin and HEP-insulin conjugates (FIG. 19).

Figure 20:
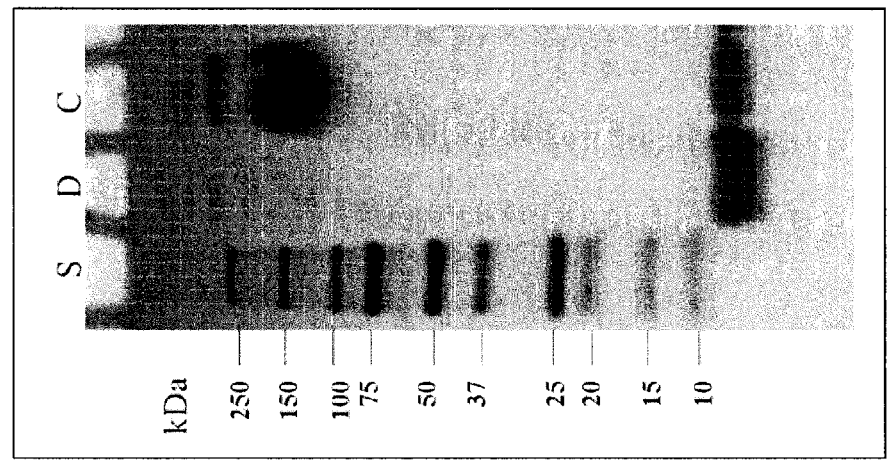
FIG. 20 depicts a SDS-polyacrylamide gel analysis of HEP-insulin conjugate stained with PageBlue™ protein staining solution (Thermo Fisher Scientific Inc., Rockford, Ill.). Insulin was conjugated to a branched heparosan polymer (i.e., one linker with 2 chains of 42-kDa HEP) via reactive amination. The gel shows the protein MW standard (lane S), free insulin (lane D), and HEP-insulin conjugate (lane C).

In another non-limiting example, the reducing terminal aldehyde of a branched crosslinker containing two 42-kDa heparosan chains was coupled to the amino-terminus of recombinant human insulin (recombinant yeast; Sigma-Aldrich, St. Louis, Mo.) via reductive amination with sodium cyanoborohydride (Sigma-Aldrich, St. Louis, Mo.) at ~pH 5-7 (typically in an acetate buffer system at 0-37° C. for 0.1-24 hours, but other buffers, incubation temperature and times, reducing agents and different pH ~4.5 to 7, will also work). For example, molar equivalent ratio of insulin:HEP was reacted (200 mM sodium acetate, pH 5.5, 100 mM sodium cyanoborohydride) at room temperature for 72 hours (FIG. 20).

Example 5

Heparosan-Polypeptide Conjugates—HEP-Human Growth Hormone (hGH)

hGH is a protein that stimulates growth and has applications in treating height deficits from various causes. Typically, hGH alone needs multiple injections to have a biological effect. In addition to the stimulatory growth factors or drugs or drug candidates (e.g., agonists), inactive or inhibitory versions of drugs or drug candidates (e.g., antagonists) are also useful therapeutics; heparosan conjugates also enhance their efficacy.

Figure 21:
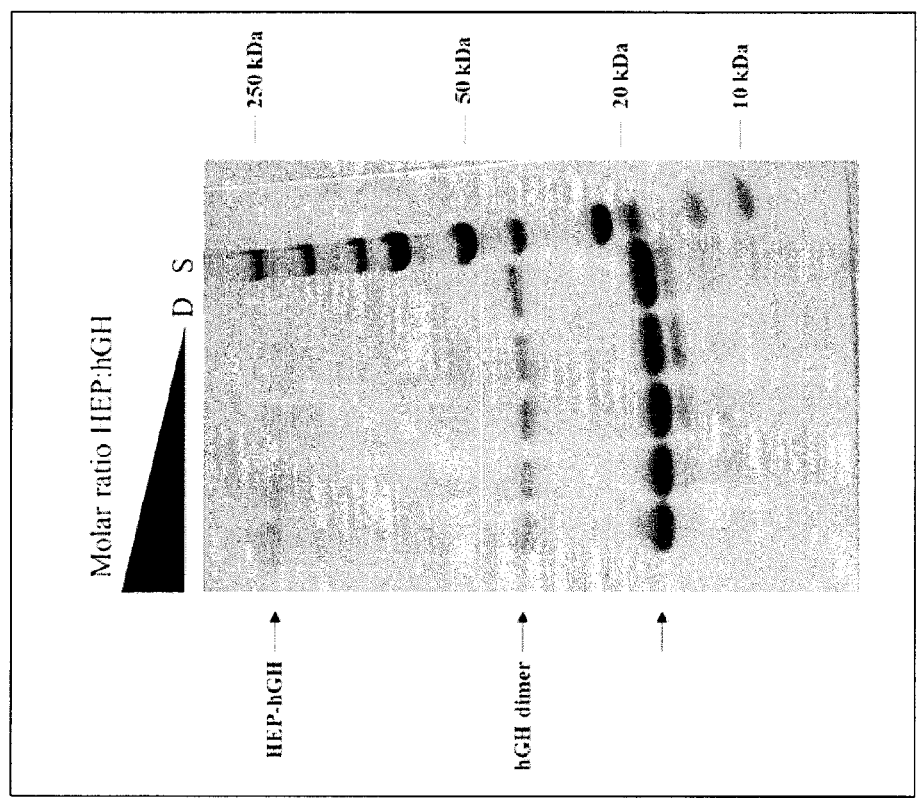
FIG. 21 depicts a SDS-polyacrylamide gel analysis, stained by PageBlue™ protein staining solution (Thermo Fisher Scientific Inc., Rockford, Ill.), of human growth hormone (hGH) and HEP-hGH conjugate. The hGH was incubated with different molar ratios of 55-kDa HEP aldehyde (HEP-CHO; from left to right: 12, 8, 4, and 2 molar ratio HEP:hGH); free hGH (D); protein MW standard (S). The target HEP-drug conjugate was formed.

In one non-limiting example, the reducing-terminal aldehyde of 55-kDa and 99-kDa heparosan chain (HEP-CHO) was coupled to the amino-terminus of hGH (recombinant E. coli; ProSpec-Tany TechnoGene Ltd., East Brunswick, N.J.) via reductive amination with sodium cyanoborohydride (Sigma-Aldrich, St. Louis, Mo.) at ~pH 5-6 (typically in an acetate buffer system at 0-37° C. for 0.1-24 hours, but other buffers, incubation temperature and times, reducing agents and different pH ~4.5 to 7, will also work). The molar ratio of HEP reagent (55-kDa HEP-CHO) and hGH in the derivatization reaction ranged from ~2-4:1, with the concentration of hGH at 0.4-2 mg/mL. Various sizes of heparosan (i.e., different polymer chain lengths, such as the heparosan polymers having a mass ranging from about 600 Da to about 4,500 kDa) were coupled to the protein. In FIG. 21, various amounts of HEP-CHO (from 2- to 12-molar equivalents over protein) were reacted with the protein. SDS-PAGE gel (FIG. 21) shows the HEP-conjugate running at a higher molecular weight than the hGH alone.

Example 6

Heparosan-Peptide Conjugates HEP-Glucagon-Like Peptide-1 (GLP-1)

GLP-1 is a member of the "glucagon peptide family" and is derived from the expression of the preproglucagon gene located on chromosome 17. GLP-1 is released from the neuroendocrine L-cells in two forms: GLP-1 (7-36) amide (80% of circulating GLP-1) and GLP-1 (7-37) amide. It is capable of stimulating insulin secretion and is used for the treatment of type 2 diabetes. The rapid degradation of GLP-1 by the enzyme dipeptidyl peptidase-4 (DPP-IV) has led to the development of degradation-resistant GLP-1-receptor agonists. GLP-1 derivatives with prolonged half-life will benefit diabetes patients.

Figure 22:
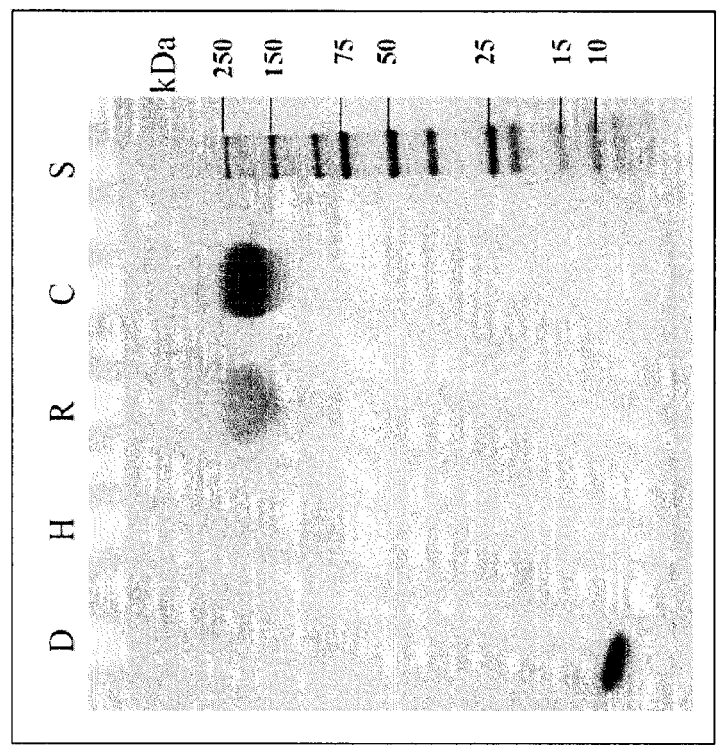
FIG. 22 depicts a SDS-polyacrylamide gel analysis of HEP-GLP-1 conjugate. Lanes: 5 µg of free GLP-1 (D); 55-kDa heparosan alone (H); HEP-GLP-1 reaction mixture prior to purification (R); purified 55-kDa HEP-GLP1 conjugate (C) (2.5 µg based on GLP-1 content); protein MW standard (S). The target HEP-drug conjugate was formed.

In one non-limiting example, the reducing-terminal maleimide of the heparosan chain was coupled to the free thiol of C-terminal end of GLP-1 analog sequence. The GLP-1 analog peptide has a sequence of 7-HGEGTFTSD- VSSYLEGQAAKEFIAWLVRGRGGSGGSC synthesized by GenScript USA Inc. (Piscataway, N.J.). Comparing with the native GLP-1 (7-37) sequence, Alanine 8 was replaced with Glycine to increase its DDP-IV-resistance. Lysine 34 was replaced with Arginine to reduce its susceptible to serine proteases. At the carboxyl-terminus, amino acid sequence of GSGGSC was added to facilitate conjugation of heparosan-maleimide to the terminal Cysteine. A solution of this GLP-1 analog was added to a tube containing lyophilized HEP-Maleimide polymer. The final reaction contained 1 mg/mL GLP-1, 50 mM phosphate, pH 7.0, and 5 mM EDTA. The molar ratio of HEP reagent (55-kDa HEP-Maleimide) and GLP-1 peptide in the derivatization reactions ranged from ~1:1 to 2:1. The reaction was incubated at room temperature for about 16 hours (FIG. 22). Roughly 80-90% of the GLP-1 was modified with HEP. The separation of HEP-GLP-1 conjugate from unreacted GLP-1 was achieved by SAX with Q Sepharose HP column (GE Healthcare Bio-Sciences AB LLC, Uppsala, Sweden) using GE's AKTA Explorer system. Column was pre-equilibrated with 10 mM HEPES, pH 7.2 (buffer A), and the conjugate was eluted with a linear gradient to 50% of buffer B (1M NaCl in buffer A) over 20 CVs. The fractions having an absorbance at 280 nm were analyzed by SDS-PAGE, and the drug conjugate-containing eluates were concentrated and exchanged into phosphate-buffered saline (PBS, Amresco LLC, Solon, Ohio) in spin units with molecular weight cut off of 3 kDa (Amicon, Darmstadt, Germany). The conjugate solution was then sterile filtered through 0.2 μm COSTAR® spin filter units (Corning Inc., Tewksbury, Mass.), aliquoted and stored at −80° C. All conjugate concentration indicated in this example are the concentration of protein (i.e., GLP-1) determined with Bradford Assay.

Example 7

Heparosan-Polypeptide Conjugates—HEP-Antibody and HEP-Antibody Fragments

Antibodies (or immunoglobulins) are proteins that bind antigens and have applications in treating various diseases. In many cases, fragments of antibodies (e.g., F(ab')2, Fab', Fab, etc.) genetically or enzymatically generated, or naturally small immunoglobulins (e.g., cameloid), are desirable to remove the Fc functionality (which binds to white blood cells, complement, etc.) and/or allow better tissue/cellular penetration, and/or simplify manufacture. Typically, treatment with a Fab alone requires multiple injections and/or a protracting technology to have a biological effect due to short half-life concerns. As an example, anti-TNF-alpha Fab' conjugated to a 40 kDa polyethylene glycol (PEG), CIM-ZIA® (certolizumab pegol, UCB, Inc., Atlanta, Ga.), is used for the treatment of moderate to severe Rheumatoid Arthritis (RA).

In some non-limiting examples, the reducing-terminal sulfhydryl-reactive group (iodoacetate or maleimide) of a 60-, 99- or 305-kDa heparosan chain was coupled to the free cysteine group of a reduced Fab' fragment. The coupling reactions are typically in neutral to slightly alkaline buffers (e.g., phosphate or HEPES at ~pH 6 to 8.5 at 0-37° C. for 0.1-24 hours), but other buffers, incubation times, and higher pH will also work as long as no sulfhydryl groups besides the target for coupling and preferably no primary amines are present. Various sizes of heparosan (i.e., different polymer chain lengths, such as the heparosan polymers having a mass ranging from about 600 Da to about 4,500 kDa) were coupled to the protein. The Fab' example here is derived from murine anti-human TNF-alpha IgG (recombinant human protein expressed in *E. coli*; BioLegend, San Diego, Calif.) that was subjected to protease digestion and reduction using mild reducing agents (e.g., β-mercaptoethylamine, β-mercaptoethanol, DTT, etc.). Due to the light sensitivity of iodoacetate, the conjugation reaction was performed in the dark. Typically the drug and the HEP were mixed together (drug:HEP in molar ratio ranging from ~1:0.2 to 1:10) and were left to react for about 16 hours with mild shaking.

Figure 23:
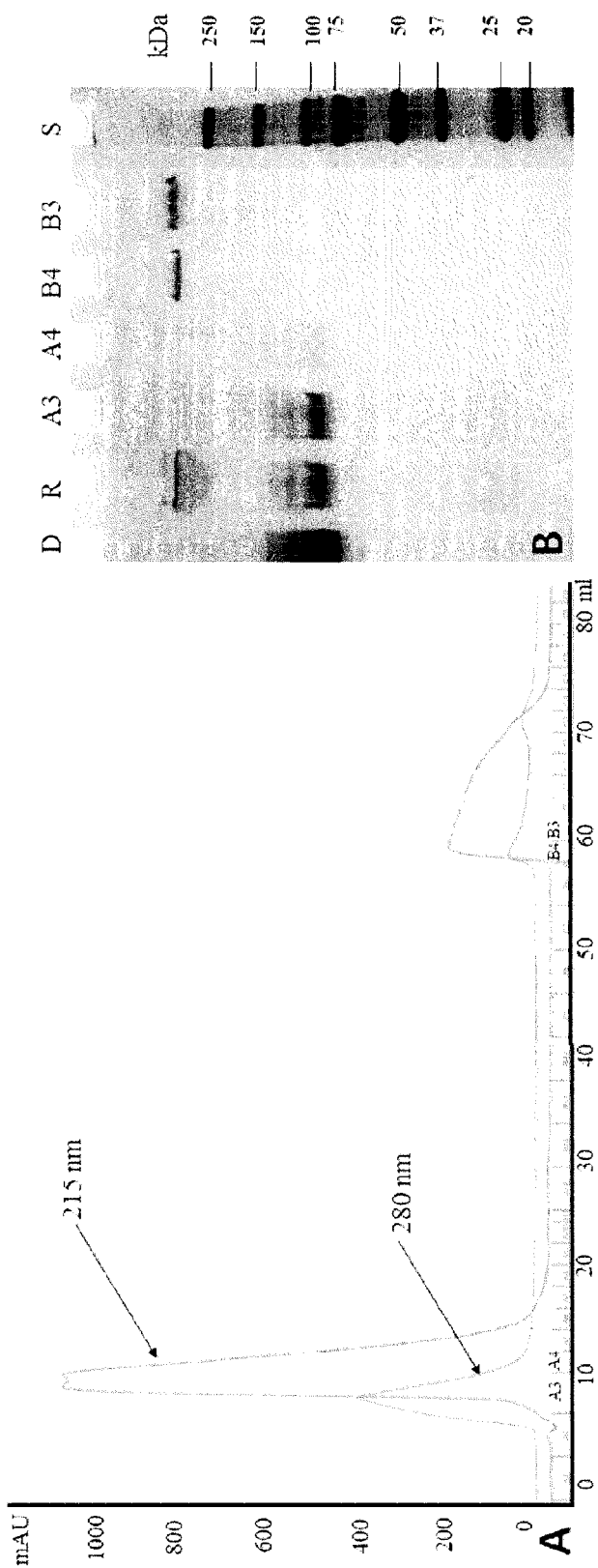
FIG. 23 depicts a profile of a strong anion exchange (SAX) chromatographic purification of a HEP-Fab' conjugate. Panel A: UV trace profile (280 nm for protein; 215 nm for protein and polysaccharide) of the SAX chromatography purification step eluted with a gradient of increasing NaCl concentration. Panel B: SDS-polyacrylamide gel (4-15% gel with staining with PageBlue™ protein staining solution (Thermo Fisher Scientific Inc., Rockford, Ill.)) of the resulting fractions. From left to right: anti-TNFα Fab' (D); 99 kDa HEP-Fab' reaction mixture (R); fractions A3, A4, B4, or B3. The target HEP-drug conjugates were observed in Fractions B4 and B3.

The HEP-Fab' conjugates were purified by anion exchange chromatography using HiTrap® Q Sepharose High Performance resin (GE Healthcare Bio-Sciences AB LLC, Uppsala, Sweden) pre-equilibrated with HEPES buffer at neutral pH (buffer A). HEP-Fab' conjugate was separated from uncoupled free Fab' by elution with a linear gradient to 50% of buffer B (1M NaCl in buffer A) over 20 CVs (other chromatography resins and buffers could be also used) (FIG. 23A). HEP-Fab' conjugate recovered after anion exchange chromatography was analyzed by SDS-PAGE gel (FIG. 23B); for example, 99-kDa HEP with iodoacetate reactive group was conjugated to Fab'. Roughly 75% of the Fab' was modified with HEP when a ~10-fold excess of HEP reagent was used.

Figure 24:
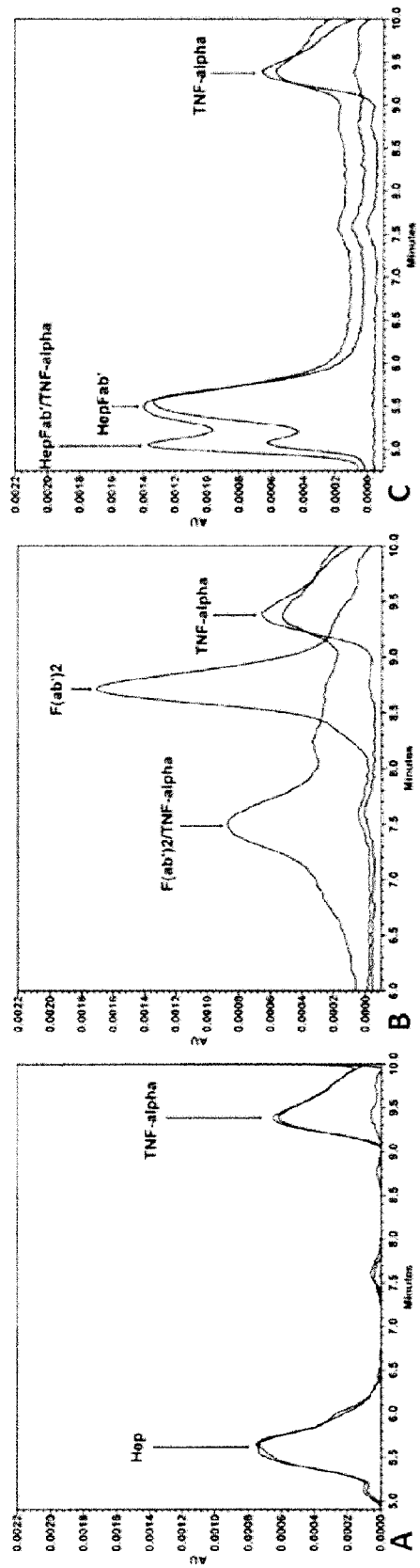
FIG. 24 depicts the chromatographic profiles of the determination of HEP-antiTNF-alpha Fab' conjugate binding activity or its TNF-α target. HPLC-SEC analysis (280 nm detection) of HEP, human anti-TNF-alpha F(ab')$_2$, or HEP-Fab' conjugate incubated in the absence or in the presence of TNF-α. Panels: A, HEP; B, F(abl$_2$; C, HEP-Fab' conjugate. The loss of some material from the free TNF peak (~9.4 minutes elution) and the creation of new higher molecular weight complex indicated by faster eluting peaks (i.e., ~7.5 min in Panel B or ~5.2 min in Panel C) show that TNF was bound by the antibody fragment in free or HEP-modified forms. The HEP-drug conjugate had binding activity against its therapeutic target in mammals.

Biological activity of Fab' when conjugated to HEP was evaluated by assessing the binding of HEP-Fab' (HEP-anti TNF-alpha) to its target TNF-alpha (recombinant human TNF-alpha, Sino Biological Inc., Beijing, P.R. China); binding of the TNF by the antibody prevents this factor from acting in a detrimental fashion in the human body. HEP-Fab' conjugate was incubated in the presence of TNF-alpha in a molar ratio of 1:1 for 1 to 2 hours at room temperature with mild shaking to allow the binding of Fab' to target. The reactions were analyzed by HPLC-SEC (Bio SEC-3 or Bio SEC-5, Agilent Technologies, Santa Clara, Calif.) using 100 mM phosphate buffer pH 7.2 (other neutral buffers system will also work). The change in elution pattern observed by size exclusion chromatography at 280 nm showed that HEP-Fab' retains its binding properties for TNF-alpha (FIG. 24). Therefore, the HEP vehicle does not greatly hinder anti-TNF-alpha biological activity.

Example 8

Utility of Heparosan to Cloak or Mask Foreign or Non-Human Drugs or Drug Candidates Some enzymes are used therapeutically in cancer therapy or for the treatment of physiological disorders. However, their half-life can be shorter than optimal, and due to their production source (especially if microbial), they can be linked to allergic or immunological reactions. In order to increase half-life and reduce immunogenicity, some microbial enzymes have been conjugated with multiple polyethylene glycol (PEG) moieties. For example, native *E. coli* derived L-Asparaginase (Asp), modified by covalent attachment of multiple PEG chains per asparaginase units (about fourteen ~5-kDa PEG chains/protein). Pegaspargase (ON-CAPSPAR®, Sigma-Tau Pharmaceuticals, Inc., Gaithersburg, Mass.) is used as an anti-cancer including acute lymphocytic leukemia.

In a non-limiting example of the presently disclosed and/or claimed inventive concept(s), in order to "coat" the foreign protein surface with 'self' HEP chains, a two-step process is employed. First, Traut's reagent (2-iminothiolane hydrochloride; Pierce Biotechnology, Inc., Rockford, Ill.) was used to introduce sulfhydryl groups via modification of the primary amines of exposed lysine groups of the protein or the amino terminus; this modification process maintains the overall charge properties of the protein. Traut's reagent was reacted with various proteins in a buffer from pH 7 to 9 (a non-amine buffer must be employed, e.g. not Tris), in the presence low concentrations of EDTA, at 0-37° C., for 0.1-2 hours. Typically, prior to the thiolation step, the protein was exchanged by gel filtration into the reaction buffer. Traut's reagent was added to the reaction in various ratios to add new thiols. After this reaction, the unreacted reagent was removed by gel filtration before the HEP conjugation step.

Figure 25:
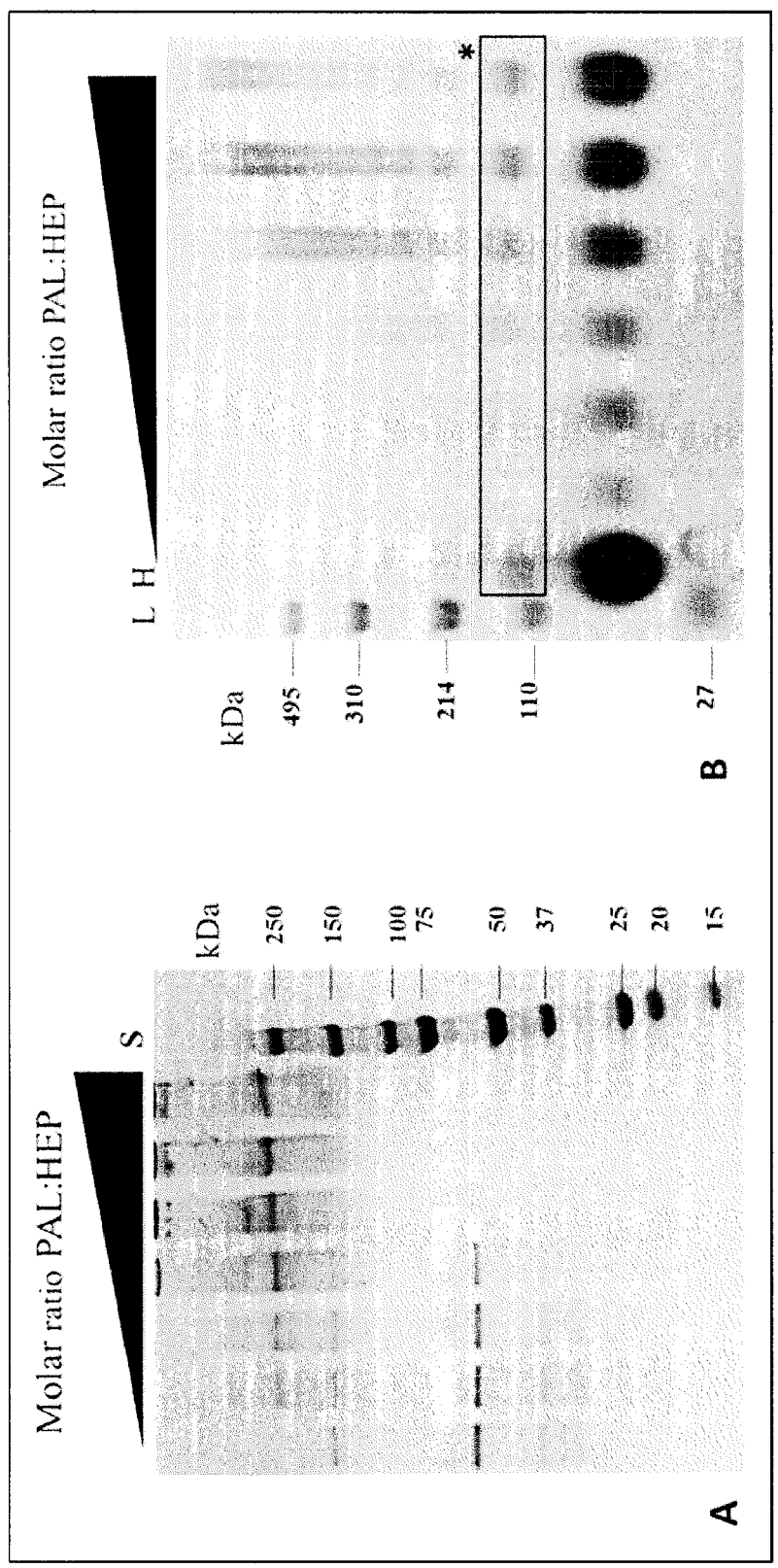
FIG. 25 depicts gel analysis of the conjugation of HEP to Phenylalanine Ammonia-Lyase (PAL) enzyme. PAL was incubated in the presence of increasing amount of activated HEP. The reaction mixtures were analyzed by either A) SDS-polyacrylamide gel 4-15% stained with PageBlue™ protein staining solution (Thermo Fisher Scientific Inc., Rockford, Ill.) or B) 2% agarose gel stained with Stains All. The PAL:HEP (molar ratio) from left to right was: 1:0, 1:0.2, 1:0.5, 1:1, 1:2.5, 1:5, or 1:10. The S and L lanes are the protein standards and Select HA (polysaccharide) ladder (Hyalose, LLC, Oklahoma City, Okla.), respectively. (*a contaminant found in this particular HEP batch). The target HEP-drug conjugates were formed; depending on the reaction conditions, various numbers of HEP chains were added to the enzyme.
Figure 26:
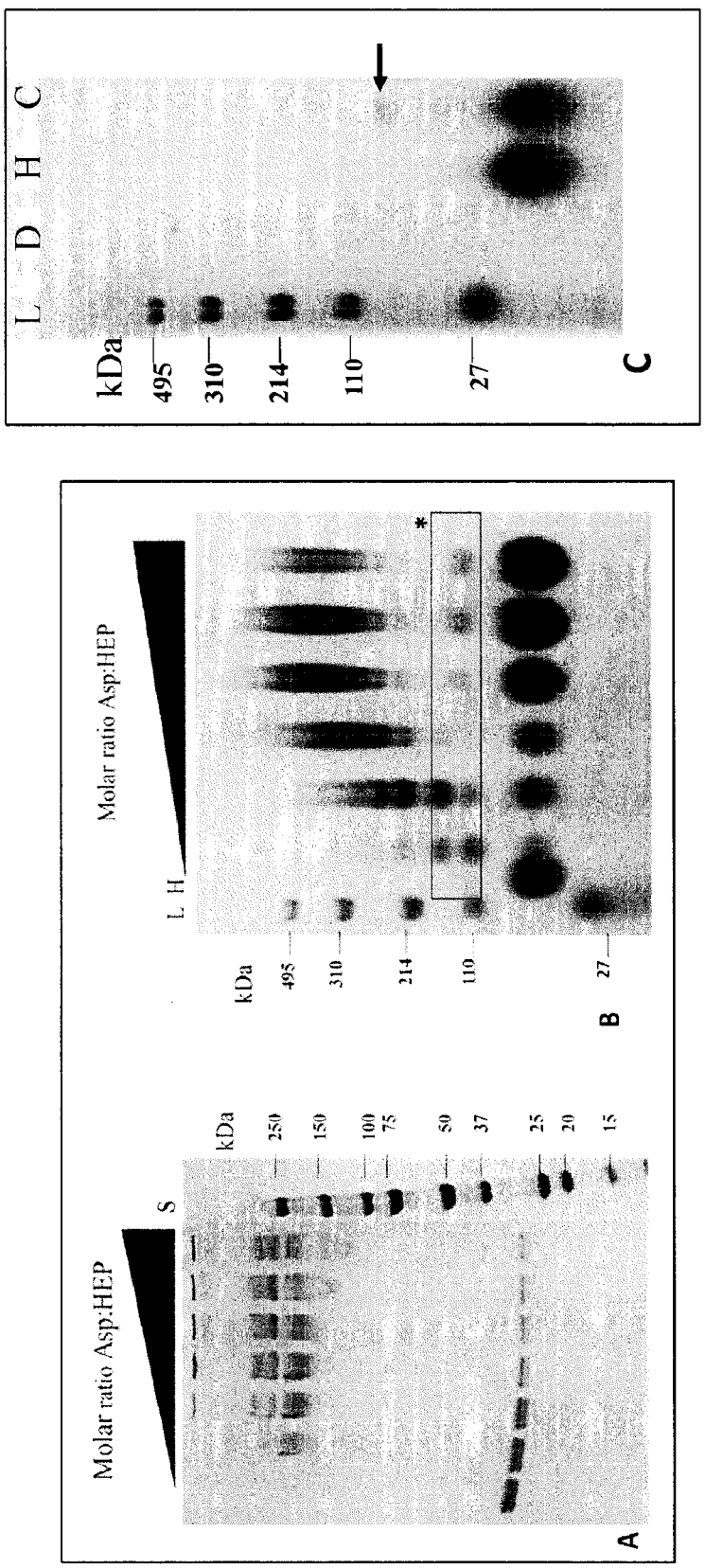
FIG. 26 depicts gel analyses of the conjugation of HEP to L-Asparaginase (Asp) enzyme. Asp was incubated in the presence of increasing amount of HEP. The reaction mixtures were analyzed by either Panel A) SDS-PAGE gel 4-15% stained with PageBlue™ protein staining solution (Thermo Fisher Scientific Inc., Rockford, Ill.) or Panel B) 2% agarose gel stained with Stains All. The Asp:HEP (molar ratio) from left to right was: 1:0, 1:0.2, 1:0.5, 1:1, 1:2.5, 1:5, or 1:10. Respectively S and L stand to protein standards and Select HA ladder (Hyalose, LLC, Oklahoma City, Okla.). (* a contaminant found in this particular HEP batch). In Panel C), a 2% agarose gel was used to analyze a reaction with 12-kDa heparosan (Lanes: D, Asp alone; HEP alone; C, drug conjugate mixture); the arrow marks the HEP-Asp conjugates with about 7 to about 9 chains. The target HEP-drug conjugates were formed; depending on the reaction conditions, various numbers of HEP chains were added to the enzyme.

Second, the coupling reactions employed heparosan with a reducing terminal sulfhydryl-reactive group (iodoacetate or maleimide) coupled to the chemically introduced free sulfhydryl group of the enzyme (from the first modification step above). These reactions are typically performed in neutral to slightly alkaline buffers (e.g., phosphate or HEPES at ~pH 6 to 8.5) at 0-37° C. for 0.1-24 hours (but other buffers, incubation times, and higher pH will also work as long as no sulfhydryl groups besides the target for coupling and preferably no primary amines are present). Various sizes of heparosan (i.e., different polymer chain lengths, such as the heparosan polymers having a mass ranging from about 600 Da to about 4,500 kDa) were coupled to the protein. The examples shown here used 12- or 55-kDa heparosan chains for coating the Phenylalanine Ammonia-Lyase (PAL) from *Rhodoturola glutinis* (Sigma-Aldrich, St. Louis, Mo.) or the L-Asparaginase (Asp) Type II from *E. coli* (ProSpec-Tany TechnoGene Ltd., East Brunswick, N.J.). Typically, reaction mixtures used enzyme:HEP molar ratios ranging from 1:0.2 to 1:10. The data showed that PAL (FIG. 25) and Asp (FIGS. 26A and B) were conjugated to 55-kDa HEP at multiple positions, or Asp (FIG. 26C) was conjugated to 12-kDa HEP at multiple positions. SDS-PAGE gel analysis indicates that multiple HEP chains were added to each protein molecule when higher HEP ratios were employed with a molar ratio enzyme (1:10); species with multiple HEP chains were detected per PAL subunit (FIG. 25A) or per Asp subunit (FIG. 26A). Roughly 50-75% of the PAL enzyme or ~100% of the Asp enzyme were modified with HEP when a 5- to 10-fold excess of HEP reagent was used. Analyses with 2% agarose gels indicates at least 10 HEP chains per PAL were added (FIG. 25B), while at least 9 HEP chains per Asp were added (FIG. 26B). Conjugates with more HEP chains could be produced if higher levels of the Traut's reagent and the HEP-reagent were employed.

Figure 27:
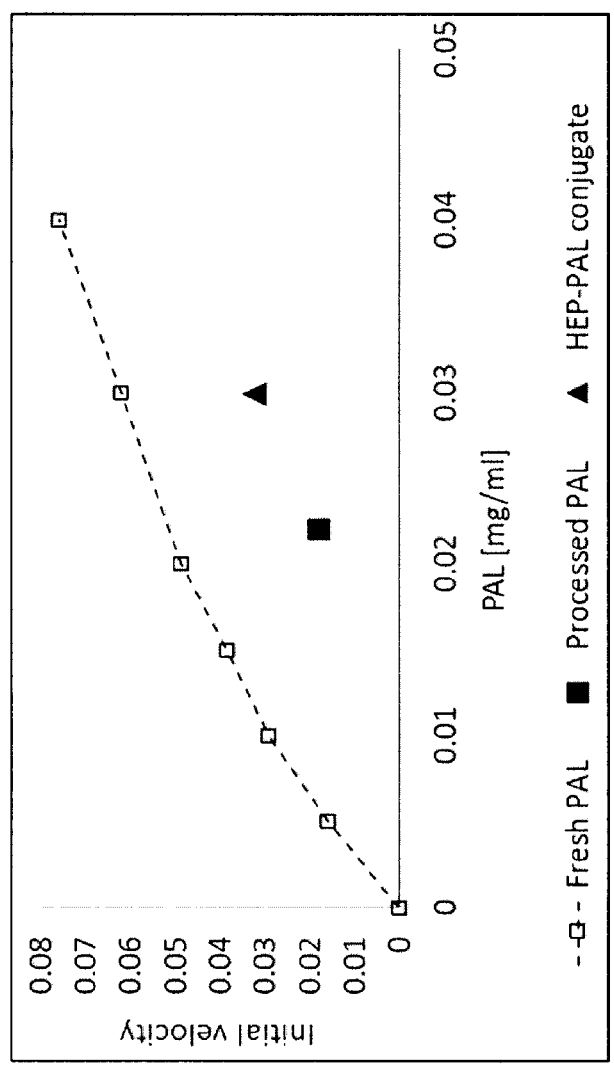
FIG. 27 depicts the kinetics profile of HEP-Phenylalanine Ammonia-Lyase conjugate activity. The enzymatic activity was evaluated by following the deamination of L-phenylalanine to trans-cinnamate and NH$_2$ at 290 nm at 30° C. The initial velocity of unconjugated 'fresh' PAL (ranging from 0 to 0.04 mg/mL) was used as reference for 100% activity. Based on protein content (Bradford assay), a known amount of processed PAL or PAL conjugated to HEP were assessed. Processed PAL and HEP-PAL conjugate were found to exhibit about 40% and about 45% of 'fresh' Asp activity, respectively. The target HEP-drug conjugates were active in destroying phenylalanine, the therapeutic action for treatment of PKU disease.

The enzymatic activity of the HEP-enzyme conjugates, the basis for their therapeutic use, was assessed. In this example demonstrating HEP-PAL activity, the 55-kDa HEP-drug conjugate was prepared by thiolation (Traut's reagent, room temperature for 1 hour), and the HEP coupling step (room temperature for 16 hours, 1:10 PAL:HEP) was used. Complete conversion of PAL into HEP-PAL was observed (FIG. 25A, lane 7). For PAL activity assays, the deamination of L-phenylalanine to trans-cinnamate and $NH_2$ was followed spectrophotometrically at 290 nm at 30° C. Based on the protein quantification (Bradford assay), comparable amounts of PAL protein was added per assay. Cold-stored PAL activity was monitored in the range from 0 to 0.04 unit/ml (0 to 0.04 mg/ml). Based on protein content (Bradford assay), a known amount of processed PAL (processed D) or PAL conjugated to HEP (C) were assessed. Processed PAL and HEP-PAL conjugate were found to exhibit ~40% and ~45% of 'fresh' Asp activity, respectively (FIG. 27). The target HEP-drug conjugates were active in destroying phenylalanine, the therapeutic action for treatment of PKU in mammals. Higher activity was reported when thiolation occurred at 4° C. rather than room temperature (data not shown); thus, in this case, the intrinsic enzyme stability can be problematic as for many biologics.

Figure 28:
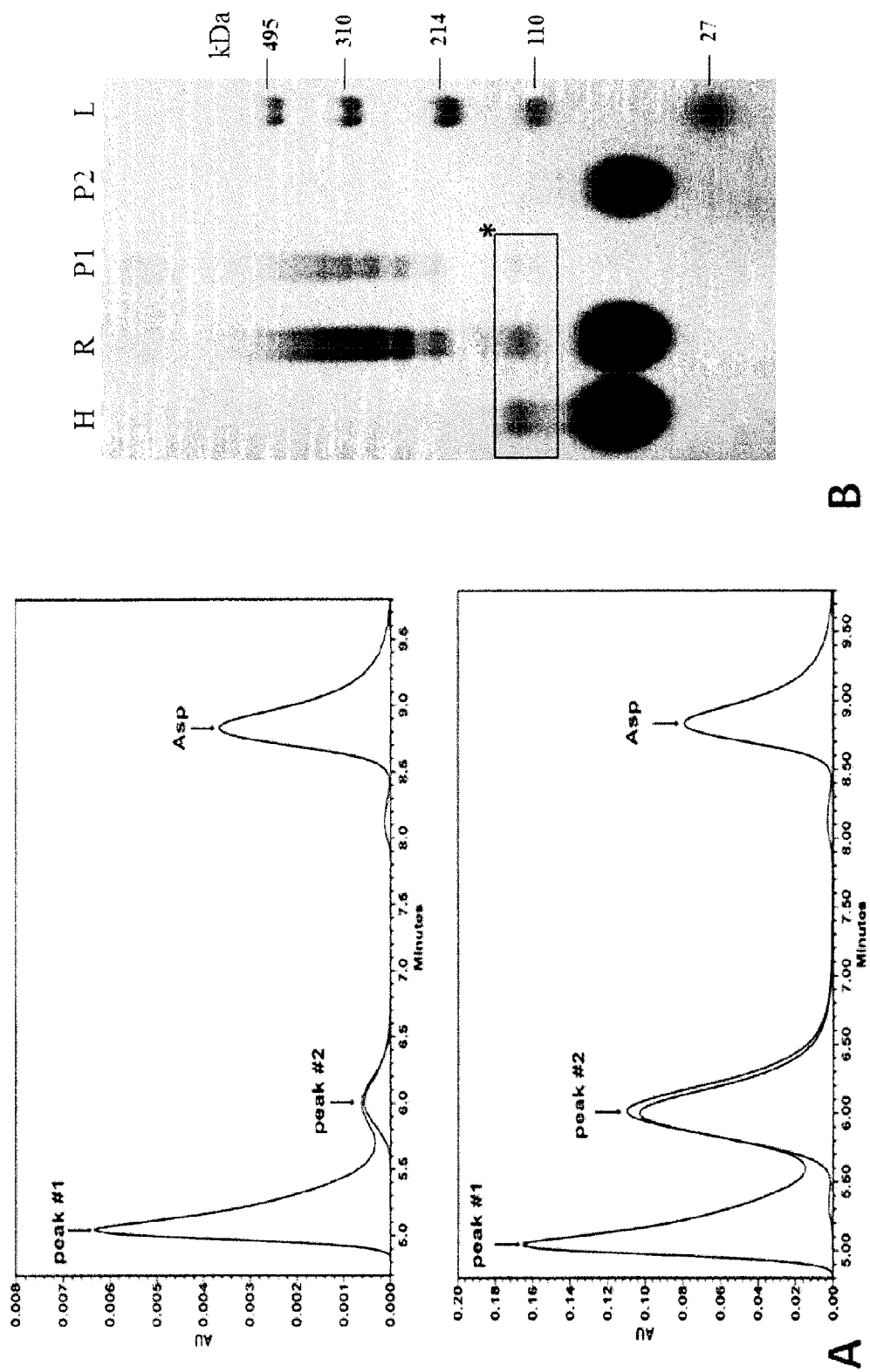
FIG. 28 depicts the chromatogram and the gel for the purification of HEP-Asparaginase conjugate. Panel A) HPLC-SEC analysis of Asp alone and HEP-Asp conjugate reaction mixture with UV absorbance detection at 214 nm (top; protein and HEP) or 280 nm (bottom; mainly protein). The peaks eluting at ~5.10 min (Peak #1) and ~6 min (Peak #2) were harvested. Panel B) The Peak #1 and Peak #2 were analyzed by 2% agarose gel and Stains-all. From left to right: HEP (H); HEP-Asp reaction mixture (R); Peak#1 (P1); Peak#2 (P2); Select HA ladder (L). (* a contaminant found in the HEP batch). P1 and P2 were found to be respectively, HEP-Asp conjugate, and HEP. The target HEP-drug conjugates were formed and purified.
Figure 29:
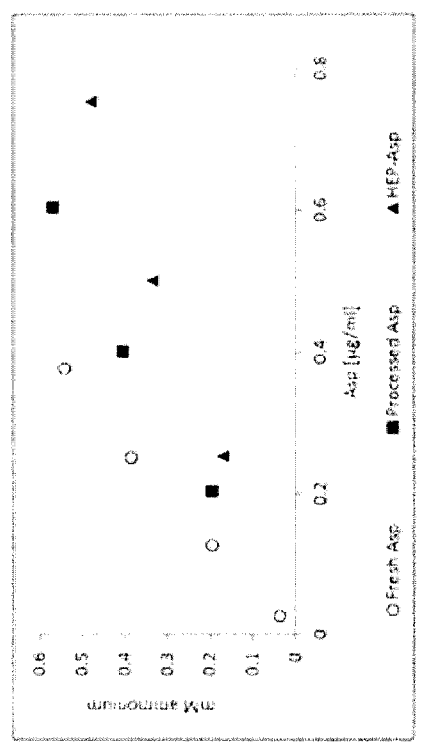
FIG. 29 depicts the enzyme activity levels of HEP-L-asparaginase conjugate. To assess the activity of Asp and HEP-Asp, conversion of L-asparagine into L-aspartate and $NH_3$ was assessed after 30 minutes of incubation at 37° C. using Nessler's reagent. The activity of unconjugated "fresh" Asp (ranging from 0 to 0.89 µg/ml) was used as reference for 100% activity. Based on protein content (Bradford assay), known amount of processed Asp, and Asp conjugated to HEP (HEP-Asp conjugate) were assessed. HEP-Asp was found to have approximately 40-60% activity as fresh Asp enzyme. The target HEP-drug conjugates were active in destroying asparagine, the therapeutic action for treatment of cancer.

For the HEP-Asp activity demonstrations, HPLC-SEC fractions containing the 55-kDa HEP-Asp conjugate (prepared in the reaction with a 1:10 Asp:HEP molar ratio) were pooled, and concentrated using spin units (Amicon, Darmstadt, Germany) with molecular weight cut off of 10 kDa (FIG. 28). HEP-Asp conjugate could be separated from free HEP as shown by agarose gel (FIG. 28). For Asp enzyme activities, the conversion of L-asparagine into L-aspartate and $NH_3$ was assessed after 30 minutes of incubation at 37° C. The level of ammonia formed is the measure of the enzyme activity, and was quantified using Nessler's reagent (Sigma-Aldrich, St. Louis, Mo.) with monitoring at 436 nm. Activity of cold-stored Asp was observed for Asp amount ranging from 0 to 0.1 unit/ml (equivalent to 0 to 0.44 µg/ml). The production of ammonia was found to be linear with respect to the enzyme concentration. Based on protein quantification (Bradford assay), comparable amount of Asp enzyme was added per assay (0.22 µg/ml). Fresh Asp activity was referred as 100%; processed Asp unconjugated and purified conjugated exhibit approximately 40-60% activity when compared to the control, showing that modification with HEP does not seriously interfere with Asp catalytic activity (FIG. 29).

Figure 30:
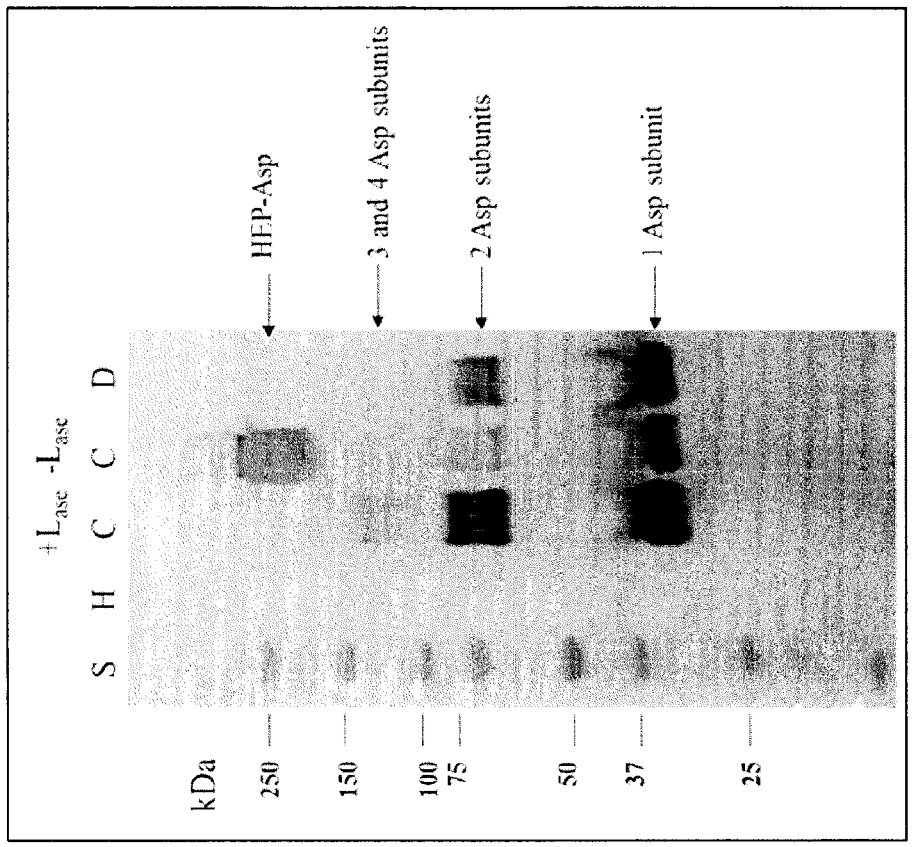
FIG. 30 depicts Western blot analyses immunoreactivity of HEP-Asp conjugate. The HEP-Asp conjugate with or without heparin lyase III ($L_{ase}$) treatment was tested; the HEP-drug conjugate should be shielded form antibody binding, but if the chains are removed using the lyase, then the antigenic surface is exposed. The samples were run on a SDS-PAGE gel, Western blotted with an anti-Asp IgG reagent, and the immune complexes detected with a colorimetric substrate. Lanes from left to right: protein Mw standard (S) (molecular masses indicated); HEP alone (H); HEP-Asp conjugate (C) with heparin lyase (+), or HEP-Asp conjugate (C) without heparin lyase (−); Asp (D). In addition to the loss of the high MW conjugate that stained very lightly with antibody, upon lyase treatment, the new lower MW band has much more immunoreactivity. The heparosan molecule of a conjugate can help shield the molecular surface of drugs from the antibody binding.

Immuno-reactivity of 55-kDa HEP-Asp conjugate was evaluated by Western blot analysis (FIG. 30). HEP-Asp was incubated with or without heparin lyase III, the bacterial degrading enzyme that can remove the heparosan chain for 2 hours at 30° C., and then loaded on SDS-PAGE gel (4-15%). The blot with HEP-Asp was incubated in the presence of anti-L-Aparaginase (anti-Asp, Pierce Biotechnology, Inc., Rockford, Ill.), at room temperature for 0.1-4 hours, in phosphate buffer at neutral pH (other incubation temperature and time, and buffer will also work). After washing to remove unbound immunoglobulin, the secondary reagent, anti-rabbit IgG alkaline phosphatase-conjugate (Sigma-Aldrich, St. Louis, Mo.), washed again, then probed with a colorimetric substrate. The untreated HEP-Asp conjugate (i.e., no heparin lyase III) exhibited far less signal that the lyase-treated sample. This indicates that HEP chains conjugated to Asp protect the enzyme against binding the antibody. If antibodies bind drug in the body, then the drug is often cleared or inactivated; thus, the utility of HEP modification to prevent antibody generation and/or antibody interaction during patient treatment is obvious.

Example 9

Heparosan-Polynucleotide
Conjugates—HEP-Aptamers

Aptamers are DNA or RNA polynucleotides or polypeptide/nucleic acid hybrids that recognize and bind to targets with high affinity and selectivity akin to antibodies. For example, pegaptanib (MACUGEN® Valeant Pharmaceuticals North America LLC, Bridgewater, N.J.), an anti-VEGF RNA aptamer conjugated to 40 kDa PEG polymer, is used for neovascula (wet) age related macular degeneration. The aptamer drug prevents blindness by binding the growth factor, thus preventing its stimulatory effects from damaging the patient's eyes.

Figure 31:
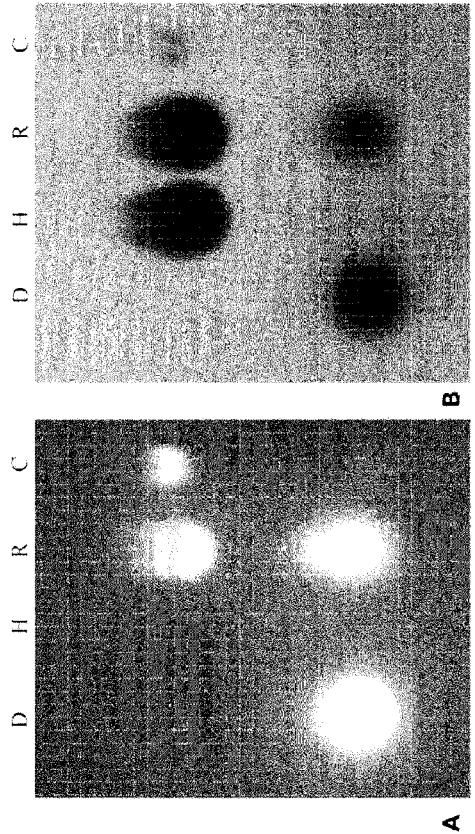
FIG. 31 depicts agarose gel analyses of HEP-anti-VEGF DNA aptamer. Samples of the HEP-aptamer conjugate and controls were run on 1×TAE 2% gel and detected first upon UV exposure (Cy3 present on aptamer fluoresces, HEP does not fluoresce) (Panel A), and then stained with Stains-all (Panel B; both DNA and HEP stain). Lanes from left to right: anti-VEGF-aptamer alone (D); HEP alone (H); HEP-aptamer conjugate reaction mixture (R); SAX purified HEP-aptamer (C). The target HEP-polynucleotide drug conjugate was formed.

In other non-limiting examples, the reducing terminal sulfhydryl-reactive group (iodoacetate or maleimide) of 38.8- or 60-kDa heparosan chains were coupled to the free sulfydryl group of an aptamer. The drug example here is an anti-VEGF DNA aptamer 5'-ACCCGTCTTCCAGA-CAAGAGTGCAGGGTT-3', containing Cy3 fluorescent dye at the 5' end and a protected thiol C6-S-S at the 3' end (GenScript USA Inc. (Piscataway, N.J.)). The C6-S-S disulfide bond was reduced by TCEP (Pierce Biotechnology, Inc., Rockford, Ill.; other reducing agents such as DTT can also be used) to expose the reactive thiol group. The reduced aptamer was then subjected to a desalting step by gel filtration to remove the small molecular weight reducing agent, and then the DNA structure was refolded (heat exposure for 2 minutes/80° C., followed by annealing via a slow cool down to room temperature). All steps were conducted in the dark. The coupling reactions are typically in neutral to slightly alkaline buffers (e.g., phosphate or HEPES at ~pH 6 to 8.5 at 0-37° C. for 0.1-24 hours (but other buffers, incubation times, and higher pH will also work as long as no sulfhydryl groups besides the target for coupling and preferably no primary amines are present). The HEP-conjugate runs at a higher molecular weight than the aptamer alone, as assessed by agarose gel electrophoresis (FIG. 31). The HEP-conjugate was purified by anion chromatography (HiTrap® Q Sepharose High Performance resin (GE Healthcare Bio-Sciences AB LLC, Uppsala, Sweden)) pre-equilibrated with a pH 7 buffer (buffer A). HEP-aptamer conjugate was separated from uncoupled free HEP and free aptamer by elution with a linear gradient to 50% of buffer B (1M NaCl in buffer A) over 20 CVs. Most of the aptamer and HEP were removed from the HEP-aptamer conjugate, as observed by UV-induced fluorescence (detects the Cy3 dye tag of the aptamer) and Stains-All staining (detects polysaccharide and DNA) (FIG. 31), and HPLC-SEC analysis (data not shown). Fractions containing the HEP-aptamer conjugate were pooled, concentrated, and exchanged into a storage buffer (neutral pH, no NaCl) in ultrafiltration spin units with molecular weight cut off of 3 kDa (Amicon, Darmstadt, Germany).

Figure 32:
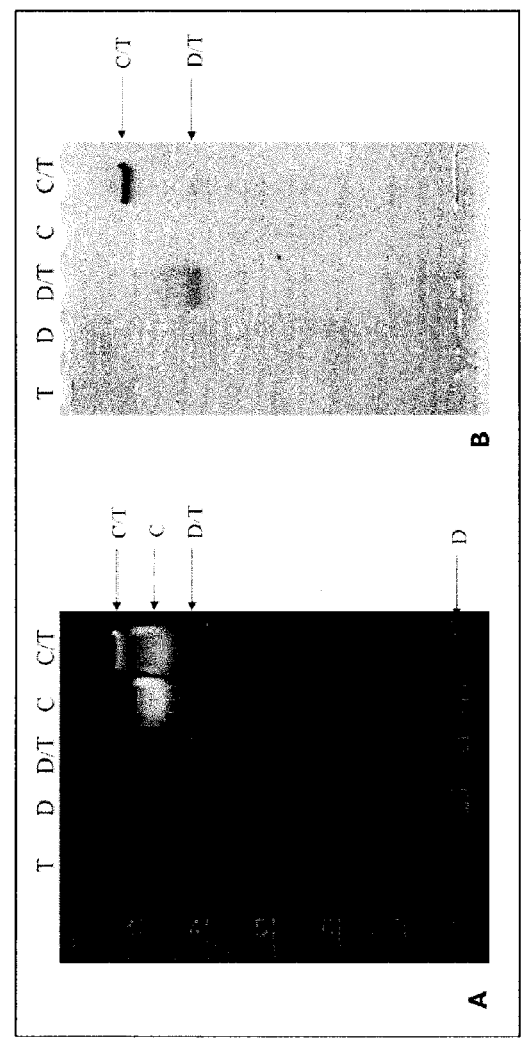
FIG. 32 depicts gel analyses of the binding of HEP-aptamer to therapeutic target. The binding of the HEP-anti-VEGF aptamer conjugate to its VEGF target (T) was analyzed by shift mobility assay using a 1×TBE PAGE gel under semi-native conditions. The gel was first detected with UV exposure (Panel A; detects only Cy3 dye present on the aptamer, but neither HEP nor protein fluoresces) and then stained with PageBlue™ blue protein staining solution (Thermo Fisher Scientific Inc., Rockford, Ill.) (Panel B; detects protein, but not HEP or DNA). Lanes from left to right: VEGF alone (T); anti-VEGF-aptamer alone (D); a mixture of anti-VEGF-aptamer with VEGF (D/T); HEP-anti-VEGF-aptamer alone (C); a mixture of HEP-anti-VEGF-aptamer with VEGF (C/T). The high MW band with both protein and UV staining shows the HEP-aptamer/VEGF complex. The HEP-polynucleotide conjugate had binding activity against its therapeutic target in mammals.
Figure 33:
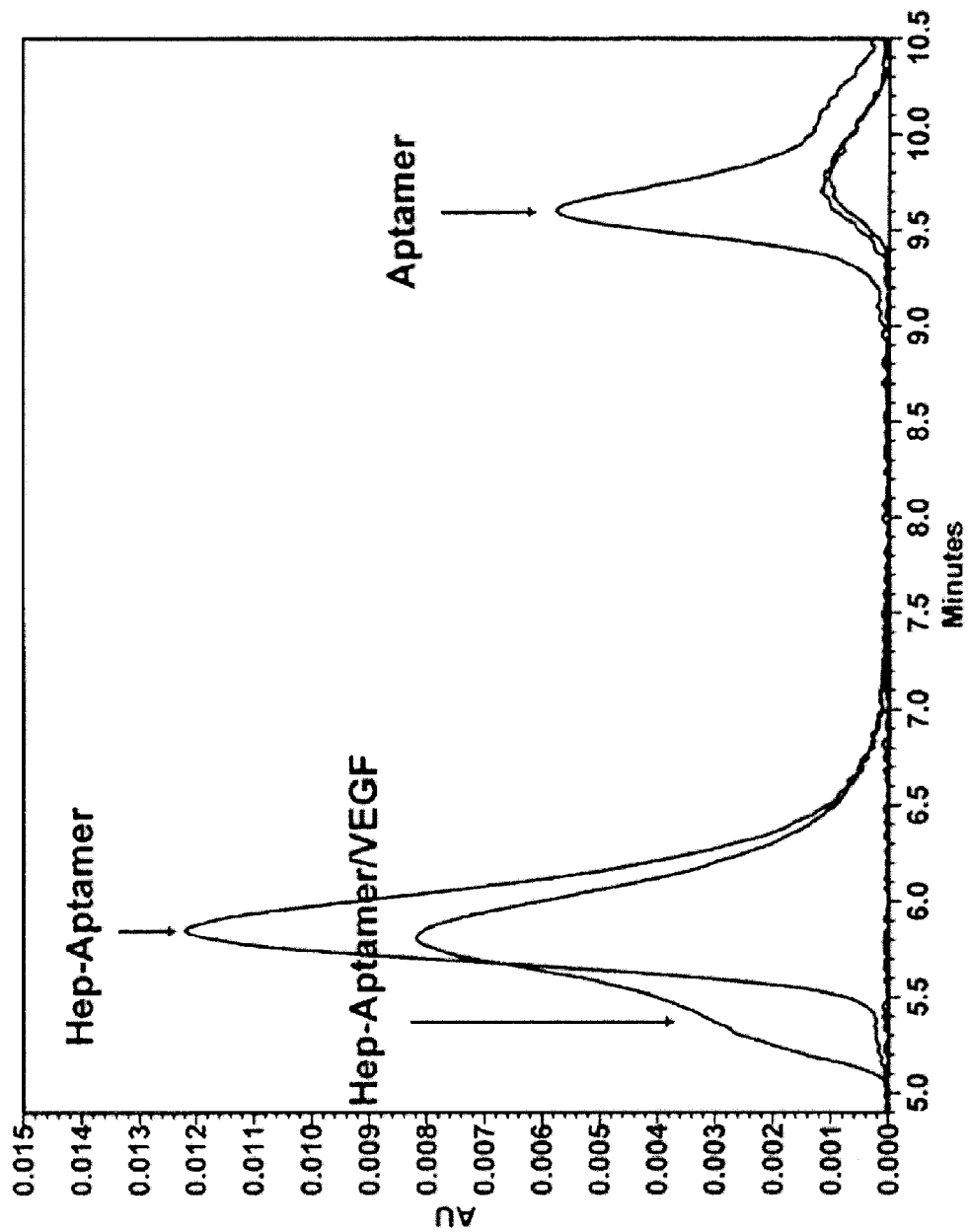
FIG. 33 depicts a profile from a HPLC-SEC analysis of binding of HEP-aptamer to target. HEP-aptamer conjugate was incubated in presence of VEGF, and analyzed by size exclusion chromatography monitoring the elution of the aptamer at 552 nm (the absorbance maxima of Cy3 dye on aptamer; HEP alone and VEGF do not show a signal at 552 nm). The loss of some material from HEP-aptamer peak (~6 min) as well as the creation of new higher molecular weight complex (indicated by faster eluting shoulder peak at ~5.4 min) show the HEP-aptamer was bound to VEGF. The HEP-polynucleotide drug conjugate had binding activity against its therapeutic target in mammals.

The biological activity and therapeutic action of the anti-VEGF aptamer resides in its binding to its target: human recombinant VEGF. Without access to a growth factor, some cells will not be able to proliferate or survive; thus, these molecules are drug targets. Some drugs or drug candidates operate by binding to a growth factor; these molecules can be in the antibody (naturally produced or synthetically constructed) or the apatamer (nucleic acids) classes (e.g., any binding partner in theory). To prove their functionality, the HEP-aptamer and VEGF were co-incubated in a 1:1 molar ratio for 3 hours at room temperature in 100 mM phosphate buffer at neutral pH (different incubation time and temperature, and buffer will also work). A shift mobility assay, using a 10% TBE gel, was used in order to assess the binding of HEP-aptamer to target (FIG. 32). The formation of an additional high molecular weight product, visible on TBE gel upon UV exposure (detecting Cy3 present on aptamer) and PageBlue™ protein staining solution (Thermo Fisher Scientific Inc., Rockford, Ill.) (detecting protein) indicates that the HEP-aptamer binds to its target. The change in the size exclusion chromatography elution pattern at 552 nm (FIG. 33) also confirms this result. As negative and positive control, VEGF was respectively incubated in the presence of heparosan (HEP) or heparin (i.e., VEGF is known to react with heparin and heparan sulfate). When observed by HPLC-SEC and 10% TBE gel, no additional products were observed in the HEP/VEGF lane as the polymer is unsulfated, while the expected product formation was observed for Heparin sulfate/VEGF lane (data not shown).

Example 10

In Vivo Analyses of a Heparosan Conjugate

Figure 34:
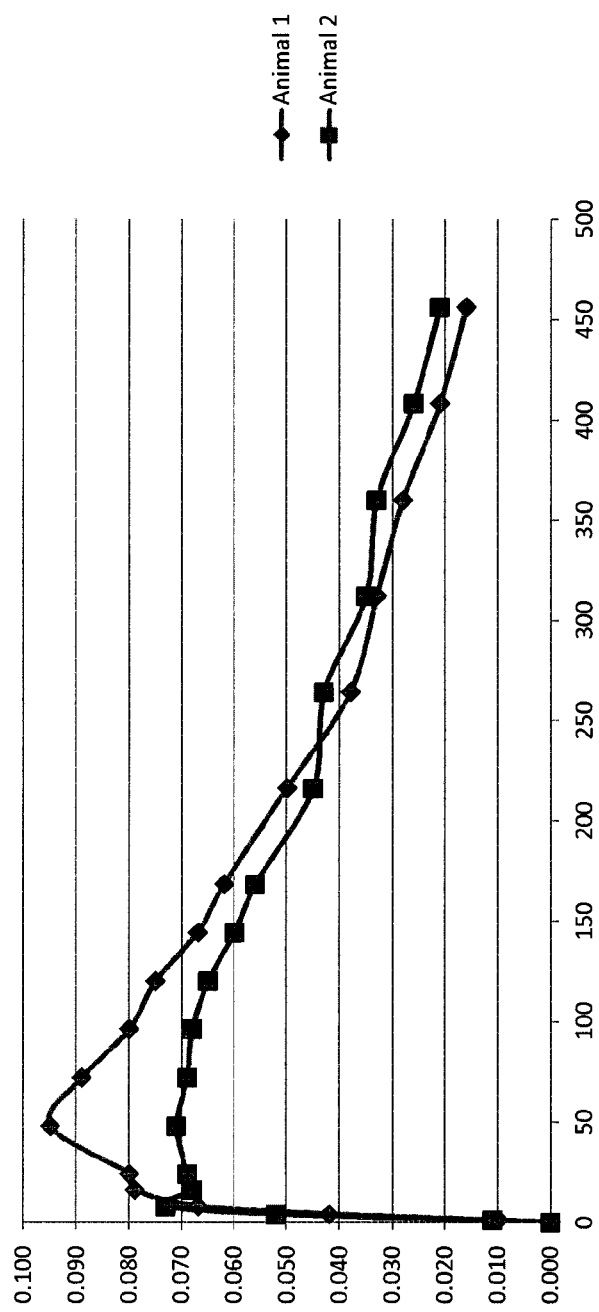
FIG. 34 depicts the pharmacokinetics (PK) of a subcutaneous (SC) injection of 100 kDa Heparosan Bolton-Hunter 125I conjugate in plasma in a non-human primate model (Cynologus monkey; performed by Xenometrics LLC, Stilwell, Kans.). The radioactivity in plasma was measured over time. This heparosan-conjugate demonstrates an approximately 8 day half-life.

FIG. 34 depicts the pharmacokinetics (PK) of a subcutaneous (SC) injection of 100 kDa Heparosan Bolton-Hunter $^{125}$I conjugate in plasma in a non-human primate model (Cynologus monkey; performed by Xenometrics LLC, Stilwell, Kans.). The radioactivity in plasma was measured over time. This heparosan-conjugate demonstrates a ~8 day half-life.

Figure 35:
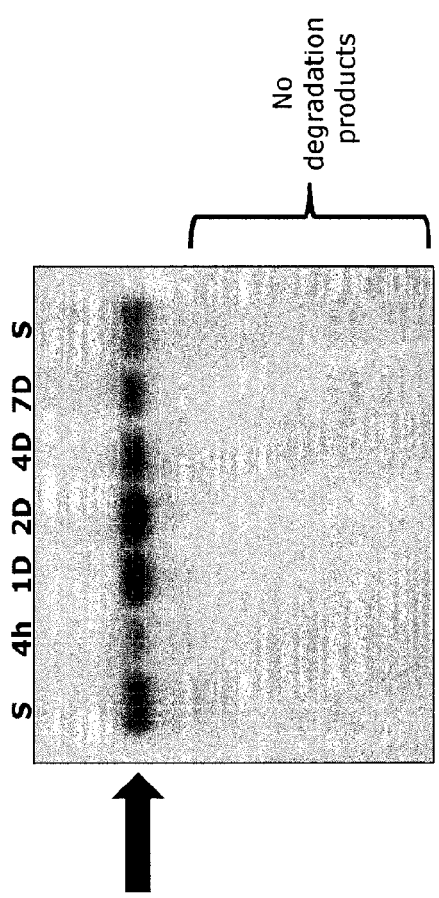
FIG. 35 depicts analysis of pooled plasma samples from 4 hours (h) to 7 days (D) post-subcutaneous injection of 100 kDa HEPtune-Bolton-Hunter $^{125}I$ conjugate in primate model by agarose gel electrophoresis and autoradiography. The same intact band as the starting probe (lane S; arrow) was observed at Day 7. The heparosan polymer is very stable in the primate bloodstream.

Pooled plasma samples from 4 hours (h) to 7 days (D) post-subcutaneous injection of 100 kDa HEPtune-Bolton-Hunter $^{125}$I conjugate were analyzed by agarose gel electrophoresis and autoradiography. As seen in FIG. 35, the same intact band as the starting probe (lane S; arrow) was observed at Day 7. Thus, the heparosan polymer is very stable in the primate bloodstream.

Figure 36:
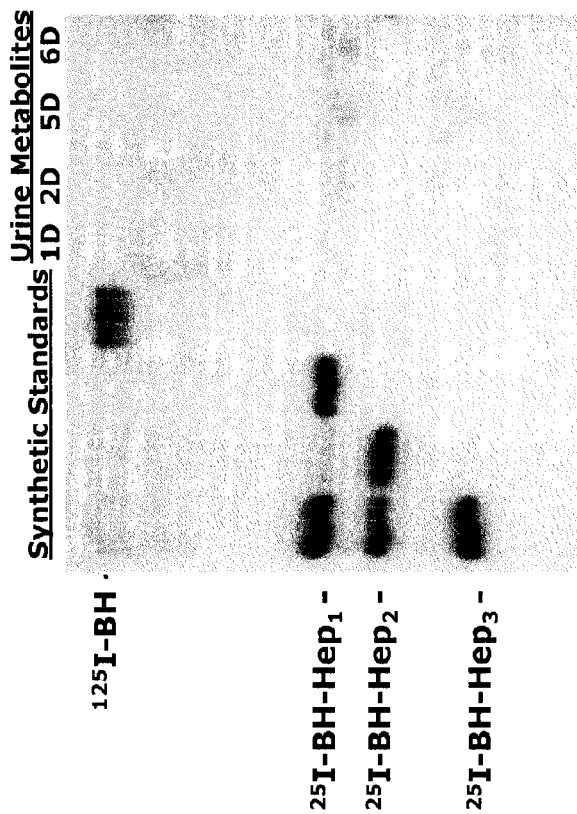
FIG. 36 depicts analysis of pooled urine samples from 1 to 6 Days (D) post-SC injection of 100 kDa HEPtune-Bolton-Hunter (BH) $^{125}I$ conjugate in primate model by Normal Phase Thin Layer Chromatography and autoradiography. The major steady state metabolite (*) appears to be GlcUA-BH, a small fragment of the original conjugate.

Next, pooled urine samples from 1 to 6 Days (D) post-SC injection of 100 kDa HEPtune-Bolton-Hunter (BH) $^{125}$I conjugate in the primate model were analyzed by Normal Phase Thin Layer Chromatography and autoradiography. As seen in FIG. 36, the major steady state metabolite (*) appears to be GlcUA-BH, a small fragment of the original conjugate.

Thus, in accordance with the presently disclosed and/or claimed inventive concept(s), there has been provided compositions containing heparosan-cargo conjugates, wherein a heparosan molecule servers as the vehicle for carrying a cargo in a heparosan-cargo conjugate, as well as methods of production and use thereof. Although the presently disclosed and/or claimed inventive concept(s) has been described in conjunction with the specific drawings and language set forth above, it is evident that many alternatives, modifications and variations will be apparent to those or ordinary skill in the art. Accordingly, it is intended to embrace all such alternatives, modifications and variations that fall within the spirit and broad scope of the presently disclosed and/or claimed inventive concept(s).

What is claimed is:
1. A pharmaceutical composition comprising:
   at least one heparosan polymer-drug conjugate, comprising:
   at least one heparosan polymer; and
   at least one therapeutic drug covalently conjugated to the at least one heparosan polymer, wherein the at least one therapeutic drug comprises at least one polypeptide, and wherein the at least one therapeutic drug remains therapeutically active after conjugation and is not an adjuvant; and
   wherein the pharmaceutical composition is a sterile pharmaceutical formulation in a unit dosage format.

2. The pharmaceutical composition of claim 1, wherein the at least one therapeutic drug is selected from the group consisting of Granulocyte Colony Stimulating Factor (G-CSF), Interferon, Insulin, Growth Hormone (hGH), Glucagon-like peptide-1 (GLP-1), Phenylalanine Ammonia-Lyase (PAL), L-Asparaginase (Asp), Anti-TNF alpha Fab', and combinations thereof.

3. The pharmaceutical composition of claim 1, wherein the at least one heparosan polymer has a mass in a range of from about 600 Da to about 4.5 MDa.

4. The pharmaceutical composition of claim 1, wherein the at least one heparosan polymer comprises an activated group with which a group on the at least one therapeutic drug has reacted to effect the covalent conjugation.

5. The pharmaceutical composition of claim 1, wherein the pharmaceutical composition comprises a plurality of drug-heparosan polymer conjugates, and wherein the plurality of heparosan polymers present in the drug-heparosan polymer conjugates is polydisperse in size.

6. The pharmaceutical composition of claim 1, wherein the pharmaceutical composition comprises a plurality of drug-heparosan polymer conjugates, and wherein the plurality of heparosan polymers present in the drug-heparosan polymer conjugates is substantially monodisperse in size.

7. The pharmaceutical composition of claim 1, wherein the at least one heparosan polymer is a linear chain.

8. The pharmaceutical composition of claim 1, wherein the at least one heparosan polymer has a branched geometry.

9. The pharmaceutical composition of claim 1, wherein at least one of:
   (a) the drug-heparosan conjugate exhibits increased retention in blood and/or lymphatic circulation of a mammalian patient when compared to drug alone; and
   (b) the drug-heparosan conjugate exhibits reduced occurrence of accumulation in organs and/or tissues of a mammalian patient when compared to drug alone.

10. A method for preparing a pharmaceutically active heparosan polymer-drug conjugate, wherein the drug comprises at least one polypeptide, the method comprising the step of:
   reacting at least one therapeutic drug with at least one heparosan polymer under conditions sufficient to effect covalent conjugation of the at least one therapeutic drug and the at least one heparosan polymer to form a reaction mixture containing one or more drug-heparosan polymer conjugates, wherein the at least one therapeutic drug comprises at least one polypeptide, and wherein the at least one therapeutic drug remains therapeutically active after conjugation and is not an adjuvant; and
   forming a sterile pharmaceutical formulation comprising the drug-heparosan polymer conjugates in a unit dosage format for administration to a mammalian patient.

11. The method of claim 10, wherein the at least one heparosan polymer has a mass in a range of from about 600 Da to about 4.5 MDa.

12. The method of claim 10, further comprising the step of modifying the heparosan polymer prior to reacting with the at least one therapeutic drug to provide at least one reactive group on the at least one heparosan polymer with which a group on the at least one therapeutic drug reacts to effect the covalent conjugation of the at least one therapeutic drug to the at least one heparosan polymer.

13. The method of claim 10, wherein the reaction mixture comprises a plurality of drug-heparosan polymer conjugates, and wherein the plurality of heparosan polymers present in the drug-heparosan polymer conjugates is polydisperse in size.

14. The method of claim 10, wherein the reaction mixture comprises a plurality of drug-heparosan polymer conjugates, and wherein the plurality of heparosan polymers present in the drug-heparosan polymer conjugates is substantially monodisperse in size.

15. The method of claim 10, wherein the at least one heparosan polymer is a linear chain.

16. The method of claim 10, wherein the at least one heparosan polymer has a branched geometry.

17. The method of claim 10, wherein at least one of:
   (a) the drug-heparosan conjugate exhibits increased retention in blood and/or lymphatic circulation of a mammalian patient when compared to drug alone; and
   (b) the drug-heparosan conjugate exhibits reduced occurrence of accumulation in organs and/or tissues of a mammalian patient when compared to drug alone.

18. The method of claim 10, wherein the at least one therapeutic drug is selected from the group consisting of a cytokine, a hormone, an enzyme, an antibody, an antibody fragment, an aptamer, and combinations thereof.

19. The method of claim 10, wherein the at least one therapeutic drug is selected from the group consisting of Granulocyte Colony Stimulating Factor (G-CSF), Interferon, Insulin, Growth Hormone (hGH), Glucagon-like peptide-1 (GLP-1), Phenylalanine Ammonia-Lyase (PAL), L-Asparaginase (Asp), Anti-TNF alpha Fab', and combinations thereof.

20. The pharmaceutical composition of claim 1, wherein the at least one heparosan polymer is characterized as being substantially non-antigenic, substantially non-immunogenic, and substantially biologically inert within extracellular compartments of a mammalian patient, being stable in the mammalian bloodstream, and being degraded intracellularly in the mammalian patient.

21. The pharmaceutical composition of claim 1, wherein the sterile pharmaceutical formulation in a unit dosage format is for injection into the patient.

22. The method of claim 10, wherein the at least one heparosan polymer is characterized as being substantially non-antigenic, substantially non-immunogenic, and substantially biologically inert within extracellular compartments of a mammalian patient, being stable in the mammalian bloodstream, and being degraded intracellularly in the mammalian patient.

23. The method of claim 10, wherein the sterile pharmaceutical formulation in a unit dosage format is for injection into the patient.

24. The pharmaceutical composition of claim 1, wherein the at least one therapeutic drug is selected from the group consisting of a cytokine, a hormone, an enzyme, an aptamer, and combinations thereof.

25. The pharmaceutical composition of claim 1, wherein the at least one therapeutic drug comprises a plurality of therapeutic drugs conjugated to the at least one heparosan polymer.

26. The pharmaceutical composition of claim 1, wherein the at least one therapeutic drug comprises an antibody or an antibody fragment.

27. The method of claim 10, wherein the at least one heparosan polymer is reacted with a plurality of therapeutic drugs under conditions sufficient to effect covalent conjugation of the plurality of therapeutic drugs to the at least one heparosan polymer.

* * * * *